US012385053B2

(12) United States Patent
Nuccio et al.

(10) Patent No.: US 12,385,053 B2
(45) Date of Patent: Aug. 12, 2025

(54) GENOMIC ALTERATION OF PLANT GERMLINE

(71) Applicant: INARI AGRICULTURE TECHNOLOGY, INC., Cambridge, MA (US)

(72) Inventors: Michael Lee Nuccio, Salem, NH (US); Mircea Achiriloaie, Cambridge, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 397 days.

(21) Appl. No.: 17/754,973

(22) PCT Filed: Oct. 22, 2020

(86) PCT No.: PCT/US2020/056859
§ 371 (c)(1),
(2) Date: Apr. 18, 2022

(87) PCT Pub. No.: WO2021/081200
PCT Pub. Date: Apr. 29, 2021

(65) Prior Publication Data

US 2022/0389438 A1 Dec. 8, 2022

Related U.S. Application Data

(60) Provisional application No. 62/924,542, filed on Oct. 22, 2019.

(51) Int. Cl.
*C12N 15/82* (2006.01)

(52) U.S. Cl.
CPC ................................ *C12N 15/8213* (2013.01)

(58) Field of Classification Search
None
See application file for complete search history.

(56) References Cited

U.S. PATENT DOCUMENTS 5,583,210 A 12/1996 Neill et al.
5,602,321 A 2/1997 John
5,703,049 A 12/1997 Rao
5,885,801 A 3/1999 Rao
5,885,802 A 3/1999 Rao
5,990,389 A 11/1999 Rao et al.
6,453,242 B1 9/2002 Eisenberg et al.
6,479,626 B1 11/2002 Kim et al.
6,534,261 B1 3/2003 Cox et al.
6,794,136 B1 9/2004 Eisenberg et al.
6,903,185 B2 6/2005 Kim et al.
7,153,949 B2 12/2006 Kim et al.
10,113,163 B2 10/2018 Liu et al.
10,308,947 B2 6/2019 Yang et al.
2004/0082770 A1 4/2004 Castle et al.
2005/0050588 A1 3/2005 Lucas et al.
2011/0093982 A1 4/2011 Samuel et al.
2011/0247100 A1 10/2011 Samboju et al.
2016/0208243 A1 7/2016 Zhang et al.
2017/0342427 A1 11/2017 Kragler et al.
2019/0264218 A1 * 8/2019 Shultz ................ C12N 15/8213
2019/0292553 A1 9/2019 Gao et al.
2019/0300890 A1 10/2019 Brower-Toland et al.

FOREIGN PATENT DOCUMENTS

WO WO-1998020133 A2 5/1998
WO WO-2003092360 A2 11/2003
WO WO-2017178633 A1 10/2017
WO WO-2017189308 A1 11/2017
WO WO-2018086623 A1 5/2018
WO WO-2018176009 A1 9/2018
WO WO-2021041001 A2 * 3/2021 ............ C12N 15/11

OTHER PUBLICATIONS

NCBI GQ395500 2009, ncbi.nlm.nih.gov/nucleotide/GQ395500.1 (Year: 2019).*
Tang et al 2019, Plant Biotechnology Journal 17: 1431-1445; first published online Dec. 24, 2018 (Year: 2018).*
NCBI GQ395500 2009, ncbi.nlm.nih.gov/nucleotide/GQ395500.1 (Year: 2009).*
Ali et al., (2015). "Efficient Virus-Mediated Genome Editing in Plants Using the CRISPR/Cas9 System," Mol. Plant, 8:1288-1291.
Baltes et al., (2014). "DNA Replicons for Plant Genome Engineering," Plant Cell, 26(1):151-63.
Cho et al., (2015). "Polypyrimidine tract-binding proteins of potato mediate tuberization through an interaction with StBEL5 RNA," J. Exp. Bot, 66:6835-6847.
Cody et al., (2017). "Multiplexed Gene Editing and Protein Overexpression Using a Tobacco mosaic virus Viral Vector," Plant Physiol., 175:23-35.
Dong et al., (2012). "A Gene Regulatory Network Model for Floral Transition of the Shoot Apex in Maize and Its Dynamic Modeling," PLoS One, 7(8):e43450, 11 pages.
Ezzat et al., (2011). "PepFect 14, a novel cell-penetrating peptide for oligonucleotide delivery in solution and as solid formulation," Nucleic Acids Res., 39:5284-5298.

(Continued)

*Primary Examiner* — Brent T Page
*Assistant Examiner* — Aleksandar Radosavljevic
(74) *Attorney, Agent, or Firm* — MORRISON & FOERSTER LLP

(57) ABSTRACT

Compositions containing chimeric RNA molecules which comprise meristem targeting sequences that are fused to RNA cargo sequences that include gene editing molecules are provided. Methods of using the compositions to efficiently edit plant genomes without intervening tissue culture steps are also provided. The solutions described here relate to engineered RNA molecules useful in producing plants with altered genomes. As such, it relates to substantially purified compositions, vectors, systems, as well as genomes of plants.

23 Claims, 2 Drawing Sheets

Figure 1A:
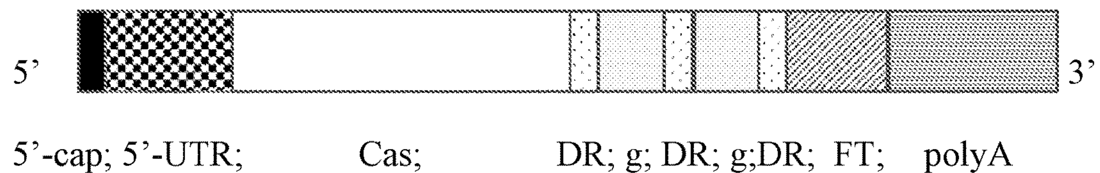
Figure 1B:
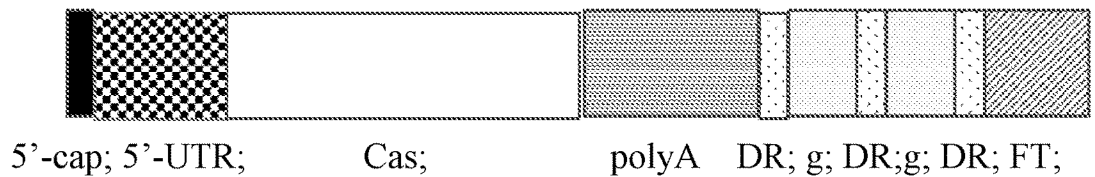
Figure 1B:
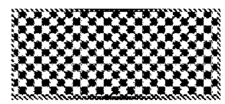
Figure 1B:
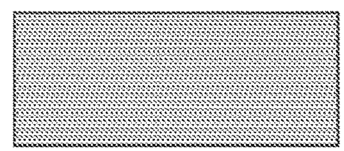
Figure 1B:
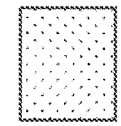
Figure 1B:
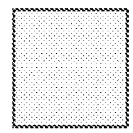

Specification includes a Sequence Listing.

(56) References Cited

OTHER PUBLICATIONS

Gao et al., (2019). "Rescue of a plant cytorhabdovirus as versatile expression platforms for planthopper and cereal genomic studies," New Phytol., 223:2120-2133.
Guo et al., (2010). "Directed evolution of an enhanced and highly efficient Fokl cleavage domain for zinc finger nucleases," J. Mol. Biol., 400:96-107.
Haywood et al., (2005). "Phloem long-distance trafficking of Gibberellic Acid-Insensitive RNA regulates leaf development," Plant J., 42:49-68.
Huang et al., (2018). "Mobility of Antiflorigen and PEBP mRNAs in Tomato-Tobacco Heterografts," Plant Physiol., 178:783-794.
International Search Report and Written Opinion received for International Patent Application No. PCT/US2020/056859 mailed on Feb. 10, 2021, 10 pages.
Jackson et al., (2012). "Systemic movement of FT mRNA and a possible role in floral induction," Front. Plant Sci., 3:127, 4 pages.
Jarver et al., (2012). "Peptide-mediated Cell and In Vivo Delivery of Antisense Oligonucleotides and siRNA," Mol. Therapy Nucleic Acids, 1(6):e27, 17 pages.
Jiang et al. (2019). "Natural variations of FT family genes in soybean varieties covering a wide range of maturity groups," BMC Genomics, 20(1):230, 16 pages.
Kehr et al., (2018). "Long distance RNA movement," New Phytologist, 218(1):29-40.
Kong et al., (2010). "Two coordinately regulated homologs of Flowering Locus T are involved in the control of photoperiodic flowering in soybean," Plant Physiol., 154(3):1220-31.
Li et al., (2011). "Mobile FT mRNA contributes to the systemic florigen signaling in floral induction," Sci. Rep., 1:73, 6 pages.
Lilley et al. (1989) Proceedings of the World Congress on Vegetable Protein Utilization in Human Foods and Animal Feedstuffs, ed. Applewhite (American Oil Chemists Society, Champaign, III.), pp. 497-502.
Lu et al., (2010). "Arginine-rich intracellular delivery peptides synchronously deliver covalently and noncovalently linked proteins into plant cells," J. Agric. Food Chem., 58:2288-2294.
Luo et al., (2016). "Generation of TALE nickase-mediated gene-targeted cows expressing human serum albumin in mammary glands," Scientific Reports, 6:20657, 11 pages.
Maher et al., (2019). "Plant gene editing through de novo induction of meristems," Nature Biotechnology, 38(1):84-89, 17 pages.
Mahfouz et al., (2011). "De novo-engineered transcription activator-like effector (TALE) hybrid nuclease with novel DNA binding specificity creates double-strand breaks," PNAS USA, 108:2623-2628.
Mahfouz et al., (2011). "TALE nucleases and next generation GM crops," GM Crops, 2:99-103.
Mikami et al., (2017). "In Planta Processing of the SpCas9-gRNA Complex," Plant Cell Physiol., 58(11):1857-1867.
Mohanta et al., (2017). "Genome Editing Tools in Plants," Genes, 8:399, 24 pages.
Pausch et al., (2020). "CRISPR-Caso from huge phages is a hypercompact genome editor," Science, 369(6501):333-337, 11 pages.
Pedersen et al., (1986). "Sequence analysis and characterization of a high sulfur zein protein of Mr 15,000," J. Biol. Chem., 261:6279-6284.
Rodriguez-Leal et al., (2017). "Engineering Quantitative Trait Variation for Crop Improvement by Genome Editing," Cell, 171(2):470-480.
Ruiz-Medrano et al., (1999). "Phloem long-distance transport of CmNACP mRNA: implications for supracellular regulation in plants," Development, 126:4405-4419.
Sandhya et al., (2020). "The present and potential future methods for delivering CRISPR/Cas9 components in plants," Journal of Genetic Engineering and Biotechnology, 18(25):1-11.
Schubert et al., (1988). "Cloning of the Alcaligenes eutrophus genes for synthesis of poly-beta-hydroxybutyric acid (PHB) and synthesis of PHB in *Escherichia coli*," J. Bacteriol., 170:5837-5847.
Sun et al. (2011). "GmFT2a, a soybean homolog of Flowering Locus T, is involved in flowering transition and maintenance," PLoS One, 6(12):e29238, 12 pages.
Takeshima et al., (2019). "Functional divergence between soybean Flowering Locus T orthologues FT2a and FT5a in post-flowering stem growth," J Exp Bot., 70(15):3941-3953.
Unnamalai et al., (2004). "Cationic oligopeptide-mediated delivery of dsRNA for post-transcriptional gene silencing in plant cells," FEBS Letters, 566:307-310.
Wu et al., (2014). "TALE nickase mediates high efficient targeted transgene integration at the human multi-copy ribosomal DNA locus," Biochem Biophys Res Commun., 446(1):261-6.
Yan et al., (2019). "Functionally diverse type V CRISPR-Cas systems," Science, 363:88-91, 4 pages.
Zhang et al., (2016). "tRNA-Related Sequences Trigger Systemic mRNA Transport in Plants," Plant Cell, 28:1237-1249.
Kirihara et al., (1988). "Isolation and sequence of a gene encoding a methionine-rich 10-kDa zein protein from maize," Gene, 71:359-70.
Ali et al., (2018). "Pea early-browning virus-mediated genome editing via the CRISPR/Cas9 system in Nicotiana benthamiana and *Arabidopsis*," Virus Res., 244:333-337, 5 pages.
Du et al., (2016). "Efficient targeted mutagenesis in soybean by TALENs and CRISPR/Cas9," J. Biotech, 217:90-97.
Fonfara et al., (2016). "The CRISPR-associated DNA-cleaving enzyme Cpf1 also processes precursor CRISPR RNA," Nature, 532:517-521, 19 pages.
Kim et al., (2001). "Developmental changes due to long-distance movement of a homeobox fusion transcript in tomato," Science, 293:287-289.
Masumura et al., (1989). "cDNA cloning of an mRNA encoding a sulfur-rich 10 kDa prolamin polypeptide in rice seeds," Plant Mol. Biol., 12:123-130.

* cited by examiner

KEY:

5'-cap

5'-UTR

Cas

DR g (gRNA)

FT polyA

KEY:

5'-cap

5'-UTR

Cas polyA

DR g (gRNA)

FT

SEQUENCE LISTING

```
<160> NUMBER OF SEQ ID NOS: 62

<210> SEQ ID NO 1
<211> LENGTH: 103
<212> TYPE: DNA
<213> ORGANISM: Arabidopsis thaliana

<400> SEQUENCE: 1

atgtctataa atataagaga ccctcttata gtaagcagag ttgttggaga cgttcttgat      60

ccgtttaata gatcaatcac tctaaaggtt acttatggcc aaa                       103


<210> SEQ ID NO 2
<211> LENGTH: 975
<212> TYPE: DNA
<213> ORGANISM: Arabidopsis thaliana

<400> SEQUENCE: 2

agttaatgca aatccgaaac agtataaata tgtgtagagg gttcatgcct atgatacaaa      60

ttaaagaagc agaaacaaaa acaagtaaaa cagaaacaat caacacagag aaaccacctg     120

tttgttcaag atcaaagatg tctataaata taagagaccc tcttatagta agcagagttg     180

ttggagacgt tcttgatccg tttaatagat caatcactct aaaggttact tatggccaaa     240

gagaggtgac taatggcttg gatctaaggc cttctcaggt tcaaaacaag ccaagagttg     300

agattggtgg agaagacctc aggaacttct atactttggt tatggtggat ccagatgttc     360

caagtcctag caaccctcac ctccgagaat atctccattg gttggtgact gatatccctg     420

ctacaactgg aacaaccttt ggcaatgaga ttgtgtgtta cgaaaatcca agtcccactg     480

caggaattca tcgtgtcgtg tttatattgt ttcgacagct tggcaggcaa acagtgtatg     540
```

```
caccagggtg gcgccagaac ttcaacactc gcgagtttgc tgagatctac aatctcggcc    600

ttcccgtggc cgcagttttc tacaattgtc agagggagag tggctgcgga ggaagaagac    660

tttagatggc ttcttccttt ataaccaatt gatattgcat actctgatga gatttatgca    720

tctatagtat tttaatttaa taaccatttt atgatacgag taacgaacgg tgatgatgcc    780

tatagtagtt caatatataa gtgtgtaata aaaatgagag ggggaggaaa atgagagtgt    840

tttacttata tagtgtgtga tgcgataatt atattaatct acatgaaatg aagtgttata    900

tttatacttt acgtgtattc atttcttttc gatgcaaaaa tcaggcagtg ggaagaatct    960

gctgttttac ttttg                                                     975


<210> SEQ ID NO 3
<211> LENGTH: 762
<212> TYPE: DNA
<213> ORGANISM: Zea mays

<400> SEQUENCE: 3

ttgagagttc taataagagc aacggccaat accattagcg agttattttt ctgcaatata     60

tgtcagcaac cgatcatttg gttatggctc gtgtcataca ggatgtattg gatcccttta    120

caccaaccat tccactaaga ataacgtaca acaataggct acttctgcca agtgctgagc    180

taaagccatc cgcggttgta agtaaaccac gagtcgatat cggtggcagt gacatgaggg    240

ctttctacac cctggtactg attgacccgg atgccccaag tccaagccat ccatcactaa    300

gggagtactt gcactggatg gtgacagata ttccagaaac aactagtgtc aactttggcc    360

aagagctaat attttatgag aggccggacc caagatctgg catccacagg ctggtatttg    420

tgctgttccg tcaacttggc agggggacag tttttgcacc agaaatgcgc cacaacttca    480

actgcagaag ctttgcacgg caatatcacc tcagcattgc caccgctaca catttcaact    540

gtcaaaggga aggtggatcc ggcggaagaa ggtttaggga agagtagaaa ccataggcca    600

ctgcatggtc acactataga aatatcatca ataatgtgca ctatattgaa tcaatgcacc    660

acctctatat gctgaatgtt atgtatctca aactatgatt gtactgactt gaaaggttga    720

gagcttagtc tcttagcaga atatagcaca atattactag ta                       762


<210> SEQ ID NO 4
<211> LENGTH: 531
<212> TYPE: DNA
<213> ORGANISM: Glycine max

<400> SEQUENCE: 4

atgcctagtg gaagtaggga tcctctcgtt gttgggggag taattgggga tgtattggat     60

ccttttgaat attctattcc tatgagggtt acctacaata acagagatgt cagcaatgga    120

tgtgaattca aaccctcaca agttgtcaac caaccaaggg taaatatcgg tggtgatgac    180

ctcaggaact tctatacttt gattgcggtt gatcccgatg cacctagccc aagtgacccc    240

aatttgagag aatacctcca ttggttggtg actgatatcc cagcaacaac aggggctagt    300

ttcggccatg aggttgtaac atatgaaagt ccaagaccaa tgatggggat tcatcgtttg    360

gtgtttgtgt tatttcgtca actgggtagg gagaccgtgt atgcaccagg atggcgccag    420

aatttcaaca ctaaagaatt tgctgaactt tacaaccttg gattgccagt tgctgctgtc    480

tatttcaaca ttcagaggga atctggttct ggtggaagga ggttatacta a              531


<210> SEQ ID NO 5
<211> LENGTH: 103
```

```
<212> TYPE: RNA
<213> ORGANISM: Arabidopsis thaliana

<400> SEQUENCE: 5

augucuauaa auauaagaga cccucuuaua guaagcagag uuguuggaga cguucuugau      60

ccguuuaaua gaucaaucac ucuaaagguu acuuauggcc aaa                       103


<210> SEQ ID NO 6
<211> LENGTH: 975
<212> TYPE: RNA
<213> ORGANISM: Arabidopsis thaliana

<400> SEQUENCE: 6

aguuaaugca aauccgaaac aguauaaaua uguguagagg guucaugccu augauacaaa      60

uuaaagaagc agaaacaaaa acaaguaaaa cagaaacaau caacacagag aaaccaccug     120

uuuguucaag aucaaagaug ucuauaaaua uaagagaccc ucuuauagua agcagaguug     180

uuggagacgu ucuugauccg uuuaauagau caaucacucu aaagguuacu uauggccaaa     240

gagaggugac uaauggcuug gaucuaaggc cuucucaggu ucaaaacaag ccaagaguug     300

agauuggugg agaagaccuc aggaacuucu auacuuuggu uaugguggau ccagauguuc     360

caaguccuag caacccucac cuccgagaau aucuccauug guuggugacu gauaucccug     420

cuacaacugg aacaaccuuu ggcaaugaga uuguguguua cgaaaaucca agucccacug     480

caggaauuca ucgugucgug uuuauauugu uucgacagcu uggcaggcaa acaguguaug     540

caccagggug gcgccagaac uucaacacuc gcgaguuugc ugagaucuac aaucucggcc     600

uucccguggc cgcaguuuuc uacaauuguc agagggagag uggcugcgga ggaagaagac     660

uuuagauggc uucuuccuuu auaaccaauu gauauugcau acucugauga gauuuaugca     720

ucuauaguau uuuaauuuaa uaaccauuuu augauacgag uaacgaacgg ugaugaugcc     780

uauaguaguu caauauauaa guguguaaua aaaaugagag ggggaggaaa augagagugu     840

uuuacuuaua uaguguguga ugcgauaauu auauuaaucu acaugaaaug aaguguuaua     900

uuuauacuuu acguguauuc auuucuuuuc gaugcaaaaa ucaggcagug ggaagaaucu     960

gcuguuuuac uuuug                                                      975


<210> SEQ ID NO 7
<211> LENGTH: 762
<212> TYPE: RNA
<213> ORGANISM: Zea mays

<400> SEQUENCE: 7

uugagaguuc uaauaagagc aacggccaau accauuagcg aguuauuuuu cugcaauaua      60

ugucagcaac cgaucauuug guuauggcuc gugucauaca ggauguauug gaucccuuua     120

caccaaccau uccacuaaga auaacguaca acaauaggcu acuucugcca agugcugagc     180

uaaagccauc cgcgguugua aguaaaccac gagucgauau cgguggcagu gacaugaggg     240

cuuucuacac ccugguacug auugacccgg augccccaag uccaagccau ccaucacuaa     300

gggaguacuu gcacuggaug gugacagaua uuccagaaac aacuagugucaacuuuggcc     360

aagagcuaau auuuuaugag aggccggacc caagaucugg cauccacagg cugguauuug     420

ugcuguuccg ucaacuuggc agggggacag uuuuugcacc agaaaugcgc cacaacuuca     480

acugcagaag cuuugcacgg caauaucacc ucagcauugc caccgcuaca cauuucaacu     540

gucaaaggga agguggaucc ggcggaagaa gguuuaggga agaguagaaa ccauaggcca     600
```

cugcauggu c acacuauaga aauaucauca auaaugugca cuauauugaa ucaaugcacc 660
accucuauau gcugaauguu auguaucuca aacuaugauu guacugacuu gaaagguuga 720
gagcuuaguc ucuuagcaga auauagcaca auauuacuag ua 762

<210> SEQ ID NO 8
<211> LENGTH: 531
<212> TYPE: RNA
<213> ORGANISM: Glycine max

<400> SEQUENCE: 8
augccuagug gaaguaggga uccucucguu guuggggggag uaauugggga uguauuggau 60
ccuuuugaau auucuauucc uaugaggguu accuacaaua acagagaugu cagcaaugga 120
ugugaauuca aacccucaca aguugucaac caaccaaggg uaaauaucgg uggugaugac 180
cucaggaacu ucuauacuuu gauugcgguu gaucccgaug caccuagccc aagugacccc 240
aauuugagag aauaccucca uugguuggug acugauaucc cagcaacaac aggggcuagu 300
uucggccaug agguuguaac auaugaaagu ccaagaccaa ugauggggau ucaucguuug 360
guguuugugu uauuucguca acuggguagg gagaccgugu augcaccagg auggcgccag 420
aauuucaaca cuaaagaauu ugcugaacuu uacaaccuug gauugccagu ugcugcuguc 480
uauuucaaca uucagaggga aucugguucu gguggaagga gguuauacua a 531

<210> SEQ ID NO 9
<211> LENGTH: 699
<212> TYPE: RNA
<213> ORGANISM: Cucurbita maxima

<400> SEQUENCE: 9
ggggcuucaa aagagaauua ggucaccucc cagcucgguu ucgacacgcc augccgagaa 60
aucgugaccc ucuagucguc gggagaguga ucggcgacgu cgucgacucg uucucgaggu 120
ccaucucgau uaggguuguu uacgacucga gggaaguuaa caaugggugu gagcucaaac 180
ccucucaagc ugucaacaag ccaagaguug agauuggugg cacugaccuu cgcaccuucu 240
ucacuuuggu uaugguggau cccgacgcuc cuagcccuag cgaucccaau cuaagagaau 300
acuugcauug guuagugacc gauauuccag cuacaaccga ggcaaccuuu ggacaagaga 360
uagugugcua cgagaaucca agaccaacgg ugguauucca ccguuuugug cugguc uugu 420 uccggcagcu cggaaggcaa acgguguaug cuccugggug gcgccagaac uucaacacca 480
gacacuuugc agagcuuuac aaucuugguu cgccagucgc cgccgucuau uucaauugcc 540
aaagggaaaa uggcuccggu ggaaggagaa gagccggcga ugaauguuca uaaaaacacu 600
ucacuucaca uuauauuauc aaccaauaua uuguaauaac augguucacg uuucuaucua 660
auagauuaua uauuuuuaau aaguucguga aaaaaaaaa 699

<210> SEQ ID NO 10
<211> LENGTH: 858
<212> TYPE: RNA
<213> ORGANISM: Cucurbita maxima

<400> SEQUENCE: 10
gagacaauua cgcaucuuuu cagcucucuc acguacuacc auccucucga cgccaugccg 60
agagaccgug acccuuuggu cguugggaga gucaucggcg acguuaucga cucguucacg 120
aaguccauuu cgauuagggc uacuuacaac aacagggaaa uuagcaaugg cugugagcuc 180
aaacccucuc aaguugucaa ccagccaaga guugagauug guggcacuga ccuucgcacc 240

```
uucuucacuu ugguuauggu ggauccugau gcuccuagcc cuagugaucc uaaucuaagg    300

gaauacuugc auugguuggu gacugauauc ccagcuacaa cuggagcgaa cuuuggucaa    360

gagaucgugu gcuaugagag cccaagaccc acggugggua uccaucgucu ugugcuggug    420

uuguuucgac agcuuggaag gcaaacggug uacgcuccug gguggcgcca gaacuucaac    480

acaagagacu uugcagagcu uuacaaucuu ggcuugccgg uggcagccgu uuauuucaau    540

ugccaaaggg aaaguggguc ugguggaagg agaagaaccc aagaugauuu cuaagcccca    600

cuucacauua auuagauuaa uauuauagcc ccuaucaucu auuaauccua ccuugcuuuu    660

agauuaaccu uuauuuugag uacacccaug gaucauaaau aagcccaaaa ugcauuccua    720

auauugcucu uauacucguu ucguaugaau cacugucuuu ucuucuuugu uuuucuuguu    780

cgaguguuca uguugugcuu uuuuuuucgu augaaucaaa guagaagauc aagauucgaa    840

aaaaaaaaaa aaaaaaa                                                   858
```

```
<210> SEQ ID NO 11
<211> LENGTH: 596
<212> TYPE: RNA
<213> ORGANISM: Vitis vinifera

<400> SEQUENCE: 11

cccucuugua uuguaucggu gaggugugug ugaugccuag ggaaagggau ccucuuguug     60

uugggcgcgu ugucggggau guucuggacc ccuuucucag guccaucacu cugagggaga    120

ccuacaauaa uagagaagua gcaaauggcu gugaguucag acccucucag cuagucagcc    180

aaccuagggu ggacauugga ggggaugacu ugaggaccuu cuauacuuug guuauggugg    240

acccugacgc uccaagcccc aguaauccga accuaaggga guacuuacau ugguugguga    300

cugauauucc agcaacuacu ggggcaaacu ucggccaaga gauugugugu uaugagagcc    360

cacgcccaac agcugggauu caucgcuuug uuuuuguauu guuucgccaa cuggguaggc    420

agacagugua ugcaccaggg uggcgccaaa auuucaacac uagggacuuu gcugagcuuu    480

auaaucuugg uuugccuguu gcugcuguuu auuuuaacug ccaaagggag ggcggcucgg    540

guggucgaag aucauaauca auggauuuug uacgcaaccu ugcgacuuac aaaggc        596
```

```
<210> SEQ ID NO 12
<211> LENGTH: 525
<212> TYPE: RNA
<213> ORGANISM: Malus domestica

<400> SEQUENCE: 12

augccuaggg auagggaccc ccuuguuguu ggacgagugg uuggugaugu uuuagacccc     60

uucacaaggu cuguuucucu gagggugacc uacgguacua aggagguuaa caaugguugu    120

gagcucaaac cuucugaagu uguccaacaa ccuagagcug auauuggugg agacgaucuc    180

aggacuuucu acacucuggu cauggugau ccugaugcac ccagcccaag ugaccccaac    240

cuaaaggaau auuugcauug guugguuacc gauauuccag caacuacugc ggcaagcuuc    300

gggcaagaga ucguguguua ugaaagucca cggccaacag uggggauuca ucgcuuuguu    360

uuggugugu uucgccaauu ggguaggcaa acgguguaug cuccgggaug gcgccagaac    420

uucaauacca gagacuucgc cgagcuuuau aaucuuggau uaccggugnc ugucgucuau    480

uuuaacugcc aaagggaggg cggcuccggu ggaaggagaa gauaa                    525
```

```
<210> SEQ ID NO 13
```

<211> LENGTH: 745
<212> TYPE: RNA
<213> ORGANISM: Citrus unshiu

<400> SEQUENCE: 13

```
ggcacgagga auagucuuac uacuuuugua ggcugugugu guauuuguuu gugcuuagug     60

uuguugagug uuuguuugug uuuaguguug uugauauguc uagcagggag agagauccuc    120

uuauuguugg ccgcguuguu ggugauguuc uugacaauuu uacaagaaca auuccaauga    180

ggauuaccua uucaaacaag gauguuaaua auggccguga gcucaaaccu ucugaaguuc    240

ugaaccagcc uagggcugaa auuggugugg augaucuuag gacauuuuau acuuugguaa    300

ugguugaucc ugaugcacca agcccaagug accccagccu uagggaguau uugcauuggu    360

uggugacuga uauuccagca accacagggg ccagcuuugg ccaagagauu gugaacuaug    420

aaagcccuag gccaacgaug gggauucaca gguuugucuu uguguuguuc cggcaacuug    480

ggaggcagac uguuuaugca ccagggugge gucagaacuu cagcacgagg gauuuugcug    540

agcuuuacaa ucugggaccu ccgguggccg cugucuacuu caacugccag agggagagcg    600

gauccggcgg aaggccuguc agacgaugau ccauacaugc uuaauuugau aucaaauuac    660

acacacacac acacacacac acacacacac acacacacac acacacacac acuauuuaua    720

uauauauaua uauauauaua uauau                                          745
```

<210> SEQ ID NO 14
<211> LENGTH: 534
<212> TYPE: RNA
<213> ORGANISM: Lycopersicon esculentum

<400> SEQUENCE: 14

```
augccuagag aacgugaucc ucuuguuguu ggucgugugg uaggggaugu auuggacccu     60

uucacaagaa cuauuggccu aagaguuaua uauagagaua gagaaguuaa uaauggaugc    120

gagcuuaggc cuucccaagu uauuaaccag ccaaggguug aaguuggagg agaugaccua    180

cguaccuuuu ucacuuuggu uaugguggac ccugaugcuc caaguccgag ugauccaaau    240

cugagagaau accuucacug guuggucacc gauauuccag cuaccacagg uucaaguuuu    300

gggcaagaaa uagugagcua ugaaagucca agaccaucaa ugggaauaca ucgauuugua    360

uuuguauuau ucagacaauu aggucggcaa acaguguaug cuccaggaug gcgucagaau    420

uucaacacaa gagauuuugc agaacuuuau aaucuugguu uaccuguugc ugcugucuau    480

uuuaauuguc aaagagagag uggcaguggu ggacguagaa gaucugcuga uuga          534
```

<210> SEQ ID NO 15
<211> LENGTH: 525
<212> TYPE: RNA
<213> ORGANISM: Populus tremula

<400> SEQUENCE: 15

```
augucaaggg acagagaucc ucugagcguu ggccguguua uaggggacgu gcuggacccc     60

uucacaaagu cuaucccgcu cagggucacc uacaacucca gagaggucaa caaugguugc    120

gagcucaaac ccucucaggu ugccaaccag ccgaggguug auauuggcgg ggaagaucua    180

aggaccuucu acacucuggu uaugguggac ccugaugcac ccagcccaag ugaccccagc    240

cucagagaau auuugcauug guuggugacu gauauuccag caacaacggg ggcaagcuuu    300

ggccaugaaa cugugugcua ugagagcccg aggccgacga uggggauuca ucgguuuguu    360

uucgucuugu uccggcaacu gggcaggcaa acuguguaug ccccugggug gcgccagaac    420
```

uucaacacca gagacuuugc ugaggucuac aaucuuggau cgccgguggc ugcuguuuau 480
uucaacugcc agagggagag uggcucuggu gguaggaggc gauaa 525

<210> SEQ ID NO 16
<211> LENGTH: 534
<212> TYPE: RNA
<213> ORGANISM: Hordeum vulgare

<400> SEQUENCE: 16
auggccggga gggacaggga uccgcugguu gucggcaggg uugugggga cgugcuggac 60 cccuucgucc gaaccaccaa ccucagggug accuucggga acagggccgu guccaacggc 120
ugcgagcuca agccguccau ggucgcccag cagccgaggg uggaggugg cggcaaugag 180 augaggaccu ucuacacgcu cgugauggua gacccagaug cuccaagucc uagcgacccc 240
aaccuuagag aguaucucca cugguuggug acagauaucc cggguacaac uggggcgucg 300
uucgggcagg aggugaugug cuacgagagc ccucguccaa ccauggggau ccaccgcuuc 360
gugcucgugc ucuuccagca gcuggggcgg cagacggugu acgcccccgg guggcgccag 420
aacuucaaca ccagggacuu ugccgagcuc uacaaccucg gccagcccgu ugccgccguc 480
uacuucaacu gccagcgcga ggccggcucc ggcggcagga ggauguacaa uuga 534

<210> SEQ ID NO 17
<211> LENGTH: 537
<212> TYPE: RNA
<213> ORGANISM: Hordeum vulgare

<400> SEQUENCE: 17
auggugggga gcagcaugca gcgcggggac ccgcuggugg uggggcgggu gaucggcgac 60
gugguggacc cguucgugcg gcggguggcg cugcgggucg gcuacgcguc cagggacgug 120
gccaacggcu gcgagcuccg gccguccgcc aucgccgacc agccgcgcgu cgaggucggc 180
ggcccggaca ugcgcaccuu cuacacccug gugauggugg auccggaugc uccaagcccc 240
agcgacccca gccuuaggga guacuugcac uggcugguca ccgacauccc ggccacgaca 300
ggagugucuu uugguaccga gguugugugc uacgagggcc cgcggccggu gcucgggauc 360
caccgacugg uguuccugcu cuuccagcaa cucggccgac agacggugua cgccccgggg 420
uggcggcaga acuucagcac ccgcgacuuu gccgagcucu acaaccucgg ccugcccguc 480
gccgccgucu acuucaacug ccagagggag accggaaccg gcgggagaag gauguga 537

<210> SEQ ID NO 18
<211> LENGTH: 847
<212> TYPE: RNA
<213> ORGANISM: Oryza sativa

<400> SEQUENCE: 18
ugcaccacac acaguucagc uagcagauca ccuagcuaga uagcugccuc uaucacagua 60
uauuugcucc cugcaacuug cugcugcugc aauagcuagc agcugcagcu aguaagcaaa 120
acuauaaacc uucaggguuu uuugcaagau cgauggccgg aaguggcagg gacagggacc 180
cucuuguggu ugguagggiuu gugggugaug ugcuggacgc guucguccgg agcaccaacc 240
ucaaggucac cuauggcucc aagaccgugu ccaauggcug cgagcucaag ccguccaugg 300
ucacccacca gccuaggguc gaggucggcg gcaaugacau gaggacauuc uacacccuug 360
ugaugguaga cccagaugca ccaagcccaa gugacccuaa ccuuagggag uaucuacauu 420

```
gguuggucac ugauauuccu gguacuacug cagcgucauu ugggcaagag gugaugugcu    480
acgagagccc aaggccaacc auggggaucc accggcuggu guucgugcug uuccagcagc    540
uggggcguca gacaguguac gcgcccgggu ggcgucagaa cuucaacacc aaggacuucg    600
ccgagcucua caaccucggc ucgccggucg ccgccgucua cuucaacugc cagcgcgagg    660
caggcuccgg cggcaggagg gucuaccccu agcuaacgau gaucccgauc gaucugcugc    720
augcucacua ucaucaucca gcaugcuaua cauugcaggu ucagacaauu gaaaugauuc    780
ucgacacaca acauauauau gaugguguaa uuaauuaugc aauuaaauag cugagcaagg    840
cuaaggu                                                               847
```

<210> SEQ ID NO 19
<211> LENGTH: 866
<212> TYPE: RNA
<213> ORGANISM: Oryza sativa

<400> SEQUENCE: 19

```
ccugucacug uuuggcuagc uuaaccuucc ugacaucuau ccucuggauu gaacggcagg     60
agauaccuaa gcuagcuagc aaucucuauc gaucuguuug uuuacauguu caguuaaagg    120
uuacugagaa augccuagag uuuuuccggc uagcuucaua aguuaguggg uuagcugacc    180
uagauucaaa gucuaauccu uuuauuuauu ugauauuaga uauccuaacg uuuuuaguua    240
gagguuauua auuugacaug gccggcagcg gcagggacga uccucuugug guuggcagga    300
uugugggua ugugcuggau ccauucgucc ggaucacuaa ccucaguguc agcuauggug    360
caaggaucgu cuccaauggc ugcgagcuca agccguccau ggugacccaa cagcccaggg    420
ucguggucgg uggcaaugac augaggacgu ucuacacacu cgugauggua gacccggaug    480
cuccgagccc aagcaacccu aaccuuaggg aguaucuaca cuggcugguc accgauauuc    540
cugguaccac uggagcaaca uuugggcaag aggugaugug cuacgagagc ccaaggccaa    600
ccauggggau ccaccggcug guguucgugc uguuccagca gcuggggcgu cagacggugu    660
acgcaccggg guggcgccag aacuucagca ccaggaacuu cgccgagcuc uacaaccucg    720
gcucgccggu cgccaccguc uacuucaacu gccagcgcga ggccggcucc ggcggcagga    780
gggucuaccc cuagcuagcu acgcaugcca cccggccucc augcaugcag cagcuauagc    840
uaagcugaga ccugccuagc uguaua                                          866
```

<210> SEQ ID NO 20
<211> LENGTH: 848
<212> TYPE: RNA
<213> ORGANISM: Ipomoea nil

<400> SEQUENCE: 20

```
cacacacaca cacauauaua uacagagaaa gguuaguuuu gaucgaggag cugagcuagc     60
uaggaugcga aggggaacag uagacccuuu ggugguuggg cgugugaucg gagacguugu    120
ggauccauuc acgagguccg uugagcuuag ggugguuuac aauaacgagg uggauaucag    180
gaaugggugu gagaugaggc cuucucagcu caucaaccca ccuaggguug aaaucggcgg    240
acacgaucuc cguacuuucu acacucuggu uaugguggau ccugaugcuc caaguccaac    300
cucuccaacc cugagggaau accuccacug guuggucacu gauauaccag gaacuacagg    360
agcaagcuuc ggcaaugaag cgauauucua cgagccucca aggccgucaa ugggaaucca    420
ccguuuugug uuugugcuuu uccggcaacu uggccggcag acaguuuaug caccgguuug    480
gcgccagaau uucaacacuc gaaacuuugc ugagauuuac aaucuugguu ugccaguggc    540
```

```
cgucacuuac uuuaacggcc aaagggaggg uggcaccggc ggucgaucuc cggcagagcc    600

cugggcagcc gauuaauuac ccugcuccuu cccguuaauu ucaugcaugc augcaugcua    660

ucuauagcau aacauacaua uaguauauau cauaaauaaa uaagaccaca ugcauuaaca    720

uguuuaauuu ucccaugaau auauguuaaa guuguucuag aagaacuacg uacuccauua    780

uauuacccuu uauauauggc aaugaagaug guuucaucuc uauuuagaag cuaaaaaaaa    840

aaaaaaaa                                                             848
```

```
<210> SEQ ID NO 21
<211> LENGTH: 798
<212> TYPE: RNA
<213> ORGANISM: Arabidopsis thaliana

<400> SEQUENCE: 21

uuuauugaga uacuugagau ccaagauaaa uaugucuuua gucguagaga uccucuugug     60

gucggcagug uuguuggaga uguucuugau ccuuucacga gguuggucuc ucuuaagguc    120

acuuauggcc auagagaggu uacuaauggc uuggaucuaa ggccuucuca aguucugaac    180

aaaccaauag uggagauugg aggagacgac uucagaaauu ucuacaccuu gguuauggug    240

gauccagaug ugccgagucc aagcaacccu caccaacgag aauaucucca cugguuggug    300

acugauauac cugccaccac uggaaaugcc uuuggcaaug agguggugug cuacgagagu    360

ccacgucccc ccucgggaau ucaucguauu guguugguau uguuccggca acucggaaga    420

caaacgguuu augcaccggg guggcgccaa caguucaaca cucgugaguu ugcugagauc    480

uacaaucuug gucuuccugu ggcugccucu uacuucaacu gccagaggga gaauggcugu    540

gggggaagaa gaacguagau gcguaccuac uuacguuaac uaauaaucua aucguauaau    600

auucccuuaa ugaaguauuu aagcaucuau gucaauguaa uaagaauuua aagauacgag    660

cuaaaaaaaa ugaugcauau gcugacaucg auguaaagua guuuacacuu uuaauguaau    720

aacuagguuu uaacccgcgg uacaccgcga gacuauuuug uuuuuuuaag aauaaaaaua    780

uaauuuguuu agucgauu                                                  798
```

```
<210> SEQ ID NO 22
<211> LENGTH: 519
<212> TYPE: RNA
<213> ORGANISM: Glycine max

<400> SEQUENCE: 22

auggcacggg agaacccucu uguuauuggu ggugugauug gggauguucu caacccuuuu     60

acaagcuccg uuucuuugac uguuucaauc aauaauaggg cgauuagcaa uggcuuggaa    120

cucaggcccu cucaaguugu uaaucgcccu aggguuacug uuggugguga agaccuaagg    180

accuucuaca cucugguuau gguggaugca gaugcaccua gcccuagcaa cccugucuug    240

agggaauacc uucacuggau ggugacagau auuccagcua ccacaaaugc aagcuuuggg    300

agagagguug uguuuuauga gagcccgaac ccuucaguag ggauucaucg aaucguguuc    360

guauuguucc agcaauuggg cagagacacu gucaucaccc cagaauggcg ccauaauuuc    420

aauuccagaa acuuugcuga aauuaauaac cuugcaccug uugcagcagc uuaugccaac    480

ugccaaagag agcgugguug cgguggaagg agauauuaa                           519
```

```
<210> SEQ ID NO 23
<211> LENGTH: 901
<212> TYPE: RNA
```

<213> ORGANISM: Zea mays

<400> SEQUENCE: 23

```
agagcacauc cguagugugu gcaugcauca cagucacaca cacacagcag aagaagaaga     60
aaccgaacga ggguuuagcu agcaaaauaa acagaagcaa gcaagcuagc uagagcuaag    120
gaucgagauc gagaucgacc gaccgacgac gaucagcuag cauggcgcgc uucguggauc    180
cgcugguggu ggggcgggug aucggcgagg ugguggaccu guucgugccu uccaucucca    240
ugaccgucgc cuaugauggc cccaaggaca ucagcaacgg cugccuccuc aagccguccg    300
ccaccgccgc gccgccgcuc guccgcaucu ccggccgccg caacgaccuc uacacgcuga    360
ucaugacgga ccccgaugcg ccuagcccca gcaacccgac caugagggag uaccuccacu    420
ggauagugau uaacauacca ggaggaacag augcuacuaa aggugaggag gugguggagu    480
acaugggccc gcggccgccg gugggguaucc accgcuacgu gcuggugcug uucgagcaga    540
agacgcgcgu gcacgcggag gcccccggcg accgcgccaa cuucaagacg cgcgcguucg    600
cggcggcgca cgagcucggc cuccccacug ccgucgucua cuucaacgcg cagaaggagc    660
ccgccagccg ccgccgcuag cuagcagcuc cucucugagg caugccagau gcaugcgugu    720
gcgugcaggu gcaaccaccg cacugccggc ggcuacguau gaccggugaa uaaaaaguuu    780
uacugcaccg uaagcaugcu cgcccuguug cuauugguau auguuagcag uguggcaguc    840
uguauguagu agcuauucgc uugcaucuau gcacucuaug uuaguaugcg uacguguggu    900
u                                                                    901
```

<210> SEQ ID NO 24
<211> LENGTH: 1069
<212> TYPE: RNA
<213> ORGANISM: Zea mays

<400> SEQUENCE: 24

```
uggcaaaaac ccagcgcuuu gugccgccgc cguccgccgg ccccucugcc cuuguacgcg     60
caccuagaca caucgucauc gaucaucaca cgcaaucgac acaagaaguu aauaaaacagc   120
ccaaggacgc agagaucagc ugaucgagaa ggacuuguac uacuacucag uauugucguc    180
acaugcacau auauguacau aaagagcuag cuaccugagc ucuacccaag gucgcguuga    240
ucgaucgauc auggcgcggu ucguggaccc gcugguggug gggcggguga ucggcgaggu    300
gguggaccug uucgugcccu ccgucuccau gaccgucgcc uauggcccca aagacaucag    360
caacggcugc cuccucaagc cguccgccac cgccgcgccg ccgcucgucc gcaucuccgg    420
ccgccgcgac gaccucuaca cgcugaucau gacggaccca gaugcgccua gccccagcga    480
cccgaccaug agggaguacc uccacuggau agugacuaac auaccaggag gaacggaugc    540
aaacaaaggu gaggaggugg uggaguacau gggcccgcgg ccgccggucg gaauccaccg    600
cuacgugcug gugcuguucg agcagaagac gcgugugcac gcggaggguc ccggugagcg    660
cgccaacuuc aacacacgcg cguucgcggc ggcgcacgag cucggccucc ccaccgccgu    720
cguguacuuc aacgcgcaga aagagccggc caaccaccgc cgccgcuagc uaguagcucc    780
aacaagggcg cgccagcuga gcugcgugcg ugcaacccac cacacagccg ccggcgaagg    840
cugccuauau gaccggcgaa uaaaaagucu uacugcaccg uccguaagcg uacucucugu    900
ugguauaugc uugucuucag gcucuugagu cuaucuacuu aaaugugguu accacugagu    960
aauagaagca guuggcgcuu cgaucgauca uucuaauauc cguacguguc aaucauuccu   1020
guuuccauca ucuugcauuu gaagacgcau ugguucuaca ccaaggugu               1069
```

<210> SEQ ID NO 25
<211> LENGTH: 1288
<212> TYPE: RNA
<213> ORGANISM: Cucurbita maxima

<400> SEQUENCE: 25
gacuuuuuau ucaacaaucu cucucucucu cucucaacuu ccgaucaagu cucuccgccg 60
ucuuuucacc ggagcugaca auuccgauca uuuuuugcuu cccuuaaauu uccggcaugg 120
aggaaccacc gccaaacgcc uuggauuugc ccccuggcuu cagauuccac cccaccgacg 180
aggagaucgu cacuuauuac cugauacaua agaucaccga cgccgccuuc acugccaccg 240
ccaucggaga agcugaccug aauaagugug aaccuuggga uuugccacau aaagcuaaga 300
ugggggaaaa agaaugguau uuuuuuugcc agagagaccg gaaauauccg accgggauga 360
gaacgaaccg ggcgacucag accgguuacu ggaaagcgac cgggaaagac aaggagauuc 420
ucaagggaag aacgguucug gcugguauga agaaaacgcu gguuuuuuac aaaggaagag 480
cucccaaagg ugaaaagacc aauuggguca ugcaugaauu ucgacucgaa cccaaauucu 540
uucaguuucu ugguuuuccc aagcccauua aggcugauug gguuguaugu cggguuuuuc 600
acaagaacac aacgaacacg gucggaguag ugaaaaagau ucaaacuucu gauuuuucuu 660
cuucucuccc accucuaaua gaucccacaa cugcucauac uccaaucagu ggcagauucg 720
auaaauggug agucaacugg agguuaucag uaccauucga uaauuaugca aaugauuacc 780
auuaucaucg gccuuuuuca gcgacgaaua cugcagugac aaugauuucg ucguacccau 840
cgucuguccc cgacgacgaa uucuucucau uugaucaacu agacgucggu ggaacaaugu 900
caauggcggc ggcgacgaca acaacaacaa caacuaugga gugcaaaaua gaacaaguuu 960
cauggucaac gaugagcggu gugacaccgg agauaucauc gucgauugac aacgaggcag 1020
cucucgaguu cugggacuac ugaaaauuga aaguagaugu uaugaucgaa caauggcgau 1080
gcuuuguuuu aaaugggcau uucccauauu gaacguuuaa acaaugauua auugauugcu 1140
aauuauuauu auuuuuuuuu uuugguuaca uaguccuuuu ugggaaggaa uauuagaacu 1200
uucauggguu ugguuuguug auuguauuga uauguagcaa ugugacauug uauauagcuu 1260
cuuuaucuuu uauuuuaacc guugcaaa 1288

<210> SEQ ID NO 26
<211> LENGTH: 1964
<212> TYPE: RNA
<213> ORGANISM: Arabidopsis thaliana

<400> SEQUENCE: 26
uaauaaucau uuuuuuucuu auaaccuucc ucucuauuuu uacaauuuau uuuguuauua 60
gaagugguag uggagugaaa aaacaaaucc uaagcagucc uaaccgaucc ccgaagcuaa 120
agauucuuca ccuucccaaa uaaagcaaaa ccuagauccg acauugaagg aaaaaccuuu 180
uagauccauc ucugaaaaaa aaccaaccau gaagagagau caucaucauc aucaucaaga 240
uaagaagacu augaugauga augaagaaga cgacgguaac ggcauggaug agcuucuagc 300
uguucuuggu uacaagguua ggucaucgga aauggcugau guugcucaga aacucgagca 360
gcuugaaguu augaugucua auguucaaga agacgaucuu ucucaacucg cuacugagac 420
uguucacuau aauccggcgg agcuuuacac guggcuugau ucuaugcuca ccgaccuuaa 480
uccuccgucg ucuaacgccg aguacgaucu uaaagcuauu cccggugacg cgauucucaa 540

```
ucaguucgcu aucgauucgg cuucuucguc uaaccaaggc ggcggaggag auacguauac    600
uacaaacaag cgguugaaau gcucaaacgg cgucguggaa accaccacag cgacggcuga    660
gucaacucgg cauguugucc ugguugacuc gcaggagaac ggugugcguc ucguucacgc    720
gcuuuuggcu ugcgcugaag cuguucagaa ggagaaucug acuguggcgg aagcucuggu    780
gaagcaaauc ggauucuuag cuguuucuca aaucggagcu augagaaaag ucgcuacuua    840
cuucgccgaa gcucucgcgc ggcggauuua ccgucucucu ccgucgcaga guccaaucga    900
ccacucucuc uccgauacuc uucagaugca cuucuacgag acuuguccuu aucucaaguu    960
cgcucacuuc acggcgaauc aagcgauucu cgaagcuuuu caagggaaga aaagaguuca   1020
ugucauugau uucucuauga gucaaggucu ucaauggccg gcgcuuaugc aggcucuugc   1080
gcuucgaccu gguggucuc cuguuuuccg guuaaccgga auugguccac cggcaccgga   1140
uaauuucgau uaucuucaug aaguugggug uaagcuggcu cauuuagcug aggcgauuca   1200
cguugaguuu gaguacagag gauuuguggc uaacacuuua gcugaucuug augcuucgau   1260
gcuugagcuu agaccaagug agauugaauc uguugcgguu aacucuguuu ucgagcuuca   1320
caagcucuug ggacgaccug gugcgaucga uaagguucuu ggugugguga aucagauuaa   1380
accggagauu uucacugugg uugagcagga aucgaaccau aauaguccga uuuucuuaga   1440
ucgguuuacu gagucguugc auuauuacuc gacguuguuu gacucguugg aaggugugacc  1500
gaguggucaa gacaagguca ugucggaggu uuacuugggu aaacagaucu gcaacguugu   1560
ggcuugugau ggaccugacc gaguugagcg ucaugaaacg uugagucagu ggaggaaccg   1620
guucgggucu gcuggguuug cggcugcaca uauugguucg aaugcguuua agcaagcgag   1680
uaugcuuuug gcucuguuca acggcgguga ggguuaucgg guggaggaga gugacggcug   1740
ucucauguug gguuggcaca cacgaccgcu cauagccacc ucggcuugga aacucuccac   1800
caauuagaug guggcucaau gaauugaucu guugaaccgg uuaugaugau agauuuccga   1860
ccgaagccaa acuaaauccu acuguuuuuc ccuuugucac uuguuaagau cuuaucuuuc   1920
auuauauuag guaauugaaa aauuucuaaa uuacucacac uggc                    1964
```

```
<210> SEQ ID NO 27
<211> LENGTH: 1556
<212> TYPE: RNA
<213> ORGANISM: Lycopersicon esculentum

<400> SEQUENCE: 27

aaagaaaaaa ggaauauugu guguuugcuu uuuuuucuga cuaguaguau ugcuaacuau     60
guauuccauu aaggauuugc ugugaaaaag ccugauauca guaagcauaa aacucgggag    120
aucacuuaca cacacacaca cccuccuaaa aaagagaaga gagauuuacu guuaaacaga    180
gguuuuuuuc cauuucuuuu uuuuuuucag ugugugugug agagaaagag augauuuuca    240
uaggcacaaa caaauagaaa ggaacaaaau uuagagugaa gaagaaagug ugugagagaa    300
uaauggaggg ugguucuagu ggaaauacua guacaucuug uuuaaugaug augggauaug    360
gagaucauga aaacaacaac aacaacaaug gaaaugguaa uggaaaugga aauggaaaug    420
uaacaauuug ugcuccucca augaugauga ugaugccucc uccuccuccu ucuuuaacua    480
acaauaacaa ugcagaaaca agcaacaaca acauccuuuu ucuuccuuuc auggacaaca    540
acaacaacaa uaauccucaa gaagacaaca acucuucuuc uucuuccauc aagucaaaga    600
uuauggcuca uccucacuac caucgucucu ugacugcuua ucucaauugu caaaagauag    660
gagcuccgcc agaaguggug gcaaggcuag aggaaauaug ugccacguca gcaacaaugg    720
```

gccguagcag uaguaguagu gguggugga a ucauuggaga agauccugca cuagaucagu 780
ucauggaggc uuauugugag augcugacaa aauaugaaca agaacucuca aaacccuuca 840
aggaagccau gguuuuucuu ucaagaauug agugucaguu caaagcuuua acucuugcac 900
cuaauucuuc ucaugaaucu gcuuugggcg aggcaaugga uagaaaugga ucaucugaug 960
aagagguuga cgugaauaac aguuucaucg acccccaggc ugaggauaga gagcucaaag 1020
gucaauuguu gcguaaguac agcgguuacu ugggaagccu uaagcaggag uucaugaaga 1080
agaggaagaa aggcaagcug ccuaaggaag caaggcaaca auugguggau ugguggcuua 1140
gacauauuaa auggccauau ccaucggaau cucagaagcu ugcacuagcu gaaucaacgg 1200
gauuggacca gaagcaaaua aacaacuggu uuaucaauca aagaaagagg cauuggaaac 1260
caucagaaga uaugcaguuu guugugaugg augcugcuca uccacauuac uauauggaua 1320
auguucuugc uaaccauuuc ccaauggaua ugacacccuc ucuccucuga auuaagauuu 1380
gucauuauua auaucaagga uguuuaauua auuugcauau uacuugugug cauguaguag 1440
uacaagcuau ugugacacaa ucaacuuuuu auuagaccaa auauauaaag ugcuuguaau 1500
agaucuuucu auuaucaucu uuaauuaugg aauuaaauag uuuguacuug cuaaaa 1556

<210> SEQ ID NO 28
<211> LENGTH: 2735
<212> TYPE: RNA
<213> ORGANISM: Solanum tuberosum

<400> SEQUENCE: 28
caugcagaga uaaaaauaua gaucagucug acaagaaggc aacuucucaa agcuuagaga 60
gcuaccaccc gaagauagac aguuaguuac auguacuguu auagauaaaa ggagaaaucc 120
gaagaagaaa gaauuuuuuu ugcagauaug uacuaucaag gaaccucgga uaauacuaau 180
auacaagcug aucaucaaca acgucauaau caugggaaua guaauaauaa uaauauucag 240
acacuuuauu ugaugaaccc uaacaauuau augcaaggcu acacuacuuc ugacacacag 300
cagcagcagc aguuacuuuu ccugaauucu ucaccagcag caagcaacgc gcuuugccau 360
gcgaauauac aacacgcgcc gcugcaacag cagcacuuug ucggugugcc ucuuccggca 420
guaaguuugc acgaucagau caaucaucau ggacuuuuac agcgcaugug gaacaaccaa 480
gaucaaucuc agcaggugau aguaccaucg ucgacggggg uuucugccac gucauguggc 540
gggaucacca cggacuuggc gucucaauug gcguuucaga ggccgauucc gacaccacaa 600
caccgacagc agcaacaaca gcaaggcggu cuaucucuaa gccuuucucc ucagcuacaa 660
cagcaaauua guuucaauaa caauauuuca uccucaucac caaggacaaa uaauguuacu 720
auuaggggaa cauuagaugg aaguucuagc aacaugguuu uaggcucuaa guaucugaaa 780
gcugcacaag agcuucuuga ugaaguuguu aauauuguug gaaaaagcau caaaggagau 840
gaucaaaaga aggauaauuc aaugaauaaa gaaucaaugc cuuuggcuag ugaugucaac 900
acuaauaguu cuggguggugg ugaaaguagc agcaggcaga aaaaugaagu ugcuguugag 960
cuuacaacug cucaaagaca agaacuucaa augaaaaaag ccaagcuucu ugccaugcuu 1020
gaagaggugg agcaaaggua cagacaguac caucaccaaa ugcaaauaau uguauuauca 1080
uuugagcaag uagcaggaau uggaucagcc aaaucauaca cucaauuagc uuugcaugca 1140
auuucgaagc aauucagaug ccuaaaggau gcaauugcug agcaaguaaa ggcgacgagc 1200
aagaguuuag gugaagagga aggcuuggga gggaaaaucg aaggcucaag acucaaauuu 1260

```
guggaccauc aucuaaggca acaacgcgcg cugcaacaga uaggaaugau gcaaccaaau   1320

gcuuggagac cccaaagagg uuuaccugaa agagcugucu cuguccuucg ugcuuggcuu   1380

uucgagcauu uucuucaucc uuacccaaag gauucagaca aaaucaugcu ugcuaagcaa   1440

acggggcuaa caaggagcca ggugucuaac ugguucauaa augcucgagu ucgauuaugg   1500

aagccaaugg uagaagaaau guacuuggaa gaagugaaga aucaagaaca aaacaguacu   1560

aauacuucag gagauaacaa aaacaaagag accaauauaa gugcuccaaa ugaagagaaa   1620

cauccaauua uuacuagcag cuuauuacaa gaugguauua cuacuacuca agcagaaauu   1680

ucuaccucaa cuauuucaac uuccccuacu gcaggugcuu cacuucauca ugcucacaau   1740

uucuccuucc uugguucauu caacauggau aauacuacua cuacuguuga ucauauugaa   1800

aacaacgcga aaaagcaaag aaaugacaug cacaaguuuu cuccaaguag uauucuuuca   1860

ucuguugaca uggaagccaa agcuagagaa ucaucaaaua aaggguuuac uaauccuuua   1920

auggcagcau acgcgauggg agauuuugga agguuugauc cucaugauca acaaaugacc   1980

gcgaauuuuc auggaaauaa uggugucucu cuuacuuuag gacuucccuc uucugaaaac   2040

cuagccaugc cagugagcca acaaaauuac cuuucuaaug acuugggaag uaggucugaa   2100

auggggaguc auuacaauag aaugggauau gaaaacauug auuuucagag ugggaauaag   2160

cgauuuccga cucaacuauu accagauuuu guuacaggua aucuaggaac augaauacca   2220

gaaagucucg uauugauagc ugaaaagaua aaaggaaguu agggauacuc uuauauugug   2280

ugaggccuuc uggcccaagu cggaggaccc aauuugauac aaccuaucau aggagaaaag   2340

aaguggagac uaaauuaaag uaacaaaauu uuaaagcaca cuuucuagua uauauacuuc   2400

uuuuuuuuau aguauagaaa agaagagauu uugugcuuua guguauagau agagucuacu   2460

uaguauaggu uauacuucua guuccuugag aagauugaua caacuaguag uauuuuuuuu   2520

cuuuuggguu ggcuuggagu acuauuuuaa guuauuggaa acuagcuaua guaaauguug   2580

uaaaguugug auauuguucc ucucaauuug cauauaauuu gaaauauuuu guaccuacua   2640

gcuagucucu aaauuauguu uccauugcuu guaauugcaa uuuuauuuga auuuugugcu   2700

aucauuauua gauuagcaaa aaaaaaaaaa aaaaa                              2735
```

<210> SEQ ID NO 29
<211> LENGTH: 72
<212> TYPE: RNA
<213> ORGANISM: Arabidopsis thaliana

<400> SEQUENCE: 29

```
aucagagugg cgcagcggaa gcgugguggg cccauaaccc acaggUccca ggaucgaaac     60

cuggcucuga ua                                                        72
```

<210> SEQ ID NO 30
<211> LENGTH: 71
<212> TYPE: RNA
<213> ORGANISM: Arabidopsis thaliana

<400> SEQUENCE: 30

```
gcaccagugg ucuaguggca ugauaguacc cugccacggu acagacccgg guucaauucc     60

cggcuggugc a                                                         71
```

<210> SEQ ID NO 31
<211> LENGTH: 699
<212> TYPE: DNA
<213> ORGANISM: Cucurbita maxima

<400> SEQUENCE: 31

```
ggggcttcaa aagagaatta ggtcacctcc cagctcggtt tcgacacgcc atgccgagaa     60
atcgtgaccc tctagtcgtc gggagagtga tcggcgacgt cgtcgactcg ttctcgaggt    120
ccatctcgat tagggttgtt tacgactcga gggaagttaa caatgggtgt gagctcaaac    180
cctctcaagc tgtcaacaag ccaagagttg agattggtgg cactgacctt cgcaccttct    240
tcactttggt tatggtggat cccgacgctc ctagccctag cgatcccaat ctaagagaat    300
acttgcattg gttagtgacc gatattccag ctacaaccga ggcaaccttt ggacaagaga    360
tagtgtgcta cgagaatcca agaccaacgg tgggtatcca ccgttttgtg ctggtcttgt    420
tccggcagct cggaaggcaa acggtgtatg ctcctgggtg gcgccagaac ttcaacacca    480
gacactttgc agagctttac aatcttggtt cgccagtcgc cgccgtctat ttcaattgcc    540
aaagggaaaa tggctccggt ggaaggagaa gagccggcga tgaatgttca taaaaacact    600
tcacttcaca ttatattatc aaccaatata ttgtaataac atggttcacg tttctatcta    660
atagattata tatttttaat aagttcgtga aaaaaaaaa                           699
```

<210> SEQ ID NO 32
<211> LENGTH: 858
<212> TYPE: DNA
<213> ORGANISM: Cucurbita maxima

<400> SEQUENCE: 32

```
gagacaatta cgcatctttt cagctctctc acgtactacc atcctctcga cgccatgccg     60
agagaccgtg accctttggt cgttgggaga gtcatcggcg acgttatcga ctcgttcacg    120
aagtccattt cgattagggc tacttacaac aacagggaaa ttagcaatgg ctgtgagctc    180
aaaccctctc aagttgtcaa ccagccaaga gttgagattg gtggcactga ccttcgcacc    240
ttcttcactt tggttatggt ggatcctgat gctcctagcc ctagtgatcc taatctaagg    300
gaatacttgc attggttggt gactgatatc ccagctacaa ctggagcgaa ctttggtcaa    360
gagatcgtgt gctatgagag cccaagaccc acggtgggta tccatcgtct tgtgctggtg    420
ttgtttcgac agcttggaag gcaaacggtg tacgctcctg ggtggcgcca gaacttcaac    480
acaagagact ttgcagagct ttacaatctt ggcttgccgg tggcagccgt ttatttcaat    540
tgccaaaggg aaagtgggtc tggtggaagg agaagaaccc aagatgattt ctaagcccca    600
cttcacatta attagattaa tattatagcc cctatcatct attaatccta ccttgctttt    660
agattaacct ttattttgag tacacccatg gatcataaat aagcccaaaa tgcattccta    720
atattgctct tatactcgtt tcgtatgaat cactgtcttt tcttctttgt ttttcttgtt    780
cgagtgttca tgttgtgctt ttttttcgt atgaatcaaa gtagaagatc aagattcgaa     840
aaaaaaaaaa aaaaaaaa                                                  858
```

<210> SEQ ID NO 33
<211> LENGTH: 596
<212> TYPE: DNA
<213> ORGANISM: Vitis vinifera

<400> SEQUENCE: 33

```
ccctcttgta ttgtatcggt gaggtgtgtg tgatgcctag ggaaagggat cctcttgttg     60
ttgggcgcgt tgtcggggat gttctggacc cctttctcag gtccatcact ctgagggtga    120
cctacaataa tagagaagta gcaaatggct gtgagttcag accctctcag ctagtcagcc    180
```

```
aacctagggt ggacattgga ggggatgact tgaggacctt ctatactttg gttatggtgg    240
accctgacgc tccaagcccc agtaatccga acctaaggga gtacttacat tggttggtga    300
ctgatattcc agcaactact ggggcaaact tcggccaaga gattgtgtgt tatgagagcc    360
cacgcccaac agctgggatt catcgctttg tttttgtatt gtttcgccaa ctgggtaggc    420
agacagtgta tgcaccaggg tggcgccaaa atttcaacac tagggacttt gctgagcttt    480
ataatcttgg tttgcctgtt gctgctgttt attttaactg ccaaagggag ggcggctcgg    540
gtggtcgaag atcataatca atggattttg tacgcaacct tgcgacttac aaaggc        596
```

<210> SEQ ID NO 34
<211> LENGTH: 525
<212> TYPE: DNA
<213> ORGANISM: Malus domestica

<400> SEQUENCE: 34

```
atgcctaggg atagggaccc ccttgttgtt ggacgagtgg ttggtgatgt tttagacccc     60
ttcacaaggt ctgtttctct gagggtgacc tacggtacta aggaggttaa caatggttgt    120
gagctcaaac cttctgaagt tgtccaacaa cctagagctg atattggtgg agacgatctc    180
aggactttct acactctggt catggtggat cctgatgcac ccagcccaag tgaccccaac    240
ctaaaggaat atttgcattg gttggttacc gatattccag caactactgc ggcaagcttc    300
gggcaagaga tcgtgtgtta tgaaagtcca cggccaacag tggggattca tcgctttgtt    360
ttggtggtgt ttcgccaatt gggtaggcaa acggtgtatg ctccgggatg gcgccagaac    420
ttcaatacca gagacttcgc cgagctttat aatcttggat taccggtgtc tgtcgtctat    480
tttaactgcc aaagggaggg cggctccggt ggaaggagaa gataa                    525
```

<210> SEQ ID NO 35
<211> LENGTH: 745
<212> TYPE: DNA
<213> ORGANISM: Citrus unshiu

<400> SEQUENCE: 35

```
ggcacgagga atagtcttac tacttttgta ggctgtgtgt gtatttgttt gtgcttagtg     60
ttgttgagtg tttgtttgtg tttagtgttg ttgatatgtc tagcagggag agagatcctc    120
ttattgttgg ccgcgttgtt ggtgatgttc ttgacaattt tacaagaaca attccaatga    180
ggattaccta ttcaaacaag gatgttaata atggccgtga gctcaaacct tctgaagttc    240
tgaaccagcc tagggctgaa attggtggtg atgatcttag gacattttat actttggtaa    300
tggttgatcc tgatgcacca agcccaagtg accccagcct tagggagtat ttgcattggt    360
tggtgactga tattccagca accacagggg ccagctttgg ccaagagatt gtgaactatg    420
aaagccctag gccaacgatg gggattcaca ggtttgtctt tgtgttgttc cggcaacttg    480
ggaggcagac tgtttatgca ccagggtggc gtcagaactt cagcacgagg gattttgctg    540
agctttacaa tctgggacct ccggtggccg ctgtctactt caactgccag agggagagcg    600
gatccggcgg aaggcctgtc agacgatgat ccatacatgc ttaatttgat atcaaattac    660
acacacacac acacacacac acacacacac acacacacac acacacacac actatttata    720
tatatatata tatatatata tatat                                          745
```

<210> SEQ ID NO 36
<211> LENGTH: 534
<212> TYPE: DNA
<213> ORGANISM: Lycopersicon esculentum

<400> SEQUENCE: 36

```
atgcctagag aacgtgatcc tcttgttgtt ggtcgtgtgg taggggatgt attggaccct     60
ttcacaagaa ctattggcct aagagttata tatagagata gagaagttaa taatggatgc    120
gagcttaggc cttcccaagt tattaaccag ccaagggttg aagttggagg agatgaccta    180
cgtacctttt tcactttggt tatggtggac cctgatgctc caagtccgag tgatccaaat    240
ctgagagaat accttcactg gttggtcacc gatattccag ctaccacagg ttcaagtttt    300
gggcaagaaa tagtgagcta tgaaagtcca agaccatcaa tgggaataca tcgatttgta    360
tttgtattat tcagacaatt aggtcggcaa acagtgtatg ctccaggatg gcgtcagaat    420
ttcaacacaa gagattttgc agaactttat aatcttggtt tacctgttgc tgctgtctat    480
tttaattgtc aaagagagag tggcagtggt ggacgtagaa gatctgctga ttga          534
```

<210> SEQ ID NO 37
<211> LENGTH: 525
<212> TYPE: DNA
<213> ORGANISM: Populus tremula

<400> SEQUENCE: 37

```
atgtcaaggg acagagatcc tctgagcgtt ggccgtgtta taggggacgt gctggacccc     60
ttcacaaagt ctatcccgct cagggtcacc tacaactcca gagaggtcaa caatggttgc    120
gagctcaaac cctctcaggt tgccaaccag ccgagggttg atattggcgg ggaagatcta    180
aggaccttct acactctggt tatggtggac cctgatgcac ccagcccaag tgaccccagc    240
ctcagagaat atttgcattg gttggtgact gatattccag caacaacggg ggcaagcttt    300
ggccatgaaa ctgtgtgcta tgagagcccg aggccgacga tggggattca tcggtttgtt    360
ttcgtcttgt tccggcaact gggcaggcaa actgtgtatg cccctgggtg gcgccagaac    420
ttcaacacca gagactttgc tgaggtctac aatcttggat cgccggtggc tgctgtttat    480
ttcaactgcc agagggagag tggctctggt ggtaggaggc gataa                    525
```

<210> SEQ ID NO 38
<211> LENGTH: 534
<212> TYPE: DNA
<213> ORGANISM: Hordeum vulgare

<400> SEQUENCE: 38

```
atggccggga gggacaggga tccgctggtt gtcggcaggg ttgtggggga cgtgctggac     60
cccttcgtcc gaaccaccaa cctcagggtg accttcggga acagggccgt gtccaacggc    120
tgcgagctca agccgtccat ggtcgcccag cagccgaggg tggaggtggg cggcaatgag    180
atgaggacct tctacacgct cgtgatggta gacccagatg ctccaagtcc tagcgacccc    240
aaccttagag agtatctcca ctggttggtg acagatatcc cgggtacaac tggggcgtcg    300
ttcgggcagg aggtgatgtg ctacgagagc cctcgtccaa ccatggggat ccaccgcttc    360
gtgctcgtgc tcttccagca gctggggcgg cagacggtgt acgcccccgg gtggcgccag    420
aacttcaaca ccagggactt tgccgagctc tacaacctcg gccagcccgt tgccgccgtc    480
tacttcaact gccagcgcga ggccggctcc ggcggcagga ggatgtacaa ttga          534
```

<210> SEQ ID NO 39
<211> LENGTH: 537
<212> TYPE: DNA
<213> ORGANISM: Hordeum vulgare

<400> SEQUENCE: 39

```
atggtgggga gcagcatgca gcgcggggac ccgctggtgg tggggcgggt gatcggcgac     60
gtggtggacc cgttcgtgcg gcgggtggcg ctgcgggtcg gctacgcgtc cagggacgtg    120
gccaacggct gcgagctccg gccgtccgcc atcgccgacc agccgcgcgt cgaggtcggc    180
ggcccggaca tgcgcacctt ctacaccctg gtgatggtgg atccggatgc tccaagcccc    240
agcgacccca gccttaggga gtacttgcac tggctggtca ccgacatccc ggccacgaca    300
ggagtgtctt ttggtaccga ggttgtgtgc tacgagggcc cgcggccggt gctcgggatc    360
caccgactgg tgttcctgct cttccagcaa ctcggccgac agacggtgta cgccccgggg    420
tggcggcaga acttcagcac ccgcgacttt gccgagctct acaacctcgg cctgcccgtc    480
gccgccgtct acttcaactg ccagagggag accggaaccg gcgggagaag gatgtga       537
```

<210> SEQ ID NO 40
<211> LENGTH: 847
<212> TYPE: DNA
<213> ORGANISM: Oryza sativa

<400> SEQUENCE: 40

```
tgcaccacac acagttcagc tagcagatca cctagctaga tagctgcctc tatcacagta     60
tatttgctcc ctgcaacttg ctgctgctgc aatagctagc agctgcagct agtaagcaaa    120
actataaacc ttcagggttt tttgcaagat cgatggccgg aagtggcagg gacagggacc    180
ctcttgtggt tggtagggtt gtgggtgatg tgctggacgc gttcgtccgg agcaccaacc    240
tcaaggtcac ctatggctcc aagaccgtgt ccaatggctg cgagctcaag ccgtccatgg    300
tcacccacca gcctagggtc gaggtcggcg gcaatgacat gaggacattc tacacccttg    360
tgatggtaga cccagatgca ccaagcccaa gtgaccctaa ccttagggag tatctacatt    420
ggttggtcac tgatattcct ggtactactg cagcgtcatt tgggcaagag gtgatgtgct    480
acgagagccc aaggccaacc atggggatcc accggctggt gttcgtgctg ttccagcagc    540
tggggcgtca gacagtgtac gcgcccgggt ggcgtcagaa cttcaacacc aaggacttcg    600
ccgagctcta caacctcggc tcgccggtcg ccgccgtcta cttcaactgc cagcgcgagg    660
caggctccgg cggcaggagg gtctacccct agctaacgat gatcccgatc gatctgctgc    720
atgctcacta tcatcatcca gcatgctata cattgcaggt tcagacaatt gaaatgattc    780
tcgacacaca acatatatat gatggtgtaa ttaattatgc aattaaatag ctgagcaagg    840
ctaaggt                                                               847
```

<210> SEQ ID NO 41
<211> LENGTH: 866
<212> TYPE: DNA
<213> ORGANISM: Oryza sativa

<400> SEQUENCE: 41

```
cctgtcactg tttggctagc ttaaccttcc tgacatctat cctctggatt gaacggcagg     60
agatacctaa gctagctagc aatctctatc gatctgtttg tttacatgtt cagttaaagg    120
ttactgagaa atgcctagag tttttccggc tagcttcata agttagtggg ttagctgacc    180
tagattcaaa gtctaatcct tttatttatt tgatattaga tatcctaacg tttttagtta    240
gaggttatta atttgacatg gccggcagcg gcagggacga tcctcttgtg gttggcagga    300
ttgtgggtga tgtgctggat ccattcgtcc ggatcactaa cctcagtgtc agctatggtg    360
caaggatcgt ctccaatggc tgcgagctca agccgtccat ggtgacccaa cagcccaggg    420
```

```
tcgtggtcgg tggcaatgac atgaggacgt tctacacact cgtgatggta gacccggatg    480

ctccgagccc aagcaaccct aaccttaggg agtatctaca ctggctggtc accgatattc    540

ctggtaccac tggagcaaca tttgggcaag aggtgatgtg ctacgagagc ccaaggccaa    600

ccatggggat ccaccggctg gtgttcgtgc tgttccagca gctggggcgt cagacggtgt    660

acgcaccggg gtggcgccag aacttcagca ccaggaactt cgccgagctc tacaacctcg    720

gctcgccggt cgccaccgtc tacttcaact gccagcgcga ggccggctcc ggcggcagga    780

gggtctaccc ctagctagct acgcatgcca cccggcctcc atgcatgcag cagctatagc    840

taagctgaga cctgcctagc tgtata                                         866
```

<210> SEQ ID NO 42
<211> LENGTH: 848
<212> TYPE: DNA
<213> ORGANISM: Ipomoea nil

<400> SEQUENCE: 42

```
cacacacaca cacatatata tacagagaaa ggttagtttt gatcgaggag ctgagctagc     60

taggatgcga aggggaacag tagacccttt ggtgttgggg cgtgtgatcg gagacgttgt    120

ggatccattc acgaggtccg ttgagcttag ggtggtttac aataacgagg tggatatcag    180

gaatgggtgt gagatgaggc cttctcagct catcaaccca cctagggttg aaatcggcgg    240

acacgatctc cgtactttct acactctggt tatggtggat cctgatgctc caagtccaac    300

ctctccaacc ctgagggaat acctccactg gttggtcact gatataccag gaactacagg    360

agcaagcttc ggcaatgaag cgatattcta cgagcctcca aggccgtcaa tgggaatcca    420

ccgttttgtg tttgtgcttt tccggcaact tggccggcag acagtttatg caccggtttg    480

gcgccagaat ttcaacactc gaaactttgc tgagatttac aatcttggtt tgccagtggc    540

cgtcacttac tttaacggcc aaagggaggg tggcaccggc ggtcgatctc cggcagagcc    600

ctgggcagcc gattaattac cctgctcctt cccgttaatt tcatgcatgc atgcatgcta    660

tctatagcat aacatacata tagtatatat cataaataaa taagaccaca tgcattaaca    720

tgtttaattt tcccatgaat atatgttaaa gttgttctag aagaactacg tactccatta    780

tattaccctt tatatatggc aatgaagatg gtttcatctc tatttagaag ctaaaaaaaa    840

aaaaaaaa                                                             848
```

<210> SEQ ID NO 43
<211> LENGTH: 798
<212> TYPE: DNA
<213> ORGANISM: Arabidopsis thaliana

<400> SEQUENCE: 43

```
tttattgaga tacttgagat ccaagataaa tatgtcttta gtcgtagaga tcctcttgtg     60

gtcggcagtg ttgttggaga tgttcttgat cctttcacga ggttggtctc tcttaaggtc    120

acttatggcc atagagaggt tactaatggc ttggatctaa ggccttctca agttctgaac    180

aaaccaatag tggagattgg aggagacgac ttcagaaatt tctacacctt ggttatggtg    240

gatccagatg tgccgagtcc aagcaaccct caccaacgag aatatctcca ctggttggtg    300

actgatatac ctgccaccac tggaaatgcc tttggcaatg aggtggtgtg ctacgagagt    360

ccacgtcccc cctcgggaat tcatcgtatt gtgttggtat tgttccggca actcggaaga    420

caaacggttt atgcaccggg gtggcgccaa cagttcaaca ctcgtgagtt tgctgagatc    480
```

```
tacaatcttg gtcttcctgt ggctgcctct tacttcaact gccagaggga gaatggctgt    540

gggggaagaa gaacgtagat gcgtacctac ttacgttaac taataatcta atcgtataat    600

attcccttaa tgaagtattt aagcatctat gtcaatgtaa taagaattta aagatacgag    660

ctaaaaaaaa tgatgcatat gctgacatcg atgtaaagta gtttacactt ttaatgtaat    720

aactaggttt taacccgcgg tacaccgcga gactattttg ttttttaag aataaaaata     780

taatttgttt agtcgatt                                                  798


<210> SEQ ID NO 44
<211> LENGTH: 519
<212> TYPE: DNA
<213> ORGANISM: Glycine max

<400> SEQUENCE: 44

atggcacggg agaaccctct tgttattggt ggtgtgattg gggatgttct caaccctttt     60

acaagctccg tttctttgac tgtttcaatc aataataggg cgattagcaa tggcttggaa    120

ctcaggccct ctcaagttgt taatcgccct agggttactg ttggtggtga agacctaagg    180

accttctaca ctctggttat ggtggatgca gatgcaccta gccctagcaa ccctgtcttg    240

agggaatacc ttcactggat ggtgacagat attccagcta ccacaaatgc aagctttggg    300

agagaggttg tgttttatga gagcccgaac ccttcagtag ggattcatcg aatcgtgttc    360

gtattgttcc agcaattggg cagagacact gtcatcaccc cagaatggcg ccataatttc    420

aattccagaa actttgctga aattaataac cttgcacctg ttgcagcagc ttatgccaac    480

tgccaaagag agcgtggttg cggtggaagg agatattaa                           519


<210> SEQ ID NO 45
<211> LENGTH: 560
<212> TYPE: DNA
<213> ORGANISM: Zea mays

<400> SEQUENCE: 45

agagcacatc cgtagtgtgt gcatgcatca cagtcacaca cacacagcag aagaagaaga     60

aaccgaacga gggtttagct agcaaaataa acagaagcaa gcaagctagc tagagctaag    120

gatcgagatc gagatcgacc gaccgacgac gatcagctag catggcgcgc ttcgtggatc    180

cgctggtggt ggggcgggtg atcggcgagg tggtggacct gttcgtgcct tccatctcca    240

tgaccgtcgc ctatgatggc cccaaggaca tcagcaacgg ctgcctcctc aagccgtccg    300

ccaccgccgc gccgccgctc gtccgcatct ccggccgccg caacgacctc tacacgctga    360

tcatgacgga ccccgatgcg cctagcccca gcaacccgac catgagggag tacctccact    420

ggatagtgat taacatacca ggaggaacag atgctactaa aggtgaggag gtggtggagt    480

acatgggccc gcggccgccg gtgggtatcc accgctacgt gctggtgctg ttcgagcaga    540

agacgcgcgt gcacgcggag                                                560


<210> SEQ ID NO 46
<211> LENGTH: 1069
<212> TYPE: DNA
<213> ORGANISM: Zea mays

<400> SEQUENCE: 46

tggcaaaaac ccagcgcttt gtgccgccgc cgtccgccgg cccctctgcc cttgtacgcg     60

cacctagaca catcgtcatc gatcatcaca cgcaatcgac acaagaagtt aataaacagc    120

ccaaggacgc agagatcagc tgatcgagaa ggacttgtac tactactcag tattgtcgtc    180
```

```
acatgcacat atatgtacat aaagagctag ctacctgagc tctacccaag gtcgcgttga    240
tcgatcgatc atggcgcggt tcgtggaccc gctggtggtg gggcgggtga tcggcgaggt    300
ggtggacctg ttcgtgccct ccgtctccat gaccgtcgcc tatggcccca aagacatcag    360
caacggctgc ctcctcaagc cgtccgccac cgccgcgccg ccgctcgtcc gcatctccgg    420
ccgccgcgac gacctctaca cgctgatcat gacggaccca gatgcgccta gccccagcga    480
cccgaccatg agggagtacc tccactggat agtgactaac ataccaggag gaacggatgc    540
aaacaaaggt gaggaggtgg tggagtacat gggcccgcgg ccgccggtcg gaatccaccg    600
ctacgtgctg gtgctgttcg agcagaagac gcgtgtgcac gcggagggtc ccggtgagcg    660
cgccaacttc aacacacgcg cgttcgcggc ggcgcacgag ctcggcctcc ccaccgccgt    720
cgtgtacttc aacgcgcaga aagagccggc caaccaccgc cgccgctagc tagtagctcc    780
aacaagggcg cgccagctga gctgcgtgcg tgcaacccac cacacagccg ccggcgaagg    840
ctgcctatat gaccggcgaa taaaaagtct tactgcaccg tccgtaagcg tactctctgt    900
tggtatatgc ttgtcttcag gctcttgagt ctatctactt aaatgtggtt accactgagt    960
aatagaagca gttggcgctt cgatcgatca ttctaatatc cgtacgtgtc aatcattcct   1020
gtttccatca tcttgcattt gaagacgcat tggttctaca ccaaggtgt               1069
```

```
<210> SEQ ID NO 47
<211> LENGTH: 1288
<212> TYPE: DNA
<213> ORGANISM: Cucurbita maxima

<400> SEQUENCE: 47
```

```
gactttttat tcaacaatct ctctctctct ctctcaactt ccgatcaagt ctctccgccg     60
tcttttcacc ggagctgaca attccgatca tttttttgctt cccttaaatt tccggcatgg   120
aggaaccacc gccaaacgcc ttggatttgc cccctggctt cagattccac cccaccgacg    180
aggagatcgt cacttattac ctgatacata agatcaccga cgccgccttc actgccaccg    240
ccatcggaga agctgacctg aataagtgtg aaccttggga tttgccacat aaagctaaga    300
tgggggaaaa agaatggtat ttttttgcc agagagaccg gaaatatccg accgggatga     360
gaacgaaccg ggcgactcag accggttact ggaaagcgac cgggaaagac aaggagattc    420
tcaagggaag aacggttctg gctggtatga agaaaacgct ggttttttac aaaggaagag    480
ctcccaaagg tgaaaagacc aattgggtca tgcatgaatt tcgactcgaa cccaaattct    540
ttcagtttct tggttttccc aagcccatta aggctgattg ggttgtatgt cgggtttttc    600
acaagaacac aacgaacacg gtcggagtag tgaaaaagat tcaaacttct gatttttctt    660
cttctctccc acctctaata gatcccacaa ctgctcatac tccaatcagt ggcagattcg    720
ataatggtga agtcaactgg aggttatcag taccattcga taattatgca aatgattacc    780
attatcatcg gcctttttca gcgacgaata ctgcagtgac aatgatttcg tcgtacccat    840
cgtctgtccc cgacgacgaa ttcttctcat ttgatcaact agacgtcggt ggaacaatgt    900
caatggcggc ggcgacgaca acaacaacaa caactatgga gtgcaaaata gaacaagttt    960
catggtcaac gatgagcggt gtgacaccgg agatatcatc gtcgattgac aacgaggcag   1020
ctctcgagtt ctgggactac tgaaaattga aagtagatgt tatgatcgaa caatggcgat   1080
gctttgtttt aaatgggcat ttcccatatt gaacgtttaa acaatgatta attgattgct   1140
aattattatt atttttttt tttggttaca tagtcctttt tgggaaggaa tattagaact    1200
```

```
ttcatgggtt tggtttgttg attgtattga tatgtagcaa tgtgacattg tatatagctt   1260

ctttatcttt tattttaacc gttgcaaa                                       1288


<210> SEQ ID NO 48
<211> LENGTH: 1964
<212> TYPE: DNA
<213> ORGANISM: Arabidopsis thaliana

<400> SEQUENCE: 48

taataatcat ttttttcttt ataaccttcc tctctatttt tacaatttat tttgttatta     60

gaagtggtag tggagtgaaa aaacaaatcc taagcagtcc taaccgatcc ccgaagctaa    120

agattcttca ccttcccaaa taaagcaaaa cctagatccg acattgaagg aaaaaccttt    180

tagatccatc tctgaaaaaa aaccaaccat gaagagagat catcatcatc atcatcaaga    240

taagaagact atgatgatga atgaagaaga cgacggtaac ggcatggatg agcttctagc    300

tgttcttggt tacaaggtta ggtcatcgga aatggctgat gttgctcaga aactcgagca    360

gcttgaagtt atgatgtcta atgttcaaga agacgatctt tctcaactcg ctactgagac    420

tgttcactat aatccggcgg agctttacac gtggcttgat tctatgctca ccgaccttaa    480

tcctccgtcg tctaacgccg agtacgatct taaagctatt cccggtgacg cgattctcaa    540

tcagttcgct atcgattcgg cttcttcgtc taaccaaggc ggcggaggag atacgtatac    600

tacaaacaag cggttgaaat gctcaaacgg cgtcgtggaa accaccacag cgacggctga    660

gtcaactcgg catgttgtcc tggttgactc gcaggagaac ggtgtgcgtc tcgttcacgc    720

gcttttggct tgcgctgaag ctgttcagaa ggagaatctg actgtggcgg aagctctggt    780

gaagcaaatc ggattcttag ctgtttctca aatcggagct atgagaaaag tcgctactta    840

cttcgccgaa gctctcgcgc ggcggattta ccgtctctct ccgtcgcaga gtccaatcga    900

ccactctctc tccgatactc ttcagatgca cttctacgag acttgtcctt atctcaagtt    960

cgctcacttc acggcgaatc aagcgattct cgaagctttt caagggaaga aaagagttca   1020

tgtcattgat ttctctatga gtcaaggtct tcaatggccg gcgcttatgc aggctcttgc   1080

gcttcgacct ggtggtcctc ctgttttccg gttaaccgga attggtccac cggcaccgga   1140

taatttcgat tatcttcatg aagttgggtg taagctggct catttagctg aggcgattca   1200

cgttgagttt gagtacagag gatttgtggc taacacttta gctgatcttg atgcttcgat   1260

gcttgagctt agaccaagtg agattgaatc tgttgcggtt aactctgttt tcgagcttca   1320

caagctcttg ggacgacctg gtgcgatcga taaggttctt ggtgtggtga atcagattaa   1380

accggagatt ttcactgtgg ttgagcagga atcgaaccat aatagtccga ttttcttaga   1440

tcggtttact gagtcgttgc attattactc gacgttgttt gactcgttgg aaggtgtacc   1500

gagtggtcaa gacaaggtca tgtcggaggt ttacttgggt aaacagatct gcaacgttgt   1560

ggcttgtgat ggacctgacc gagttgagcg tcatgaaacg ttgagtcagt ggaggaaccg   1620

gttcgggtct gctgggtttg cggctgcaca tattggttcg aatgcgttta agcaagcgag   1680

tatgcttttg gctctgttca acggcggtga gggttatcgg gtggaggaga gtgacggctg   1740

tctcatgttg ggttggcaca cacgaccgct catagccacc tcggcttgga aactctccac   1800

caattagatg gtggctcaat gaattgatct gttgaaccgg ttatgatgat agatttccga   1860

ccgaagccaa actaaatcct actgtttttc cctttgtcac ttgttaagat cttatctttc   1920

attatattag gtaattgaaa aatttctaaa ttactcacac tggc                     1964
```

<210> SEQ ID NO 49
<211> LENGTH: 1556
<212> TYPE: DNA
<213> ORGANISM: Lycopersicon esculentum

<400> SEQUENCE: 49
aaagaaaaaa ggaatattgt gtgtttgctt ttttttctga ctagtagtat tgctaactat 60
gtattccatt aaggatttgc tgtgaaaaag cctgatatca gtaagcataa aactcgggag 120
atcacttaca cacacacaca ccctcctaaa aaagagaaga gagatttact gttaaacaga 180 ggttttttttc catttctttt tttttttcag tgtgtgtgtg agagaaagag atgattttca 240
taggcacaaa caaatagaaa ggaacaaaat ttagagtgaa gaagaaagtg tgtgagagaa 300
taatggaggg tggttctagt ggaaatacta gtacatcttg tttaatgatg atgggatatg 360
gagatcatga aaacaacaac aacaacaatg gaaatggtaa tggaaatgga aatggaaatg 420
taacaatttg tgctcctcca atgatgatga tgatgcctcc tcctcctcct tctttaacta 480
acaataacaa tgcagaaaca agcaacaaca acatcctttt tcttcctttc atggacaaca 540
acaacaacaa taatcctcaa gaagacaaca actcttcttc ttcttccatc aagtcaaaga 600
ttatggctca tcctcactac catcgtctct tgactgctta tctcaattgt caaaagatag 660
gagctccgcc agaagtggtg gcaaggctag aggaaatatg tgccacgtca gcaacaatgg 720
gccgtagcag tagtagtagt ggtggtggaa tcattggaga agatcctgca ctagatcagt 780
tcatggaggc ttattgtgag atgctgacaa aatatgaaca agaactctca aaacccttca 840
aggaagccat ggtttttctt tcaagaattg agtgtcagtt caaagcttta actcttgcac 900
ctaattcttc tcatgaatct gctttgggcg aggcaatgga tagaaatgga tcatctgatg 960
aagaggttga cgtgaataac agtttcatcg acccccaggc tgaggataga gagctcaaag 1020
gtcaattgtt gcgtaagtac agcggttact tgggaagcct taagcaggag ttcatgaaga 1080
agaggaagaa aggcaagctg cctaaggaag caaggcaaca attggtggat tggtggctta 1140
gacatattaa atggccatat ccatcggaat ctcagaagct tgcactagct gaatcaacgg 1200
gattggacca gaagcaaata aacaactggt ttatcaatca aagaaagagg cattggaaac 1260
catcagaaga tatgcagttt gttgtgatgg atgctgctca tccacattac tatatggata 1320
atgttcttgc taaccatttc ccaatggata tgacaccctc tctcctctga attaagattt 1380
gtcattatta atatcaagga tgtttaatta atttgcatat tacttgtgtg catgtagtag 1440
tacaagctat tgtgacacaa tcaacttttt attagaccaa atatataaag tgcttgtaat 1500
agatctttct attatcatct ttaattatgg aattaaatag tttgtacttg ctaaaa 1556

<210> SEQ ID NO 50
<211> LENGTH: 2735
<212> TYPE: DNA
<213> ORGANISM: Solanum tuberosum

<400> SEQUENCE: 50
catgcagaga taaaaatata gatcagtctg acaagaaggc aacttctcaa agcttagaga 60
gctaccaccc gaagatagac agttagttac atgtactgtt atagataaaa ggagaaatcc 120
gaagaagaaa gaatttttttt tgcagatatg tactatcaag gaacctcgga taatactaat 180
atacaagctg atcatcaaca acgtcataat catgggaata gtaataataa taatattcag 240
acactttatt tgatgaaccc taacaattat atgcaaggct acactacttc tgacacacag 300
cagcagcagc agttactttt cctgaattct tcaccagcag caagcaacgc gctttgccat 360

```
gcgaatatac aacacgcgcc gctgcaacag cagcactttg tcggtgtgcc tcttccggca    420
gtaagtttgc acgatcagat caatcatcat ggacttttac agcgcatgtg gaacaaccaa    480
gatcaatctc agcaggtgat agtaccatcg tcgacggggg tttctgccac gtcatgtggc    540
gggatcacca cggacttggc gtctcaattg gcgtttcaga ggccgattcc gacaccacaa    600
caccgacagc agcaacaaca gcaaggcggt ctatctctaa gcctttctcc tcagctacaa    660
cagcaaatta gtttcaataa caatatttca tcctcatcac caaggacaaa taatgttact    720
attaggggaa cattagatgg aagttctagc aacatggttt taggctctaa gtatctgaaa    780
gctgcacaag agcttcttga tgaagttgtt aatattgttg gaaaaagcat caaaggagat    840
gatcaaaaga aggataattc aatgaataaa gaatcaatgc ctttggctag tgatgtcaac    900
actaatagtt ctggtggtgg tgaaagtagc agcaggcaga aaaatgaagt tgctgttgag    960
cttacaactg ctcaaagaca agaacttcaa atgaaaaaag ccaagcttct tgccatgctt   1020
gaagaggtgg agcaaaggta cagacagtac catcaccaaa tgcaaataat tgtattatca   1080
tttgagcaag tagcaggaat tggatcagcc aaatcataca ctcaattagc tttgcatgca   1140
atttcgaagc aattcagatg cctaaaggat gcaattgctg agcaagtaaa ggcgacgagc   1200
aagagtttag gtgaagagga aggcttggga gggaaaatcg aaggctcaag actcaaattt   1260
gtggaccatc atctaaggca acaacgcgcg ctgcaacaga taggaatgat gcaaccaaat   1320
gcttggagac cccaaagagg tttacctgaa agagctgtct ctgtccttcg tgcttggctt   1380
ttcgagcatt ttcttcatcc ttacccaaag gattcagaca aaatcatgct tgctaagcaa   1440
acggggctaa caaggagcca ggtgtctaac tggttcataa atgctcgagt tcgattatgg   1500
aagccaatgg tagaagaaat gtacttggaa gaagtgaaga atcaagaaca aaacagtact   1560
aatacttcag gagataacaa aaacaaagag accaatataa gtgctccaaa tgaagagaaa   1620
catccaatta ttactagcag cttattacaa gatggtatta ctactactca agcagaaatt   1680
tctacctcaa ctatttcaac ttcccctact gcaggtgctt cacttcatca tgctcacaat   1740
ttctccttcc ttggttcatt caacatggat aatactacta ctactgttga tcatattgaa   1800
aacaacgcga aaaagcaaag aaatgacatg cacaagtttt ctccaagtag tattctttca   1860
tctgttgaca tggaagccaa agctagagaa tcatcaaata aagggtttac taatccttta   1920
atggcagcat acgcgatggg agattttgga aggtttgatc ctcatgatca acaaatgacc   1980
gcgaattttc atggaaataa tggtgtctct cttactttag gacttcctcc ttctgaaaac   2040
ctagccatgc cagtgagcca acaaaattac ctttctaatg acttgggaag taggtctgaa   2100
atggggagtc attacaatag aatgggatat gaaaacattg attttcagag tgggaataag   2160
cgatttccga ctcaactatt accagatttt gttacaggta atctaggaac atgaatacca   2220
gaaagtctcg tattgatagc tgaaaagata aaaggaagtt agggatactc ttatattgtg   2280
tgaggccttc tggcccaagt cggaggaccc aatttgatac aacctatcat aggagaaaag   2340
aagtggagac taaattaaag taacaaaatt ttaaagcaca ctttctagta tatatacttc   2400
ttttttttat agtatagaaa agaagagatt ttgtgcttta gtgtatagat agagtctact   2460
tagtataggt tatacttcta gttccttgag aagattgata caactagtag tatttttttt   2520
cttttgggtt ggcttggagt actattttaa gttattggaa actagctata gtaaatgttg   2580
taaagttgtg atattgttcc tctcaatttg catataattt gaaatatttt gtacctacta   2640
gctagtctct aaattatgtt tccattgctt gtaattgcaa ttttatttga attttgtgct   2700
atcattatta gattagcaaa aaaaaaaaaa aaaaa                              2735
```

<210> SEQ ID NO 51
<211> LENGTH: 72
<212> TYPE: DNA
<213> ORGANISM: Arabidopsis thaliana

<400> SEQUENCE: 51
atcagagtgg cgcagcggaa gcgtggtggg cccataaccc acaggtccca ggatcgaaac 60
ctggctctga ta 72

<210> SEQ ID NO 52
<211> LENGTH: 71
<212> TYPE: DNA
<213> ORGANISM: Arabidopsis thaliana

<400> SEQUENCE: 52
gcaccagtgg tctagtggca tgatagtacc ctgccacggt acagacccgg gttcaattcc 60
cggctggtgc a 71

<210> SEQ ID NO 53
<211> LENGTH: 1230
<212> TYPE: PRT
<213> ORGANISM: Francisella tularensis

<400> SEQUENCE: 53

Ile Ser Glu Asp Leu Leu Gln Asn Tyr Ser Asp Val Tyr Phe Lys Leu
1 5 10 15

Lys Lys Ser Asp Asp Asp Asn Leu Gln Lys Asp Phe Lys Ser Ala Lys
20 25 30

Asp Thr Ile Lys Lys Gln Ile Ser Glu Tyr Ile Lys Asp Ser Glu Lys
35 40 45

Phe Lys Asn Leu Phe Asn Gln Asn Leu Ile Asp Ala Lys Lys Gly Gln
50 55 60

Glu Ser Asp Leu Ile Leu Trp Leu Lys Gln Ser Lys Asp Asn Gly Ile
65 70 75 80

Glu Leu Phe Lys Ala Asn Ser Asp Ile Thr Asp Ile Asp Glu Ala Leu
85 90 95

Glu Ile Ile Lys Ser Phe Lys Gly Trp Thr Thr Tyr Phe Lys Gly Phe
100 105 110

His Glu Asn Arg Lys Asn Val Tyr Ser Ser Asn Asp Ile Pro Thr Ser
115 120 125

Ile Ile Tyr Arg Ile Val Asp Asp Asn Leu Pro Lys Phe Leu Glu Asn
130 135 140

Lys Ala Lys Tyr Glu Ser Leu Lys Asp Lys Ala Pro Glu Ala Ile Asn
145 150 155 160

Tyr Glu Gln Ile Lys Lys Asp Leu Ala Glu Glu Leu Thr Phe Asp Ile
165 170 175

Asp Tyr Lys Thr Ser Glu Val Asn Gln Arg Val Phe Ser Leu Asp Glu
180 185 190

Val Phe Glu Ile Ala Asn Phe Asn Asn Tyr Leu Asn Gln Ser Gly Ile
195 200 205

Thr Lys Phe Asn Thr Ile Ile Gly Gly Lys Phe Val Asn Gly Glu Asn
210 215 220

Thr Lys Arg Lys Gly Ile Asn Glu Tyr Ile Asn Leu Tyr Ser Gln Gln
225 230 235 240

Ile Asn Asp Lys Thr Leu Lys Lys Tyr Lys Met Ser Val Leu Phe Lys

```
                245                 250                 255

Gln Ile Leu Ser Asp Thr Glu Ser Lys Ser Phe Val Ile Asp Lys Leu
            260                 265                 270

Glu Asp Asp Ser Asp Val Val Thr Thr Met Gln Ser Phe Tyr Glu Gln
        275                 280                 285

Ile Ala Ala Phe Lys Thr Val Glu Glu Lys Ser Ile Lys Glu Thr Leu
    290                 295                 300

Ser Leu Leu Phe Asp Asp Leu Lys Ala Gln Lys Leu Asp Leu Ser Lys
305                 310                 315                 320

Ile Tyr Phe Lys Asn Asp Lys Ser Leu Thr Asp Leu Ser Gln Gln Val
                325                 330                 335

Phe Asp Asp Tyr Ser Val Ile Gly Thr Ala Val Leu Glu Tyr Ile Thr
            340                 345                 350

Gln Gln Ile Ala Pro Lys Asn Leu Asp Asn Pro Ser Lys Lys Glu Gln
        355                 360                 365

Glu Leu Ile Ala Lys Lys Thr Glu Lys Ala Lys Tyr Leu Ser Leu Glu
    370                 375                 380

Thr Ile Lys Leu Ala Leu Glu Glu Phe Asn Lys His Arg Asp Ile Asp
385                 390                 395                 400

Lys Gln Cys Arg Phe Glu Glu Ile Leu Ala Asn Phe Ala Ala Ile Pro
                405                 410                 415

Met Ile Phe Asp Glu Ile Ala Gln Asn Lys Asp Asn Leu Ala Gln Ile
            420                 425                 430

Ser Ile Lys Tyr Gln Asn Gln Gly Lys Lys Asp Leu Leu Gln Ala Ser
        435                 440                 445

Ala Glu Asp Asp Val Lys Ala Ile Lys Asp Leu Leu Asp Gln Thr Asn
    450                 455                 460

Asn Leu Leu His Lys Leu Lys Ile Phe His Ile Ser Gln Ser Glu Asp
465                 470                 475                 480

Lys Ala Asn Ile Leu Asp Lys Asp Glu His Phe Tyr Leu Val Phe Glu
                485                 490                 495

Glu Cys Tyr Phe Glu Leu Ala Asn Ile Val Pro Leu Tyr Asn Lys Ile
            500                 505                 510

Arg Asn Tyr Ile Thr Gln Lys Pro Tyr Ser Asp Glu Lys Phe Lys Leu
        515                 520                 525

Asn Phe Glu Asn Ser Thr Leu Ala Asn Gly Trp Asp Lys Asn Lys Glu
    530                 535                 540

Pro Asp Asn Thr Ala Ile Leu Phe Ile Lys Asp Asp Lys Tyr Tyr Leu
545                 550                 555                 560

Gly Val Met Asn Lys Lys Asn Asn Lys Ile Phe Asp Asp Lys Ala Ile
                565                 570                 575

Lys Glu Asn Lys Gly Glu Gly Tyr Lys Lys Ile Val Tyr Lys Leu Leu
            580                 585                 590

Pro Gly Ala Asn Lys Met Leu Pro Lys Val Phe Phe Ser Ala Lys Ser
        595                 600                 605

Ile Lys Phe Tyr Asn Pro Ser Glu Asp Ile Leu Arg Ile Arg Asn His
    610                 615                 620

Ser Thr His Thr Lys Asn Gly Ser Pro Gln Lys Gly Tyr Glu Lys Phe
625                 630                 635                 640

Glu Phe Asn Ile Glu Asp Cys Arg Lys Phe Ile Asp Phe Tyr Lys Gln
                645                 650                 655

Ser Ile Ser Lys His Pro Glu Trp Lys Asp Phe Gly Phe Arg Phe Ser
            660                 665                 670
```

```
Asp Thr Gln Arg Tyr Asn Ser Ile Asp Glu Phe Tyr Arg Glu Val Glu
        675                 680                 685

Asn Gln Gly Tyr Lys Leu Thr Phe Glu Asn Ile Ser Glu Ser Tyr Ile
    690                 695                 700

Asp Ser Val Val Asn Gln Gly Lys Leu Tyr Leu Phe Gln Ile Tyr Asn
705                 710                 715                 720

Lys Asp Phe Ser Ala Tyr Ser Lys Gly Arg Pro Asn Leu His Thr Leu
                725                 730                 735

Tyr Trp Lys Ala Leu Phe Asp Glu Arg Asn Leu Gln Asp Val Val Tyr
            740                 745                 750

Lys Leu Asn Gly Glu Ala Glu Leu Phe Tyr Arg Lys Gln Ser Ile Pro
        755                 760                 765

Lys Lys Ile Thr His Pro Ala Lys Glu Ala Ile Ala Asn Lys Asn Lys
    770                 775                 780

Asp Asn Pro Lys Lys Glu Ser Val Phe Glu Tyr Asp Leu Ile Lys Asp
785                 790                 795                 800

Lys Arg Phe Thr Glu Asp Lys Phe Phe Phe His Cys Pro Ile Thr Ile
                805                 810                 815

Asn Phe Lys Ser Ser Gly Ala Asn Lys Phe Asn Asp Glu Ile Asn Leu
            820                 825                 830

Leu Leu Lys Glu Lys Ala Asn Asp Val His Ile Leu Ser Ile Asp Arg
        835                 840                 845

Gly Glu Arg His Leu Ala Tyr Tyr Thr Leu Val Asp Gly Lys Gly Asn
    850                 855                 860

Ile Ile Lys Gln Asp Thr Phe Asn Ile Ile Gly Asn Asp Arg Met Lys
865                 870                 875                 880

Thr Asn Tyr His Asp Lys Leu Ala Ala Ile Glu Lys Asp Arg Asp Ser
                885                 890                 895

Ala Arg Lys Asp Trp Lys Lys Ile Asn Asn Ile Lys Glu Met Lys Glu
            900                 905                 910

Gly Tyr Leu Ser Gln Val Val His Glu Ile Ala Lys Leu Val Ile Glu
        915                 920                 925

Tyr Asn Ala Ile Val Val Phe Glu Asp Leu Asn Phe Gly Phe Lys Arg
    930                 935                 940

Gly Arg Phe Lys Val Glu Lys Gln Val Tyr Gln Lys Leu Glu Lys Met
945                 950                 955                 960

Leu Ile Glu Lys Leu Asn Tyr Leu Val Phe Lys Asp Asn Glu Phe Asp
                965                 970                 975

Lys Thr Gly Gly Val Leu Arg Ala Tyr Gln Leu Thr Ala Pro Phe Glu
            980                 985                 990

Thr Phe Lys Lys Met Gly Lys Gln  Thr Gly Ile Ile Tyr  Tyr Val Pro
        995                 1000                 1005

Ala Gly  Phe Thr Ser Lys Ile  Cys Pro Val Thr Gly  Phe Val Asn
    1010                 1015                 1020

Gln Leu  Tyr Pro Lys Tyr Glu  Ser Val Ser Lys Ser  Gln Glu Phe
    1025                 1030                 1035

Phe Ser  Lys Phe Asp Lys Ile  Cys Tyr Asn Leu Asp  Lys Gly Tyr
    1040                 1045                 1050

Phe Glu  Phe Ser Phe Asp Tyr  Lys Asn Phe Gly Asp  Lys Ala Ala
    1055                 1060                 1065

Lys Gly  Lys Trp Thr Ile Ala  Ser Phe Gly Ser Arg  Leu Ile Asn
    1070                 1075                 1080
```

```
Phe Arg  Asn Ser Asp Lys Asn  His Asn Trp Asp Thr  Arg Glu Val
    1085                 1090                 1095

Tyr Pro  Thr Lys Glu Leu Glu  Lys Leu Leu Lys Asp  Tyr Ser Ile
    1100                 1105                 1110

Glu Tyr  Gly His Gly Glu Cys  Ile Lys Ala Ala Ile  Cys Gly Glu
    1115                 1120                 1125

Ser Asp  Lys Lys Phe Phe Ala  Lys Leu Thr Ser Val  Leu Asn Thr
    1130                 1135                 1140

Ile Leu  Gln Met Arg Asn Ser  Lys Thr Gly Thr Glu  Leu Asp Tyr
    1145                 1150                 1155

Leu Ile  Ser Pro Val Ala Asp  Val Asn Gly Asn Phe  Phe Asp Ser
    1160                 1165                 1170

Arg Gln  Ala Pro Lys Asn Met  Pro Gln Asp Ala Asp  Ala Asn Gly
    1175                 1180                 1185

Ala Tyr  His Ile Gly Leu Lys  Gly Leu Met Leu Leu  Gly Arg Ile
    1190                 1195                 1200

Lys Asn  Asn Gln Glu Gly Lys  Lys Leu Asn Leu Val  Ile Lys Asn
    1205                 1210                 1215

Glu Glu  Tyr Phe Glu Phe Val  Gln Asn Arg Asn Asn
    1220                 1225                 1230


<210> SEQ ID NO 54
<211> LENGTH: 38
<212> TYPE: RNA
<213> ORGANISM: Francisella tularensis

<400> SEQUENCE: 54

gggucuaaga acuuuaaaua auuucuacug uuguacau                          38


<210> SEQ ID NO 55
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 55

Ala Ala Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45

Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
            100                 105                 110

Ala Ala Gly Tyr Lys Ser Leu Phe Lys Lys Asp Ile Ile Glu Thr Ile
        115                 120                 125

Leu Pro Glu Ala Ala Asp Asp Lys Asp Glu Ile Ala Leu Val Asn Ser
    130                 135                 140

Phe Asn Gly Phe Thr Thr Ala Phe Thr Gly Phe Phe Asp Asn Arg Glu
145                 150                 155                 160
```

```
Asn Met Phe Ser Glu Glu Ala Lys Ser Thr Ser Ile Ala Phe Arg Cys
                165                 170                 175

Ile Asn Glu Asn Leu Thr Arg Tyr Ile Ser Asn Met Asp Ile Phe Glu
            180                 185                 190

Lys Val Asp Ala Ile Phe Asp Lys His Glu Val Gln Glu Ile Lys Glu
        195                 200                 205

Lys Ile Leu Asn Ser Asp Tyr Asp Val Glu Asp Phe Phe Glu Gly Glu
    210                 215                 220

Phe Phe Asn Phe Val Leu Thr Gln Glu Gly Ile Asp Val Tyr Asn Ala
225                 230                 235                 240

Ile Ile Gly Gly Phe Val Thr Glu Ser Gly Glu Lys Ile Lys Gly Leu
                245                 250                 255

Asn Glu Tyr Ile Asn Leu Tyr Asn Ala Lys Thr Lys Gln Ala Leu Pro
            260                 265                 270

Lys Phe Lys Pro Leu Tyr Lys Gln Val Leu Ser Asp Arg Glu Ser Leu
        275                 280                 285

Ser Phe Tyr Gly Glu Gly Tyr Thr Ser Asp Glu Glu Val Leu Glu Val
    290                 295                 300

Phe Arg Asn Thr Leu Asn Lys Asn Ser Glu Ile Phe Ser Ser Ile Lys
305                 310                 315                 320

Lys Leu Glu Lys Leu Phe Lys Asn Phe Asp Glu Tyr Ser Ser Ala Gly
                325                 330                 335

Ile Phe Val Lys Asn Gly Pro Ala Ile Ser Thr Ile Ser Lys Asp Ile
            340                 345                 350

Phe Gly Glu Trp Asn Leu Ile Arg Asp Lys Trp Asn Ala Glu Tyr Asp
        355                 360                 365

Asp Ile His Leu Lys Lys Lys Ala Val Val Thr Glu Lys Tyr Glu Asp
    370                 375                 380

Asp Arg Arg Lys Ser Phe Lys Lys Ile Gly Ser Phe Ser Leu Glu Gln
385                 390                 395                 400

Leu Gln Glu Tyr Ala Asp Ala Asp Leu Ser Val Val Glu Lys Leu Lys
                405                 410                 415

Glu Ile Ile Ile Gln Lys Val Asp Glu Ile Tyr Lys Val Tyr Gly Ser
            420                 425                 430

Ser Glu Lys Leu Phe Asp Ala Asp Phe Val Leu Glu Lys Ser Leu Lys
        435                 440                 445

Lys Asn Asp Ala Val Val Ala Ile Met Lys Asp Leu Leu Asp Ser Val
    450                 455                 460

Lys Ser Phe Glu Asn Tyr Ile Lys Ala Phe Phe Gly Glu Gly Lys Glu
465                 470                 475                 480

Thr Asn Arg Asp Glu Ser Phe Tyr Gly Asp Phe Val Leu Ala Tyr Asp
                485                 490                 495

Ile Leu Leu Lys Val Asp His Ile Tyr Asp Ala Ile Arg Asn Tyr Val
            500                 505                 510

Thr Gln Lys Pro Tyr Ser Lys Asp Lys Phe Lys Leu Tyr Phe Gln Asn
        515                 520                 525

Pro Gln Phe Met Gly Gly Trp Asp Lys Asp Lys Glu Thr Asp Tyr Arg
    530                 535                 540

Ala Thr Ile Leu Arg Tyr Gly Ser Lys Tyr Tyr Leu Ala Ile Met Asp
545                 550                 555                 560

Lys Lys Tyr Ala Lys Cys Leu Gln Lys Ile Asp Lys Asp Asp Val Asn
                565                 570                 575
```

```
Gly Asn Tyr Glu Lys Ile Asn Tyr Lys Leu Leu Pro Gly Pro Asn Lys
            580                 585                 590

Met Leu Pro Lys Val Phe Phe Ser Lys Lys Trp Met Ala Tyr Tyr Asn
        595                 600                 605

Pro Ser Glu Asp Ile Gln Lys Ile Tyr Lys Asn Gly Thr Phe Lys Lys
    610                 615                 620

Gly Asp Met Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
            660                 665                 670

Glu Val Glu Glu Gln Gly Tyr Lys Val Ser Phe Glu Ser Ala Ser Lys
        675                 680                 685

Lys Glu Val Asp Lys Leu Val Glu Glu Gly Lys Leu Tyr Met Phe Gln
    690                 695                 700

Ile Tyr Asn Lys Asp Phe Ser Asp Lys Ser His Gly Thr Pro Asn Leu
705                 710                 715                 720

His Thr Met Tyr Phe Lys Leu Leu Phe Asp Glu Asn Asn His Gly Gln
                725                 730                 735

Ile Arg Leu Ser Gly Gly Ala Glu Leu Phe Met Arg Arg Ala Ser Leu
            740                 745                 750

Lys Lys Glu Glu Leu Val Val His Pro Ala Asn Ser Pro Ile Ala Asn
        755                 760                 765

Lys Asn Pro Asp Asn Pro Lys Lys Thr Thr Thr Leu Ser Tyr Asp Val
    770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp  Leu Thr Ser Lys Ile  Asp Pro Ser
```

```
        995                 1000                1005

Thr Gly  Phe Val Asn Leu Leu  Lys Thr Lys Tyr Thr  Ser Ile Ala
    1010                 1015                 1020

Asp Ser  Lys Lys Phe Ile Ser  Ser Phe Asp Arg Ile  Met Tyr Val
    1025                 1030                 1035

Pro Glu  Glu Asp Leu Phe Glu  Phe Ala Leu Asp Tyr  Lys Asn Phe
    1040                 1045                 1050

Ser Arg  Thr Asp Ala Asp Tyr  Ile Lys Lys Trp Lys  Leu Tyr Ser
    1055                 1060                 1065

Tyr Gly  Asn Arg Ile Arg Ile  Phe Ala Ala Ala Lys  Lys Asn Asn
    1070                 1075                 1080

Val Phe  Ala Trp Glu Glu Val  Cys Leu Thr Ser Ala  Tyr Lys Glu
    1085                 1090                 1095

Leu Phe  Asn Lys Tyr Gly Ile  Asn Tyr Gln Gln Gly  Asp Ile Arg
    1100                 1105                 1110

Ala Leu  Leu Cys Glu Gln Ser  Asp Lys Ala Phe Tyr  Ser Ser Phe
    1115                 1120                 1125

Met Ala  Leu Met Ser Leu Met  Leu Gln Met Arg Asn  Ser Ile Thr
    1130                 1135                 1140

Gly Arg  Thr Asp Val Asp Phe  Leu Ile Ser Pro Val  Lys Asn Ser
    1145                 1150                 1155

Asp Gly  Ile Phe Tyr Asp Ser  Arg Asn Tyr Glu Ala  Gln Glu Asn
    1160                 1165                 1170

Ala Ile  Leu Pro Lys Asn Ala  Asp Ala Asn Gly Ala  Tyr Asn Ile
    1175                 1180                 1185

Ala Arg  Lys Val Leu Trp Ala  Ile Gly Gln Phe Lys  Lys Ala Glu
    1190                 1195                 1200

Asp Glu  Lys Leu Asp Lys Val  Lys Ile Ala Ile Ser  Asn Lys Glu
    1205                 1210                 1215

Trp Leu  Glu Tyr Ala Gln Thr  Ser Val Lys
    1220                 1225


<210> SEQ ID NO 56
<211> LENGTH: 36
<212> TYPE: RNA
<213> ORGANISM: Unknown
<220> FEATURE:
<223> OTHER INFORMATION: Lachnospiraceae bacterium

<400> SEQUENCE: 56

guuucaaaga uuaaauaauu ucuacuaagu guagau                               36


<210> SEQ ID NO 57
<211> LENGTH: 707
<212> TYPE: PRT
<213> ORGANISM: Unknown
<220> FEATURE:
<223> OTHER INFORMATION: bacteriophage

<400> SEQUENCE: 57

Met Ala Asp Thr Pro Thr Leu Phe Thr Gln Phe Leu Arg His His Leu
1               5                   10                  15

Pro Gly Gln Arg Phe Arg Lys Asp Ile Leu Lys Gln Ala Gly Arg Ile
            20                  25                  30

Leu Ala Asn Lys Gly Glu Asp Ala Thr Ile Ala Phe Leu Arg Gly Lys
        35                  40                  45

Ser Glu Glu Ser Pro Pro Asp Phe Gln Pro Pro Val Lys Cys Pro Ile
```

```
    50                  55                  60

Ile Ala Cys Ser Arg Pro Leu Thr Glu Trp Pro Ile Tyr Gln Ala Ser
65                  70                  75                  80

Val Ala Ile Gln Gly Tyr Val Tyr Gly Gln Ser Leu Ala Glu Phe Glu
                85                  90                  95

Ala Ser Asp Pro Gly Cys Ser Lys Asp Gly Leu Leu Gly Trp Phe Asp
            100                 105                 110

Lys Thr Gly Val Cys Thr Asp Tyr Phe Ser Val Gln Gly Leu Asn Leu
        115                 120                 125

Ile Phe Gln Asn Ala Arg Lys Arg Tyr Ile Gly Val Gln Thr Lys Val
    130                 135                 140

Thr Asn Arg Asn Glu Lys Arg His Lys Lys Leu Lys Arg Ile Asn Ala
145                 150                 155                 160

Lys Arg Ile Ala Glu Gly Leu Pro Glu Leu Thr Ser Asp Glu Pro Glu
                165                 170                 175

Ser Ala Leu Asp Glu Thr Gly His Leu Ile Asp Pro Pro Gly Leu Asn
            180                 185                 190

Thr Asn Ile Tyr Cys Tyr Gln Gln Val Ser Pro Lys Pro Leu Ala Leu
        195                 200                 205

Ser Glu Val Asn Gln Leu Pro Thr Ala Tyr Ala Gly Tyr Ser Thr Ser
    210                 215                 220

Gly Asp Asp Pro Ile Gln Pro Met Val Thr Lys Asp Arg Leu Ser Ile
225                 230                 235                 240

Ser Lys Gly Gln Pro Gly Tyr Ile Pro Glu His Gln Arg Ala Leu Leu
                245                 250                 255

Ser Gln Lys Lys His Arg Arg Met Arg Gly Tyr Gly Leu Lys Ala Arg
            260                 265                 270

Ala Leu Leu Val Ile Val Arg Ile Gln Asp Asp Trp Ala Val Ile Asp
        275                 280                 285

Leu Arg Ser Leu Leu Arg Asn Ala Tyr Trp Arg Arg Ile Val Gln Thr
    290                 295                 300

Lys Glu Pro Ser Thr Ile Thr Lys Leu Leu Lys Leu Val Thr Gly Asp
305                 310                 315                 320

Pro Val Leu Asp Ala Thr Arg Met Val Ala Thr Phe Thr Tyr Lys Pro
                325                 330                 335

Gly Ile Val Gln Val Arg Ser Ala Lys Cys Leu Lys Asn Lys Gln Gly
            340                 345                 350

Ser Lys Leu Phe Ser Glu Arg Tyr Leu Asn Glu Thr Val Ser Val Thr
        355                 360                 365

Ser Ile Asp Leu Gly Ser Asn Asn Leu Val Ala Val Ala Thr Tyr Arg
    370                 375                 380

Leu Val Asn Gly Asn Thr Pro Glu Leu Leu Gln Arg Phe Thr Leu Pro
385                 390                 395                 400

Ser His Leu Val Lys Asp Phe Glu Arg Tyr Lys Gln Ala His Asp Thr
                405                 410                 415

Leu Glu Asp Ser Ile Gln Lys Thr Ala Val Ala Ser Leu Pro Gln Gly
            420                 425                 430

Gln Gln Thr Glu Ile Arg Met Trp Ser Met Tyr Gly Phe Arg Glu Ala
        435                 440                 445

Gln Glu Arg Val Cys Gln Glu Leu Gly Leu Ala Asp Gly Ser Ile Pro
    450                 455                 460

Trp Asn Val Met Thr Ala Thr Ser Thr Ile Leu Thr Asp Leu Phe Leu
465                 470                 475                 480
```

```
Ala Arg Gly Gly Asp Pro Lys Lys Cys Met Phe Thr Ser Glu Pro Lys
                485                 490                 495

Lys Lys Lys Asn Ser Lys Gln Val Leu Tyr Lys Ile Arg Asp Arg Ala
            500                 505                 510

Trp Ala Lys Met Tyr Arg Thr Leu Leu Ser Lys Glu Thr Arg Glu Ala
        515                 520                 525

Trp Asn Lys Ala Leu Trp Gly Leu Lys Arg Gly Ser Pro Asp Tyr Ala
    530                 535                 540

Arg Leu Ser Lys Arg Lys Glu Glu Leu Ala Arg Arg Cys Val Asn Tyr
545                 550                 555                 560

Thr Ile Ser Thr Ala Glu Lys Arg Ala Gln Cys Gly Arg Thr Ile Val
                565                 570                 575

Ala Leu Glu Asp Leu Asn Ile Gly Phe Phe His Gly Arg Gly Lys Gln
            580                 585                 590

Glu Pro Gly Trp Val Gly Leu Phe Thr Arg Lys Lys Glu Asn Arg Trp
        595                 600                 605

Leu Met Gln Ala Leu His Lys Ala Phe Leu Glu Leu Ala His His Arg
    610                 615                 620

Gly Tyr His Val Ile Glu Val Asn Pro Ala Tyr Thr Ser Gln Thr Cys
625                 630                 635                 640

Pro Val Cys Arg His Cys Asp Pro Asp Asn Arg Asp Gln His Asn Arg
                645                 650                 655

Glu Ala Phe His Cys Ile Gly Cys Gly Phe Arg Gly Asn Ala Asp Leu
            660                 665                 670

Asp Val Ala Thr His Asn Ile Ala Met Val Ala Ile Thr Gly Glu Ser
        675                 680                 685

Leu Lys Arg Ala Arg Gly Ser Val Ala Ser Lys Thr Pro Gln Pro Leu
    690                 695                 700

Ala Ala Glu
705


<210> SEQ ID NO 58
<211> LENGTH: 36
<212> TYPE: RNA
<213> ORGANISM: Unknown
<220> FEATURE:
<223> OTHER INFORMATION: bacteriophage

<400> SEQUENCE: 58

ggagagaucu caaacgauug cucgauuagu cgagac                             36


<210> SEQ ID NO 59
<211> LENGTH: 757
<212> TYPE: PRT
<213> ORGANISM: Unknown
<220> FEATURE:
<223> OTHER INFORMATION: bacteriophage

<400> SEQUENCE: 59

Met Pro Lys Pro Ala Val Glu Ser Glu Phe Ser Lys Val Leu Lys Lys
1               5                   10                  15

His Phe Pro Gly Glu Arg Phe Arg Ser Ser Tyr Met Lys Arg Gly Gly
            20                  25                  30

Lys Ile Leu Ala Ala Gln Gly Glu Glu Ala Val Val Ala Tyr Leu Gln
        35                  40                  45

Gly Lys Ser Glu Glu Glu Pro Pro Asn Phe Gln Pro Pro Ala Lys Cys
    50                  55                  60
```

```
His Val Val Thr Lys Ser Arg Asp Phe Ala Glu Trp Pro Ile Met Lys
65                  70                  75                  80

Ala Ser Glu Ala Ile Gln Arg Tyr Ile Tyr Ala Leu Ser Thr Thr Glu
                85                  90                  95

Arg Ala Ala Cys Lys Pro Gly Lys Ser Ser Glu Ser His Ala Ala Trp
            100                 105                 110

Phe Ala Ala Thr Gly Val Ser Asn His Gly Tyr Ser His Val Gln Gly
        115                 120                 125

Leu Asn Leu Ile Phe Asp His Thr Leu Gly Arg Tyr Asp Gly Val Leu
    130                 135                 140

Lys Lys Val Gln Leu Arg Asn Glu Lys Ala Arg Ala Arg Leu Glu Ser
145                 150                 155                 160

Ile Asn Ala Ser Arg Ala Asp Glu Gly Leu Pro Glu Ile Lys Ala Glu
                165                 170                 175

Glu Glu Glu Val Ala Thr Asn Glu Thr Gly His Leu Leu Gln Pro Pro
            180                 185                 190

Gly Ile Asn Pro Ser Phe Tyr Val Tyr Gln Thr Ile Ser Pro Gln Ala
        195                 200                 205

Tyr Arg Pro Arg Asp Glu Ile Val Leu Pro Pro Glu Tyr Ala Gly Tyr
    210                 215                 220

Val Arg Asp Pro Asn Ala Pro Ile Pro Leu Gly Val Val Arg Asn Arg
225                 230                 235                 240

Cys Asp Ile Gln Lys Gly Cys Pro Gly Tyr Ile Pro Glu Trp Gln Arg
                245                 250                 255

Glu Ala Gly Thr Ala Ile Ser Pro Lys Thr Gly Lys Ala Val Thr Val
            260                 265                 270

Pro Gly Leu Ser Pro Lys Lys Asn Lys Arg Met Arg Arg Tyr Trp Arg
        275                 280                 285

Ser Glu Lys Glu Lys Ala Gln Asp Ala Leu Leu Val Thr Val Arg Ile
    290                 295                 300

Gly Thr Asp Trp Val Val Ile Asp Val Arg Gly Leu Leu Arg Asn Ala
305                 310                 315                 320

Arg Trp Arg Thr Ile Ala Pro Lys Asp Ile Ser Leu Asn Ala Leu Leu
                325                 330                 335

Asp Leu Phe Thr Gly Asp Pro Val Ile Asp Val Arg Arg Asn Ile Val
            340                 345                 350

Thr Phe Thr Tyr Thr Leu Asp Ala Cys Gly Thr Tyr Ala Arg Lys Trp
        355                 360                 365

Thr Leu Lys Gly Lys Gln Thr Lys Ala Thr Leu Asp Lys Leu Thr Ala
    370                 375                 380

Thr Gln Thr Val Ala Leu Val Ala Ile Asp Leu Gly Gln Thr Asn Pro
385                 390                 395                 400

Ile Ser Ala Gly Ile Ser Arg Val Thr Gln Glu Asn Gly Ala Leu Gln
                405                 410                 415

Cys Glu Pro Leu Asp Arg Phe Thr Leu Pro Asp Asp Leu Leu Lys Asp
            420                 425                 430

Ile Ser Ala Tyr Arg Ile Ala Trp Asp Arg Asn Glu Glu Glu Leu Arg
        435                 440                 445

Ala Arg Ser Val Glu Ala Leu Pro Glu Ala Gln Gln Ala Glu Val Arg
    450                 455                 460

Ala Leu Asp Gly Val Ser Lys Glu Thr Ala Arg Thr Gln Leu Cys Ala
465                 470                 475                 480
```

```
Asp Phe Gly Leu Asp Pro Lys Arg Leu Pro Trp Asp Lys Met Ser Ser
                485                 490                 495

Asn Thr Thr Phe Ile Ser Glu Ala Leu Leu Ser Asn Ser Val Ser Arg
            500                 505                 510

Asp Gln Val Phe Phe Thr Pro Ala Pro Lys Lys Gly Ala Lys Lys Lys
        515                 520                 525

Ala Pro Val Glu Val Met Arg Lys Asp Arg Thr Trp Ala Arg Ala Tyr
    530                 535                 540

Lys Pro Arg Leu Ser Val Glu Ala Gln Lys Leu Lys Asn Glu Ala Leu
545                 550                 555                 560

Trp Ala Leu Lys Arg Thr Ser Pro Glu Tyr Leu Lys Leu Ser Arg Arg
                565                 570                 575

Lys Glu Glu Leu Cys Arg Arg Ser Ile Asn Tyr Val Ile Glu Lys Thr
            580                 585                 590

Arg Arg Arg Thr Gln Cys Gln Ile Val Ile Pro Val Ile Glu Asp Leu
        595                 600                 605

Asn Val Arg Phe Phe His Gly Ser Gly Lys Arg Leu Pro Gly Trp Asp
    610                 615                 620

Asn Phe Phe Thr Ala Lys Lys Glu Asn Arg Trp Phe Ile Gln Gly Leu
625                 630                 635                 640

His Lys Ala Phe Ser Asp Leu Arg Thr His Arg Ser Phe Tyr Val Phe
                645                 650                 655

Glu Val Arg Pro Glu Arg Thr Ser Ile Thr Cys Pro Lys Cys Gly His
            660                 665                 670

Cys Glu Val Gly Asn Arg Asp Gly Glu Ala Phe Gln Cys Leu Ser Cys
        675                 680                 685

Gly Lys Thr Cys Asn Ala Asp Leu Asp Val Ala Thr His Asn Leu Thr
    690                 695                 700

Gln Val Ala Leu Thr Gly Lys Thr Met Pro Lys Arg Glu Glu Pro Arg
705                 710                 715                 720

Asp Ala Gln Gly Thr Ala Pro Ala Arg Lys Thr Lys Lys Ala Ser Lys
                725                 730                 735

Ser Lys Ala Pro Pro Ala Glu Arg Glu Asp Gln Thr Pro Ala Gln Glu
            740                 745                 750

Pro Ser Gln Thr Ser
        755


<210> SEQ ID NO 60
<211> LENGTH: 36
<212> TYPE: RNA
<213> ORGANISM: Unknown
<220> FEATURE:
<223> OTHER INFORMATION: bacteriophage

<400> SEQUENCE: 60

gucggaacgc ucaacgauug ccccucacga ggggac                              36


<210> SEQ ID NO 61
<211> LENGTH: 766
<212> TYPE: PRT
<213> ORGANISM: Unknown
<220> FEATURE:
<223> OTHER INFORMATION: bacteriophage

<400> SEQUENCE: 61

Met Glu Lys Glu Ile Thr Glu Leu Thr Lys Ile Arg Arg Glu Phe Pro
1               5                   10                  15
```

-continued

```
Asn Lys Lys Phe Ser Ser Thr Asp Met Lys Lys Ala Gly Lys Leu Leu
            20                  25                  30

Lys Ala Glu Gly Pro Asp Ala Val Arg Asp Phe Leu Asn Ser Cys Gln
        35                  40                  45

Glu Ile Ile Gly Asp Phe Lys Pro Pro Val Lys Thr Asn Ile Val Ser
    50                  55                  60

Ile Ser Arg Pro Phe Glu Glu Trp Pro Val Ser Met Val Gly Arg Ala
65                  70                  75                  80

Ile Gln Glu Tyr Tyr Phe Ser Leu Thr Lys Glu Glu Leu Glu Ser Val
                85                  90                  95

His Pro Gly Thr Ser Ser Glu Asp His Lys Ser Phe Phe Asn Ile Thr
            100                 105                 110

Gly Leu Ser Asn Tyr Asn Tyr Thr Ser Val Gln Gly Leu Asn Leu Ile
        115                 120                 125

Phe Lys Asn Ala Lys Ala Ile Tyr Asp Gly Thr Leu Val Lys Ala Asn
    130                 135                 140

Asn Lys Asn Lys Lys Leu Glu Lys Lys Phe Asn Glu Ile Asn His Lys
145                 150                 155                 160

Arg Ser Leu Glu Gly Leu Pro Ile Ile Thr Pro Asp Phe Glu Glu Pro
                165                 170                 175

Phe Asp Glu Asn Gly His Leu Asn Asn Pro Pro Gly Ile Asn Arg Asn
            180                 185                 190

Ile Tyr Gly Tyr Gln Gly Cys Ala Ala Lys Val Phe Val Pro Ser Lys
        195                 200                 205

His Lys Met Val Ser Leu Pro Lys Glu Tyr Glu Gly Tyr Asn Arg Asp
    210                 215                 220

Pro Asn Leu Ser Leu Ala Gly Phe Arg Asn Arg Leu Glu Ile Pro Glu
225                 230                 235                 240

Gly Glu Pro Gly His Val Pro Trp Phe Gln Arg Met Asp Ile Pro Glu
                245                 250                 255

Gly Gln Ile Gly His Val Asn Lys Ile Gln Arg Phe Asn Phe Val His
            260                 265                 270

Gly Lys Asn Ser Gly Lys Val Lys Phe Ser Asp Lys Thr Gly Arg Val
        275                 280                 285

Lys Arg Tyr His His Ser Lys Tyr Lys Asp Ala Thr Lys Pro Tyr Lys
    290                 295                 300

Phe Leu Glu Glu Ser Lys Lys Val Ser Ala Leu Asp Ser Ile Leu Ala
305                 310                 315                 320

Ile Ile Thr Ile Gly Asp Asp Trp Val Val Phe Asp Ile Arg Gly Leu
                325                 330                 335

Tyr Arg Asn Val Phe Tyr Arg Glu Leu Ala Gln Lys Gly Leu Thr Ala
            340                 345                 350

Val Gln Leu Leu Asp Leu Phe Thr Gly Asp Pro Val Ile Asp Pro Lys
        355                 360                 365

Lys Gly Val Val Thr Phe Ser Tyr Lys Glu Gly Val Val Pro Val Phe
    370                 375                 380

Ser Gln Lys Ile Val Pro Arg Phe Lys Ser Arg Asp Thr Leu Glu Lys
385                 390                 395                 400

Leu Thr Ser Gln Gly Pro Val Ala Leu Leu Ser Val Asp Leu Gly Gln
                405                 410                 415

Asn Glu Pro Val Ala Ala Arg Val Cys Ser Leu Lys Asn Ile Asn Asp
            420                 425                 430

Lys Ile Thr Leu Asp Asn Ser Cys Arg Ile Ser Phe Leu Asp Asp Tyr
```

-continued

```
        435                 440                 445

Lys Lys Gln Ile Lys Asp Tyr Arg Asp Ser Leu Asp Glu Leu Glu Ile
    450                 455                 460

Lys Ile Arg Leu Glu Ala Ile Asn Ser Leu Glu Thr Asn Gln Gln Val
465                 470                 475                 480

Glu Ile Arg Asp Leu Asp Val Phe Ser Ala Asp Arg Ala Lys Ala Asn
                485                 490                 495

Thr Val Asp Met Phe Asp Ile Asp Pro Asn Leu Ile Ser Trp Asp Ser
            500                 505                 510

Met Ser Asp Ala Arg Val Ser Thr Gln Ile Ser Asp Leu Tyr Leu Lys
        515                 520                 525

Asn Gly Gly Asp Glu Ser Arg Val Tyr Phe Glu Ile Asn Asn Lys Arg
    530                 535                 540

Ile Lys Arg Ser Asp Tyr Asn Ile Ser Gln Leu Val Arg Pro Lys Leu
545                 550                 555                 560

Ser Asp Ser Thr Arg Lys Asn Leu Asn Asp Ser Ile Trp Lys Leu Lys
                565                 570                 575

Arg Thr Ser Glu Glu Tyr Leu Lys Leu Ser Lys Arg Lys Leu Glu Leu
            580                 585                 590

Ser Arg Ala Val Val Asn Tyr Thr Ile Arg Gln Ser Lys Leu Leu Ser
        595                 600                 605

Gly Ile Asn Asp Ile Val Ile Ile Leu Glu Asp Leu Asp Val Lys Lys
    610                 615                 620

Lys Phe Asn Gly Arg Gly Ile Arg Asp Ile Gly Trp Asp Asn Phe Phe
625                 630                 635                 640

Ser Ser Arg Lys Glu Asn Arg Trp Phe Ile Pro Ala Phe His Lys Ala
                645                 650                 655

Phe Ser Glu Leu Ser Ser Asn Arg Gly Leu Cys Val Ile Glu Val Asn
            660                 665                 670

Pro Ala Trp Thr Ser Ala Thr Cys Pro Asp Cys Gly Phe Cys Ser Lys
        675                 680                 685

Glu Asn Arg Asp Gly Ile Asn Phe Thr Cys Arg Lys Cys Gly Val Ser
    690                 695                 700

Tyr His Ala Asp Ile Asp Val Ala Thr Leu Asn Ile Ala Arg Val Ala
705                 710                 715                 720

Val Leu Gly Lys Pro Met Ser Gly Pro Ala Asp Arg Glu Arg Leu Gly
                725                 730                 735

Asp Thr Lys Lys Pro Arg Val Ala Arg Ser Arg Lys Thr Met Lys Arg
            740                 745                 750

Lys Asp Ile Ser Asn Ser Thr Val Glu Ala Met Val Thr Ala
        755                 760                 765


<210> SEQ ID NO 62
<211> LENGTH: 36
<212> TYPE: RNA
<213> ORGANISM: Unknown
<220> FEATURE:
<223> OTHER INFORMATION: bacteriophage

<400> SEQUENCE: 62

accaaaacga cuauugauug cccaguacgc ugggac                            36
```

GENOMIC ALTERATION OF PLANT GERMLINE

CROSS-REFERENCE TO RELATED APPLICATIONS

This international patent application claims the benefit of U.S. provisional patent application No. 62/924,542, filed Oct. 22, 2019 and incorporated herein by reference in its entirety.

ELECTRONICALLY REFERENCE TO SEQUENCE LISTING SUBMITTED ELECTRONICALLY

The content of the electronically submitted sequence listing in ASCII text file (Name: 10068_SEQ LST_ST25.txt; Size: 102655 bytes; and Date of Creation: Oct. 22, 2020) filed with the application is incorporated herein by reference in its entirety.

BACKGROUND

Development of new and improved varieties of plants requires a genetically diverse parental pool. Traditional breeding programs are based on genetic variation that originates from exotic germplasm or from random mutagenesis. Selected individuals with potentially advantageous genetic traits are backcrossed into elite germplasm to develop improved varieties.

With a growing understanding of plant genetics, many targets emerge for possible genetic modifications useful in making improved plant varieties. Yet traditional methods of random mutagenesis are time consuming and do not provide a convenient way to explore the full spectrum of potential benefit of genetic variation of candidate loci. Other methods like transgenesis or genome editing are more promising.

A drawback of specific genomic intervention, such as by genome editing, is our limited current ability to directly modify the genome of elite germplasm of the species of interest. Genome editing reagents are most often delivered to transformable rather than elite germplasm, which needs to be followed by prolonged backcrossing into commercial germplasm before the phenotypic impact of individual edits can be assessed. The editing methods often require tissue culture and plant regeneration, which requires specific skills and equipment, and adds significant time and expense to the entire process. The methods are very complicated for most plant species, sometimes requiring use of morphogenic regulators to facilitate successful gene editing reagent delivery using biolistic- or Agrobacterium-mediated methods. This is followed by a long process of selecting the putative edited cells and regenerating the edited plants via a complex tissue culture process that is specific to each genotype for plant species of interest. The dedifferentiation required to produce regenerable callus using tissue culture often triggers seemingly random epigenetic modifications, which further complicates any phenotypic analyses of primary transformants and their progeny.

A need remains for robust and efficient reagents and methods for performing targeted genetic editing in plants. Ideally, the solutions are broadly applicable or easily adaptable to different species and varieties within each species. Bypassing callus induction and/or tissue culture is preferable, to reduce the time and resources required to produce edited events and to produce many targeted genetic variants plus their combinations in all relevant elite genetic backgrounds.

SUMMARY

The solutions described here relate to engineered RNA molecules useful in producing plants with altered genomes. As such, it relates to substantially purified compositions, vectors, systems, as well as methods, seeds, pollen, and plants useful at various steps in altering genomes of plants.

In their use, the RNA molecules are often needed in a substantially purified form. The RNAs are generally chimeric, meaning that they are made up of at least two different fused segments. One segment comprises a cargo RNA sequence, and another segment comprises a meristem transport RNA sequence.

The cargo segment is made up of RNA that, once inside meristematic cells, carries out the genome alteration function. In various embodiments, the cargo segment can be made up one or more of different sequences needed for the assembly in the plant cell cytosol of the genome-altering function, i.e. it has one or more DNA-modifying components. The DNA modifying components are typically RNA-guided nuclease components, RNAi, a TALE, zinc finger, or meganuclease sequences. RNA-guided nuclease systems typically require at least one polypeptide nuclease effector and one or more guide RNAs. In some embodiments, the cargo segment has an expressible coding sequence of a polypeptide nuclease effector (e.g. Cas9, Cas12a, or Cas12i), such that the RNA is translated when inside a plant cell. In some embodiments, the cargo segment comprises guide RNAs that are flanked by processing elements designed so that, within a plant cell cytosol, they are excised from the chimeric molecule and function in conjunction with a polypeptide nuclease effector present in the same cell. In some embodiments, the same RNA molecule comprises both the effector polynucleotide-encoding sequence and one or more guide RNAs. In these cases, the guide RNA processing elements can be made up of direct repeat sequences of the bacterial CRISPR array of the RNA-guided polypeptide.

The meristem transport segment is made up of a sequence that allows for transport of a chimeric RNA through the plant (e.g., through the phloem of the vascular system) and into the meristem tissues or meristem cells. The transport segment sequence can occur in any RNA found in the plant vascular system that transits from the tissue/cell of origin to the meristem. In one embodiment, the transport segment sequence is generally based on Flowering Time (FT) genes of plants, and they sometimes correspond to fragments of FT transcripts. Flowering Time (FT) gene products are also referred to as "florigen." The chimeric RNAs are often arranged so that the meristem transport segment is often located 3' of the cargo segment. In another embodiment, the chimeric RNAs are arranged so that the meristem transport segment (MTS) is located 3' of the protein coding segment (e.g., a segment encoding an RNA-guided nuclease) in the chimeric RNA.

The RNAs can be used in methods of producing plants with altered genomes. Accordingly, a subj ect plant is contacted with RNAs as described, so that the RNAs typically reach the phloem of the plant. This step may be carried out at the vegetative stage of the plant life cycle. Germline cells of the treated plant and their progeny will have the genome alterations intended to be made by the introduced RNA. In certain embodiments, germline cells of the treated plant and their daughter cells will have the intended genome alterations encoded by the introduced RNA prior to transitioning to reproductive development.

In certain embodiments, a composition comprising a substantially purified RNA molecule made up of a cargo segment fused to a meristem transport segment is provided. In certain embodiments, the cargo segment comprises a DNA-modifying component. In certain embodiments, the DNA-modifying component is selected from an RNA-guided nuclease component, an RNAi, a TALE, a zinc finger, and a meganuclease. In certain embodiments, the RNA-guided nuclease component comprises an RNA-guided polypeptide encoding sequence. In certain embodiments, the RNA-guided polypeptide encoding sequence can be translated if present in a plant cell cytosol. In certain embodiments, the meristem transport segment comprises an FT-derived sequence. In certain embodiments, the FT-derived sequence is a fragment of an FT transcript. In certain embodiments, the meristem transport segment is located 3' of the cargo segment. In any of the aforementioned embodiments, the composition further comprise RNase inhibitors. A method of producing a plant with an altered genome, comprising contacting a plant with any of the aforementioned compositions, and retrieving a progeny of the plant, wherein the progeny has an altered genome is provided. In certain embodiments, the contacting comprises phloem loading. In certain embodiments, the contacting with the composition occurs at the vegetative stage of the plant life cycle. Also provided are plants made by the method of producing a plant with an altered genome, comprising contacting a plant with any of the aforementioned compositions, and retrieving a progeny of the plant, wherein the progeny has an altered genome.

A meristem-delivery vector made up of a chimeric RNA having an RNA-guided nuclease component-containing segment and a meristem transport segment is provided.

A recombinant DNA having a sequence capable of producing as a transcript a meristem-delivery vector made up of a chimeric RNA having an RNA-guided nuclease component-containing segment and a meristem transport segment or an RNA that can be purified to form a composition comprising a substantially purified RNA molecule made up of a cargo segment fused to a meristem transport segment is provided.

Also provided are compositions comprising at least one RNA molecule comprising a cargo segment fused to a meristem transport segment (MTS), wherein the cargo segment comprises one or more guide RNAs for an RNA-guided nuclease. Use of the compositions to obtain a plant with an altered genome are provided.

Methods of producing a plant with an altered genome comprising (i) contacting a plant with at least a first composition comprising a cargo segment fused to a meristem transport segment (MTS), wherein the cargo segment comprises one or more guide RNAs for an RNA-guided nuclease; and (ii) retrieving a progeny of the plant, wherein the progeny has an altered genome, are provided. Plants comprising an altered genome made by the method are also provided.

BRIEF DESCRIPTION OF THE DRAWINGS/FIGURES

FIG. 1A, B is a diagram of the primary structure of an embodiment of an RNA sequence useful in methods for plant genomic alterations. g=guide RNA. In certain embodiments, the g or guide RNA segment may be made up of a spacer complementary to its genome target, and a crRNA, which is part of the direct repeat sequences of Cas12a and/or Cas12j CRISPR arrays. The various labeled parts are not drawn to scale.

DETAILED DESCRIPTION

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "Cas12a" and "Cpf1" are used interchangeably herein to refer to the same grouping of RNA directed nucleases.

As used herein, the terms "Cas12j" and "CasΦ" are used interchangeably herein to refer to the same grouping of RNA directed nucleases.

The term "fragment" refers to a contiguous set of polynucleotides or polypeptides. In one embodiment, a fragment is at least 10, 15, 20, or greater than 20 contiguous nucleotides. In other embodiments, a fragment is at least 10, 15, 20, or 50 to about 70, 90, 100, 120, 150, or 200 or more continuous nucleotides.

The term "isolated" as used herein means having been removed from its natural environment.

As used herein, the terms "include," "includes," and "including" are to be construed as at least having the features to which they refer while not excluding any additional unspecified features.

As used herein, the phrase "operably linked" or "fused" refers to a juxtaposition wherein the components so described are in a relationship permitting them to function in their intended manner. For instance, a promoter is operably linked to a coding sequence if the promoter affects its transcription or expression. In another non-limiting example, an RNA molecule comprising a "meristem transport sequence" (MTS) is operably linked or fused to a cargo RNA molecule if the MTS provides for delivery of the cargo RNA to meristem cells.

As used herein, the terms "orthologous" or "orthologue" are used to describe genes or the RNAs or proteins encoded by those genes that are from different species but which have the same function (e.g., encode RNAs which exhibit the same meristem transport function). Orthologous genes will typically encode RNAs or proteins with some degree of sequence identity (e.g., at least 40%, 50%, 60%, 70%, 80%, 90%, or 95% sequence identity) and can also exhibit conservation of sequence motifs, and/or conservation of structural features including RNA stem loop structures.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The phrase "substantially purified," as used herein defines an isolation of a molecule or compound in a form that is substantially free of contaminants normally associated with the molecule or compound in a native or natural environment and means having been increased in purity as a result of being separated from other components of the original composition. The phrase "substantially purified RNA molecule" is used herein to describe an RNA molecule which has been separated from other contaminant compounds including, but not limited to polypeptides, lipids, and carbohydrates. In certain embodiments, a substantially purified RNA is at least 90%, 95%, 97%, 98%, 99%, 99.5%, or 99.9% free of contaminating compounds by weight. A substantially purified RNA molecule can be combined with other compounds including buffers, RNase inhibitors, surfactants, and the like in a composition.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

The reagents and methods described provide a relatively easy and convenient solution for producing plants with altered genomes, i.e. individuals with designed mutations (i.e., DNA sequence changes including insertions, deletions, and substitutions (Indels)). In most embodiments, the methods and systems rely on RNA molecules produced with established molecular biology techniques. The RNA molecules, which comprise genome-editing reagents, are then introduced into a plant and taken up into meristematic cells. The meristematic cell genomes are thus altered, and the mutations (i.e., DNA sequence changes including Indels) are carried into germline cells and subsequent generations.

Meristem transport segments travel through the plant, typically via the phloem, and are taken up into meristematic tissues. The examples below are sequences from individual species, which sometimes work across species. For example, Arabidopsis FT-based vectors work in Nicotiana benthamiana and Arabidopsis. But, vectors can be designed based on alternative sequences, which can be based either on the species subject to genomic editing, or based on a closely related species.

While the transport segment is based on a plant-transported RNA, its actual sequence may be a fragment determined by characterizing a deletion series to make a smaller sequence retaining the desired transport (phloem mobility and/or meristem cell translocation) capabilities. In certain embodiments, the meristem transport segment is a subfragment of a plant transported RNA identified by assaying a deletion series for a smaller sequence retaining the desired transport (phloem mobility and/or meristem cell translocation) function. The initiator methionine codon or translation initiation codon of the base sequence may also be mutated in some cases.

The flowering time (FT) mRNA is useful as a meristem transport segment. SEQ ID NO: 2 shows the DNA sequence that encodes the Arabidopsis FT RNA, and SEQ ID NO: 1 is a fraction of SEQ ID NO: 2 that encodes the RNA that functions as a transport segment. Alternative useful FTs may be ZCN8 (encoded by SEQ ID NO: 3), which may work across related monocot species. Alternative useful FTs may be GmFT2a (Sun et al. PLoS One. 2011; 6(12):e29238. doi:10.1371/journal.pone.0029238; Jiang et al. BMC Genomics. 2019; 20(1):230. doi: 10.1186/s12864-019-5577-5; Kong et al. Plant Physiol. 2010 November; 154(3): 1220-31. doi: 10.1104/pp.110.160796; Takeshima et al. J Exp Bot. 2019 Aug. 7; 70(15):3941-3953. doi: 10.1093/jxb/erz199), which may work across related dicot species. FT RNA molecules that can be used include: (i) RNAs set forth in SEQ ID NO: 5, 6, 7, 8, 9, 10, 11, 12, 13, 14, 15, 16, 17, 18, 19, 20, 21, 22, 23, or 24, a meristem transport-competent (MTC) ortholog thereof, a MTC variant thereof, and/or a MTC fragment thereof; (ii) allelic variants of SEQ ID NO: 5, 6, 7, 8, 9, 10, 11, 12, 13, 14, 15, 16, 17, 18, 19, 20, 21, 22, 23, or 24, a meristem transport-competent (MTC) ortholog thereof, a MTC variant thereof, and/or a MTC fragment thereof; and (iii) FT RNAs from various plants set forth in U.S. 20190300890, which is incorporated herein by reference in its entirety, allelic variants thereof, and meristem transport-competent (MTC) orthologs thereof, MTC variants thereof, and/or MTC fragments thereof. FT RNA molecules that can be used include RNAs having at least 85%, 90%, 95%, 98%, or 99% sequence identity to SEQ ID NO: 5, 6, 7, 8, 9, 10, 11, 12, 13, 14, 15, 16, 17, 18, 19, 20, 21, 22, 23, 24, or a meristem transport-competent (MTC) fragment thereof;

More generally, viral and cellular-derived RNA molecules that are useful as part of a transport segment include the mRNAs of FT, GAI, CmNACP, LeT6 a tomato KNOX gene, BEL5, or tRNA-like sequences (Ruiz-Medrano et al., 1999 Phloem long-distance transport of CmNACP mRNA: implications for supracellular regulation in plants. Development 126, 4405-4419; Kim et al., 2001 Developmental changes due to long-distance movement of a homeobox fusion transcript in tomato. Science 293, 287-289; Haywood et al., 2005 Phloem long distance trafficking of GIBBERELLIC ACID-INSENSITIVE RNA regulates leaf development. Plant J. 42, 49-68; and Li et al., 2011 Mobile FT mRNA contributes to the systemic florigen signaling in floral induction. Sci. Rep. 1, 73; Cho et al., 2015, J. Exp. Bot, 66: 6835-6847; Zhang et al., 2016, Plant Cell, 28: 1237-1249; and WO2017178633). GAI RNAs that can be used include: (i) RNAs set forth in SEQ ID NO: 26, a meristem transport-competent (MTC) ortholog thereof, a MTC variant thereof, and/or a MTC fragment thereof; (ii) allelic variants of SEQ ID NO: 26, a meristem transport-competent (MTC) ortholog thereof, a MTC variant thereof, and/or a MTC fragment thereof; and (iii) RNAs having at least 85%, 90%, 95%, 98%, or 99% sequence identity to SEQ ID NO: 26, or a meristem transport-competent (MTC) fragment thereof. CmNACP RNAs that can be used include: (i) RNAs set forth in SEQ ID NO: 25, a meristem transport-competent (MTC) ortholog thereof, a MTC variant thereof, and/or a MTC fragment thereof; (ii) allelic variants of SEQ ID NO: 25, a MTC variant thereof, and/or a MTC fragment thereof; and (iii) RNAs having at least 85%, 90%, 95%, 98%, or 99% sequence identity to SEQ ID NO: 25, or a meristem transport-competent (MTC) fragment thereof. LeT6 RNAs that can be used include: (i) RNAs set forth in SEQ ID NO: 27, a meristem transport-competent (MTC) ortholog thereof, a MTC variant thereof, and/or a MTC fragment thereof; (ii) allelic variants of SEQ ID NO: 27, a MTC variant thereof, and/or a MTC fragment thereof; and (iii) RNAs having at least 85%, 90%, 95%, 98%, or 99% sequence identity to SEQ ID NO: 27, or a meristem transport-competent (MTC) fragment thereof. BEL5 RNAs that can be used include: (i) RNAs set forth in SEQ ID NO: 28, a meristem transport-competent (MTC) ortholog thereof, a MTC variant thereof, and/or a MTC fragment thereof; (ii) allelic variants of SEQ ID NO: 28, a MTC variant thereof, and/or a MTC fragment thereof; and (iii) RNAs having at least 85%, 90%, 95%, 98%, or 99% sequence identity to SEQ ID NO: 28, or a meristem transport-competent (MTC) fragment thereof. Examples of tRNA-like RNAs that can be used include: (i) RNAs set forth in SEQ ID NO: 29, 30, a meristem transport-competent (MTC) ortholog thereof, a MTC variant thereof, and/or a MTC fragment thereof; (ii) allelic variants of SEQ ID NO: 29, 30, a MTC variant thereof, and/or a MTC fragment thereof, and (iii) RNAs having at least 85%, 90%, 95%, 98%, or 99% sequence identity to SEQ ID NO: 29, 30, or a meristem transport-competent (MTC) fragment thereof. In certain embodiments, a TLS sequence, SEQ ID NO: 29 or 30, a meristem transport-competent (MTC) ortholog thereof, a MTC variant thereof, and/or an MTC fragment thereof can comprise an RNA hairpin comprising a first stem of 8 to 12 nucleotides, at least one variable bulge, a second stem of 4 to 7 nucleotides, and a variable loop. TLS sequences suitable for RNA transport and the structural features of such RNAs are set forth in Zhang et al. Plant Cell. 2016 June; 28(6): 1237, doi.org/10.1105/tpc.15.01056.

Further description of biological sequences provided in the sequence listing is set forth in Table 1. RNA molecules set forth in SEQ ID NO: 9-30 are respectively encoded by the DNA molecules set forth in SEQ ID NO: 31-52.

TABLE 1

Description of biological sequences.

| SEQ ID NO: | TYPE | Comments |
|---|---|---|
| 1 | DNA | *Arabidopsis thaliana* |
| 2 | DNA | NM_001334207.1 *Arabidopsis thaliana* PEBP (phosphatidylethanolamine-binding protein) family protein (FT), mRNA |
| 3 | DNA | EU241924.1 *Zea mays* ZCN8 (ZCN8) mRNA, complete cds |
| 4 | DNA | GmFT2a CDS, the soy FT ortholog according to Sun et al., 2011 and Cai et al., 2018 (GenBank ID: EU287455) |
| 5 | RNA | RNA encoded by SEQ ID NO: 1 |
| 6 | RNA | RNA encoded by SEQ ID NO: 2 |
| 7 | RNA | RNA encoded by SEQ ID NO: 3 |
| 8 | RNA | RNA encoded by SEQ ID NO: 4 |
| 9 | RNA | DQ865290.1 *Cucurbita maxima* flowering locus T-like 1 (FTL1) mRNA, complete cds |
| 10 | RNA | DQ865291.1 *Cucurbita maxima* flowering locus T-like 2 (FTL2) mRNA, complete cds |
| 11 | RNA | DQ871590.1 *Vitis vinifera* FT-like protein (FT) mRNA, complete cds |
| 12 | RNA | AB161112.1 *Malus* x *domestica* MdFT1 mRNA for flowering locus T like protein, complete cds |
| 13 | RNA | AB027456.1 *Citrus unshiu* CiFT mRNA, complete cds |
| 14 | RNA | AY186735.1: 2002-2199, 2287-2348, 4490-4530, 5586-5818 *Lycopersicon esculentum* SP3D (SP3D) gene, complete cds |
| 15 | RNA | DQ387859.1 *Populus tremula* flowering locus T-like protein FT1 (FT1) mRNA, complete cds |
| 16 | RNA | >DQ100327.1: 1332-1532, 1950-2011, 2121-2391 *Hordeum vulgare* subsp. *vulgare* FT-like protein (FT1) gene, complete cds |
| 17 | RNA | DQ297407.1: 955-1164, 1235-1296, 3672-3712, 3808-4031 *Hordeum vulgare* subsp. *vulgare* FT-like protein (FT2) gene, complete cds |
| 18 | RNA | AB052944.1 *Oryza sativa* Japonica Group Hd3a mRNA, complete cds, cultivar: Nipponbare |
| 19 | RNA | AB062676.1 *Oryza sativa* Japonica Group RFT1 mRNA for FT-like protein, complete cds |
| 20 | RNA | EU178859.1 *Ipomoea nil* FT-like protein (FT1) mRNA, complete cds |
| 21 | RNA | AB027506.1 *Arabidopsis thaliana* TSF (TWIN SISTER OF FT) mRNA, complete cds |
| 22 | RNA | LC128590.1: 3049-3243, 3377-3438, 3830-3870, 4102-4322 *Glycine max* FT5a gene for flowering locus T, complete cds, cultivar: Toyoharuka |
| 23 | RNA | ZmZCN9 NM_001112777.2 *Zea mays* ZCN9 protein (LOC100127520), mRNA |
| 24 | RNA | ZmZCN10<br>>EU241926.1 *Zea mays* ZCN10 (ZCN10) mRNA, complete cds |
| 25 | RNA | CmNACP:<br>>FJ151402.1 *Cucurbita maxima* NAC-domain containing protein (NACP1) mRNA, complete cds |
| 26 | RNA | GAI:<br>>Y15193.1 *Arabidopsis thaliana* GAI gene |
| 27 | RNA | LeT6 a tomato KNOX gene:<br>>AF000141.1 *Lycopersicon esculentum* class I knotted-like homeodomain protein (LeT6) mRNA, complete cds |

TABLE 1-continued

Description of biological sequences.

| SEQ ID NO: | TYPE | Comments |
|---|---|---|
| 28 | RNA | BEL5: >NM_001287992.1 *Solanum tuberosum* BEL1-related homeotic protein 5 (BEL5), mRNA |
| 29 | RNA | AT5G57885.1 (tRNA-Met) |
| 30 | RNA | AT1G71700 (tRNA-Gly) |
| 31 | DNA | DQ865290.1 *Cucurbita maxima* flowering locus T-like 1 (FTL1) mRNA, complete cds |
| 32 | DNA | DQ865291.1 *Cucurbita maxima* flowering locus T-like 2 (FTL2) mRNA, complete cds |
| 33 | DNA | DQ871590.1 *Vitis vinifera* FT-like protein (FT) mRNA, complete cds |
| 34 | DNA | AB161112.1 *Malus* x *domestica* MdFT1 mRNA for flowering locus T like protein, complete cds |
| 35 | DNA | AB027456.1 *Citrus unshiu* CiFT mRNA, complete cds |
| 36 | DNA | AY186735.1: 2002-2199, 2287-2348, 4490-4530, 5586-5818 *Lycopersicon esculentum* SP3D (SP3D) gene, complete cds |
| 37 | DNA | DQ387859.1 *Populus tremula* flowering locus T-like protein FT1 (FT1) mRNA, complete cds |
| 38 | DNA | >DQ100327.1: 1332-1532, 1950-2011, 2121-2391 *Hordeum vulgare* subsp. *vulgare* FT-like protein (FT1) gene, complete cds |
| 39 | DNA | DQ297407.1: 955-1164, 1235-1296, 3672-3712, 3808-4031 *Hordeum vulgare* subsp. *vulgare* FT-like protein (FT2) gene, complete cds |
| 40 | DNA | AB052944.1 *Oryza sativa* Japonica Group Hd3a mRNA, complete cds, cultivar: Nipponbare |
| 41 | DNA | AB062676.1 *Oryza sativa* Japonica Group RFT1 mRNA for FT-like protein, complete cds |
| 42 | DNA | EU178859.1 *Ipomoea nil* FT-like protein (FT1) mRNA, complete cds |
| 43 | DNA | AB027506.1 *Arabidopsis thaliana* TSF (TWIN SISTER OF FT) mRNA, complete cds |
| 44 | DNA | LC128590.1: 3049-3243, 3377-3438, 3830-3870, 4102-4322 *Glycine max* FT5a gene for flowering locus T, complete cds, cultivar: Toyoharuka |
| 45 | DNA | ZmZCN9 NM_001112777.2 *Zea mays* ZCN9 protein (LOC100127520), mRNA |
| 46 | DNA | ZmZCN10 >EU241926.1 *Zea mays* ZCN10 (ZCN10) mRNA, complete cds |
| 47 | DNA | CmNACP: >FJ151402.1 *Cucurbita maxima* NAC-domain containing protein (NACP1) mRNA, complete cds |
| 48 | DNA | GAI: >Y15193.1 *Arabidopsis thaliana* GAI gene |
| 49 | DNA | LeT6 a tomato KNOX gene: >AF000141.1 *Lycopersicon esculentum* class I knotted-like homeodomain protein (LeT6) mRNA, complete cds |
| 50 | DNA | BEL5: >NM_001287992.1 *Solanum tuberosum* BEL1-related homeotic protein 5 (BEL5), mRNA |
| 51 | DNA | AT5G57885.1 (tRNA-Met) |
| 52 | DNA | AT1G71700 (tRNA-Gly) |
| 53 | PRO | FnCas12a (UniProtKB/Swiss-Prot: A0Q7Q2.1); US20160208243; and WO 2017/189308) |
| 54 | RNA | FnCas12aDR (Fonfara et al. Nature 532, 517-521 (2016). doi.org/10.1038/nature17945; US2016-0208243; WO 2017/189308) |
| 55 | PRO | LbCpfl (from Lachnospiraceae bacterium ND2006; UniProtKB: A0A182DWE3) |
| 56 | RNA | LbCpfl DR (from Lachnospiraceae bacterium ND2006; Zetsche et al., doi.org/10.1101/134015) |
| 57 | PRO | Cas12j-1protein (Pausch et al., 2020 Science 17 Jul. 2020: Vol. 369, Issue 6501, pp. 333-337) |
| 58 | RNA | Cas12j-2 DR sequence (Pausch et al., 2020 Science 17 Jul. 2020: Vol. 369, Issue 6501, pp. 333-337) |
| 59 | PRO | Cas12j-2 protein (Pausch et al., 2020 Science 17 Jul. 2020: Vol. 369, Issue 6501, pp. 333-337) |
| 60 | RNA | Cas12j-2 DR sequence (Pausch et al., 2020 Science 17 Jul. 2020: Vol. 369, Issue 6501, pp. 333-337) |
| 61 | PRO | Cas12j-3 protein (Pausch et al., 2020 Science 17 Jul. 2020: Vol. 369, Issue 6501, pp. 333-337) |
| 62 | RNA | Cas12j-3 DR sequence (Pausch et al., 2020 Science 17 Jul. 2020: Vol. 369, Issue 6501, pp. 333-337) |

The meristem transport-competence (MTC) potential can be determined for any variants, fragments, and/or orthologs of the aforementioned FT, GAI, CmNACP, LeT6 a tomato KNOX gene, BEL5, or tRNA-like RNAs. A side-by-side comparison with a known MTS as a positive control is useful. As such, a number of configurations can be used. One approach is to fuse candidate sequences to guide sequences of characterized editing potential for a species of interest. RNA sequences can be introduced into the phloem of an individual plant that expresses at least in the meristem a nuclease capable of associating with the guide sequence and producing the intended genomic alteration. The RNA sequences can be expressed in vitro, and introduced into the phloem as purified molecules. For example, a concentrated solution of RNA molecules of interest can be applied to a mechanically injured plant tissue, such as a cut or abraded leaf, stem, or meristem dome. RNAs can be coated on particles, such as micro or nano-scale particles such as gold or tungsten, for biolistic delivery. Alternatively, the RNA sequences could be incorporated into RNA viruses introduced in the plants (Jackson et al. 2012, Front. Plant Sci. 3, 127; Ali et al. 2015, Mol. Plant 8, 1288-1291; Cody et al. 2017 Plant Physiol. 175, 23-35; Ali et al. 2018, Virus Res. 244, 333-337; Gao et al. 2019, New Phytol. 223, 2120-2133). or the MTC can be assayed by introducing RNAs by grafting, i.e. the RNA molecules can be expressed in the rootstock of a grafted plant, and their effect observed in the scion (Zhang et al., 2016, Plant Cell, 28: 1237-1249; Huang et al, 2018, Plant Physiol. 178:783-794). MTS candidates can be assayed for longer and/or more complex RNA molecules, or mixtures of RNA molecules, that comprise not only guide or processable guide regions, but also nuclease-encoding sequences.

A clear readout of MTC is detection of the expected genomic alterations in progeny plants, which can be done by sequencing of the target genomic region, or even by whole genome sequencing. But alternative readouts can be designed that may be more convenient in some cases. For example, the guide sequences may be directed to disrupt or repair a reporter gene, such as a transgene encoding a fluorescent polypeptide. The expected genetic changes can then be evaluated in the treated plants by measuring changes in the reporter. Another convenient genomic alteration target in many species is phytoene desaturase (PDS), with the albino phenotype serving as a readout.

The cargo segments of the engineered RNA deliver the genome-editing components. In general, these will be based on CRISPR-Cas systems, but some alternatives are possible. The alternatives include RNAi for heritable knock-down as affected by DNA methylation status, a TALEN, a zinc finger nucleases (ZFN), and a meganuclease.

In certain embodiments, an RNA molecule comprising a RNA segment encoding a ZFN (e.g., a zinc finger nuclease or zinc finger nickase) that is operably linked to an RNA segment comprising an MTS to provide for ZFN-mediated gene editing in a plant meristem. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically Fokl). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8,12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fokl. This endonuclease must dimerize to cleave DNA. Thus, cleavage by Fokl as part of a ZFN requires two adjacent and independent binding events, which must occur in both the correct orientation and with appropriate spacing to permit dimer formation. The requirement for two DNA binding events enables more specific targeting of long and potentially unique recognition sites. Fokl variants with enhanced activities have been described and can be adapted for use in the methods described herein; see, e.g., Guo et al. (2010) J. Mol. Biol., 400:96-107.

In certain embodiments, an RNA molecule comprising a RNA segment encoding a TALEN (e.g., a TALE nuclease or nickase) that is operably linked to an RNA segment comprising an MTS to provide for TALEN-mediated gene editing in a plant meristem. Transcription activator like effectors (TALEs) are proteins secreted by certain Xanthomonas species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites.

TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) Genes vol. 8,12: 399). TALE nickases have also been described and can be adapted for use in methods described herein (Wu et al.; Biochem Biophys Res Commun. (2014); 446(1):261-6; Luo et al; Scientific Reports 6, Article No.: 20657 (2016)).

Plants comprising the RNA molecules that comprise cargo segments that are operably linked to MTS sequences are also provided herein. In certain embodiments, such RNA molecules will be present at detectable concentrations in the plants for only a certain period of time following. For example, the concentrations of RNA molecules comprising guide RNAs separated by processing elements comprising direct repeats (DR, i.e., pre-crRNAs comprising a full-length direct repeat (full-DR-crRNA)) which are capable of being processed (i.e., cleaved) by an RNA-guided nuclease are expected to decrease over time when the RNA-guided nuclease is also present in the plant. The concentrations of RNA molecules comprising guide RNAs separated by processing elements comprising direct repeats which are capable of being processed by an RNA-guided nuclease are also expected to be decreased in tissues where the RNA-guided nuclease is located. Nonetheless, the unprocessed RNA molecules can be detected by a variety of techniques that include reverse transcriptase PCR (RT-PCR) assays where oligonucleotide primers and optionally detection probes which specifically amplify and detect the unprocessed RNA molecule comprising the cargo segments that are operably linked to MTS sequences are used. Such plants can comprise any of the RNA molecules or combinations of RNA molecules present in the compositions provided herein that are used to contact the plants. In certain embodiments, an active form of the RNA guided nuclease is predominantly localized in meristem tissue of the plant. In certain embodiments, the RNA-guided nuclease can be encoded by an RNA molecule that is optionally further comprises an operably linked MTS sequence. In certain embodiments, the RNA-guided nuclease can be encoded by DNA that is operably linked to promoters that include a meristem-preferred or meristem-specific promoter which is active in meristem cells. DNA encoding the RNA-guided nuclease can be provided in a transgene that is stably integrated in the genome of the plant, in DNA that is not integrated into the plant genome, or in DNA provided in a viral vector (e.g., a geminivirus replicon). Geminivirus DNA replicons suitable for delivery of DNA molecules encoding an RNA-guided nuclease to plants include a Beet Yellow Dwarf Virus replicon (Baltes, Nicholas J. et al. Plant Cell vol. 26,1 (2014): 151-63. doi:10.1105/tpc.113.119792).

It is understood that for all systems, the use of a nuclease activity for cutting DNA followed by repair by the endogenous cell machinery is one solution to generate useful mutants. The nuclease activity can be eliminated or altered, as in dCas or nCas, TALE or ZF versions of the polypeptides. The inactivated nucleases can be useful for targeting the desired DNA sequence, while editing can be performed by nucleobase editors attached to the altered nucleases. Examples are included in WO2018176009 and U.S. Pat. No. 10,113,163, incorporated herein by reference.

CRISPR-based RNA-guided nuclease systems typically require an effector polypeptide, and one or more guide RNAs. The guide RNAs are generally made up of an effector-binding region and a target DNA recognition region, and in some embodiments include tracrRNAs. Useful CRISPR-based RNA-guided nuclease systems have been described and are known from the literature as Cas9, Cas12a (Cpf1), Cas12e (CasX), Cas12d (CasY), C2c1, C2c2, and C2c3, (see WO2018176009) Cas12h, Cas12i (see Yan et al. 2019, Science Vol. 363, Issue 6422, pp. 88-91) and Cas12j (Pausch et al., 2020 Science 17 Jul. 2020: Vol. 369, Issue 6501, pp. 333-337).

The Cas nuclease or effector polypeptide is intended to be translated inside a plant meristem cell. As such, it is typically embedded within an mRNA component. A 5' cap and polyA tail are also useful in stabilizing the RNA. A 5' UTR has translation initiation sequences upstream of the Cas coding sequence. For example, an mRNA can comprise a 5'UTR comprising a 7-methylguanosine cap at its 5' terminus followed by an untranslated sequence and terminated by the translation initiation codon of the coding sequence (e.g., the CAS coding sequence).

Cargo containing guide RNA can be part of the same RNA (mRNA) capable of expressing the Cas nuclease. In one embodiment, one or more guide RNAs are flanked by direct repeats (DR) of the CRISPR array from which the Cas effector polypeptide was first isolated. For example, a translated and expressed active Cas12a nuclease can process the DR-flanked spacers of the cargo RNA to make guide RNAs. In certain embodiments, a translated and expressed active Cas12j nuclease can process Cas12j DR-flanked spacers of the cargo RNA to make guide RNAs. Alternatively, guide RNA suitable for matching expressed effector polypeptide can be flanked by processing elements, so that functional guide RNAs are excised inside the cells. Exemplary processing elements include hammerhead ribozymes, Csy4, and tRNAs (see Mikami et al, Plant Cell Physiol. 2017 November; 58(11): 1857-1867, and U.S. Pat. No. 10,308,947).

In certain embodiments, an MTS is operably linked to a cargo segment comprising an array of a plurality of guide RNAs (e.g., 2, 3, 4, or more guide RNAs) separated by processing elements to provide for gene editing at a plurality of genomic locations targeted by each guide RNA. In certain embodiments, the plurality of guide RNAs are separated by processing elements comprising direct repeats (DR; i.e., pre-crRNAs comprising a full-length direct repeat (full-DR-crRNA)) which are capable of being processed (i.e., cleaved) by an RNA-guided nuclease. Examples of such DRs include the Cas12a DR (e.g., SEQ ID NO: 54 or 56) which can be cleaved by a Cas12a guided nuclease (e.g., SEQ ID NO: 53 or 55, respectively). Cleavage of RNAs comprising Cas12a DRs by Cas12a has been described (Fonfara et al. Nature 532, 517-521 (2016). doi.org/10.1038/nature17945); U.S. 20160208243; WO 2017/189308). Other examples of such DRs include the Cas12j DRs (e.g., SEQ ID NO: 58, 60, or 62) which can be cleaved by a Cas12j guided nuclease ((e.g., SEQ ID NO: 57, 59, or 61, respectively). In such embodiments, the crRNA portion of the DR can remain as a part of the gRNA after processing and can be recognized by the RNA guided nuclease to provide for editing of genomic DNA recognized via hybridization of the gRNA to the targeted genomic site.

Compositions comprising: (i) RNA molecules comprising an MTS is operably linked to a cargo segment; (ii) nucleic acids encoding RNA guided nucleases; and/or (iii) donor DNA templates can further comprise components that include:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; saponins or glycosylated triterpenoids or glycosylated sterols (e.g., saponin commercially available as catalogue number 47036-50 g-F, Sigma-Aldrich, St. Louis, MO); long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS No. 27306-78-1 and EPA Number CAL. REG. No. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents; buffers;

(g) peptides, proteins, or enzymes (e.g., cellulase, pectolyase, maceroenzyme, pectinase), including cell-penetrating or pore-forming peptides (e. g., (BO100)2K8, Genscript; poly-lysine, poly-arginine, or poly-homoarginine peptides; gamma zein, see U.S. Patent Application publication 2011/0247100, incorporated herein by reference in its entirety; transcription activator of human immunodeficiency virus type 1 ("HIV-1 Tat") and other Tat proteins, see, e. g., www[dot]lifetein[dot]com/Cell_Penetrating_Peptides[dot]html and Järver (2012) Mol. Therapy-Nucleic Acids, 1:e27, 1-17); octa-arginine or nona-arginine; poly-homoarginine (see Unnamalai et al. (2004) FEBS Letters, 566: 307-310); see also the database of cell-penetrating peptides CPPsite 2.0 publicly available at crdd[dot]osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e. g., PEI, branched, MW 25,000, CAS #9002-98-6; PEI, linear, MW 5000, CAS #9002-98-6; PEI linear, MW 2500, CAS #9002-98-6);

(j) dendrimers (see, e. g., U.S. Patent Application Publication 2011/0093982, incorporated herein by reference in its entirety);

(k) counter-ions, amines or polyamines (e. g., spermine, spermidine, putrescine), osmolytes, buffers, and salts (e. g., calcium phosphate, ammonium phosphate);

(l) polynucleotides (e. g., non-specific double-stranded DNA, salmon sperm DNA);

(m) transfection agents (e. g., Lipofectin®, Lipofectamine®, and Oligofectamine®, and Invivofectamine® (all from Thermo Fisher Scientific, Waltham, MA), PepFect (see Ezzat et al. (2011) Nucleic Acids Res., 39:5284-5298), TransIt® transfection reagents (Mirus Bio, LLC, Madison, WI), and poly-lysine, poly-homoarginine, and poly-arginine molecules including octo-arginine and nono-arginine as described in Lu et al. (2010) J. Agric. Food Chem., 58:2288-2294);

(n) antibiotics, including non-specific DNA double-strand-break-inducing agents (e. g., phleomycin, bleomycin, talisomycin);

(o) antioxidants (e. g., glutathione, dithiothreitol, ascorbate); and/or (p) chelating agents (e. g., EDTA, EGTA).

Compositions comprising: (i) RNA molecules comprising an MTS is operably linked to a cargo segment; (ii) nucleic acids encoding RNA guided nucleases; and/or (iii) donor DNA templates can be delivered to the plant and/or meristem cells of the plant by particle mediated delivery, and any other direct method of delivery, such as but not limiting to, Agrobacterium-mediated transformation, polyethylene glycol (PEG)-mediated transfection to protoplasts, whiskers mediated transformation, electroporation, particle bombardment, and/or by use of cell-penetrating peptides.

In certain embodiments, plants are contacted either simultaneously or sequentially with one, two, three or more RNA molecules in one or more compositions where at least one of the RNA molecules comprises an MTS operably linked to a cargo segment comprising at least one guide RNA. In certain embodiments, one of the RNA molecules comprises an MTS operably linked to a cargo segment comprising at least one guide RNA and the other RNA molecule encoding an RNA guided nuclease and optionally an MTS, where the RNA guided nuclease can process the RNA comprising the guide RNA to release a functional guide RNA. In certain embodiments, one of the RNA molecules comprises an MTS operably linked to a cargo segment comprising at least one guide RNA and the other RNA molecule comprises an RNA guided nuclease and optionally an MTS, where the RNA guided nuclease cannot process the RNA comprising the guide RNA to release a functional guide RNA (e.g., processing elements present in the RNA molecule comprising the gRNA and the MTS are not recognized by the RNA-guided nuclease). In certain embodiments, guide RNAs of the first and second RNA molecule are flanked by or comprise processing elements (e.g., DRs) which are processed by different RNA-guided nuclease (e.g., a Cas12a nuclease can process the first RNA molecule and a Cas12j nuclease can process the second RNA molecule). In certain embodiments, the cargo segment of the first RNA molecule comprises guide RNAs which are distinct from the guide RNAs of the cargo segment second RNA molecule. Such distinct gRNAs provided by the first RNA molecule can provide for genome editing at one or more first genomic sites in a meristem cell while the distinct gRNAs provided by the second RNA molecule can provide for genome editing at one or more second genomic sites in a meristem cell. Such contacting the plant with RNA molecules in a composition can occur sequentially such that the first gRNA(s) are delivered, allowed sufficient time (e.g., about 6, 12, 18 or 20 to about 24, 30, or 36 hours) to effect desired genome edits, followed by contacting the plant with the second RNA molecules in a second composition to deliver the second gRNA(s) to effect additional desired genome edits, where such desired genome edits are effected by providing the gRNA(s) and an RNA guided nuclease in at least the meristem cell. Without seeking to be limited by theory, it is believed that cutting chromosomes at multiple location simultaneously is cytotoxic and that such cytotoxicity can be mitigated by delivering a limited number of guide RNAs at different times (e.g., about 6, 12, 18 or 20 to about 24, 30, or 36 hours apart). In certain embodiments, a plant can be contacted by one or more RNA molecules that comprise at least one gRNA operably linked to an MTS, optionally along with an RNA encoding RNA guided nuclease, permitted a sufficient period of time to accumulate the RNA molecule in the meristem cells (e.g., about 6, 12, 18 or 20 to about 24, 30, or 36 hours apart), and then contacted with a different mixture of one or more RNA molecules that comprise at least one different gRNA operably linked to an MTS, optionally along with an RNA encoding RNA guided nuclease, where the RNA guided nuclease can process the RNA comprising the guide RNA to release a functional guide RNA and/or effect a desired genomic edit with the gRNA in the meristem cells.

In certain embodiments, the RNA molecules comprising at least one gRNA fused to an MTS are provided in combination with the RNA guided nuclease and a donor DNA template to effect insertions of DNA elements in the donor DNA template at the target editing site in the plant genome by homology dependent repair (HDR), non-homologous end joining (NHEJ), or microhomology-mediated end joining (MMEJ). Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In one embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 1, 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand of the targeted integration site (in the case of a perfectly base-paired double-stranded polynucleotide molecule). Such donor DNA templates can be integrated in genomic DNA containing blunt and/or staggered double stranded DNA breaks by homology-directed repair (HDR) or microhomology-mediated end joining (MMEJ). In certain embodiments, a donor DNA template homology arm can be about 20, 50, 100, 200, 400, or 600 to about 800, or 1000 base pairs in length. In certain embodiments, a donor DNA template molecule can be delivered to a plant cell in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. In other embodiments, DNA templates suitable for NHEJ insertion will lack homology arms that are partially or completely homologous to genomic DNA (gDNA) sequences flanking a target site-specific endonuclease cleavage site in the gDNA. Compositions comprising the donor templates can be delivered to the plant and/or meristem cells of the plant by particle mediated delivery, and any other direct method of delivery, such as but not limiting to, Agrobacterium-mediated transformation, polyethylene glycol (PEG)-mediated transfection to protoplasts, whiskers mediated transformation, electroporation, particle bombardment, and/or by use of cell-penetrating peptides. The donor DNA templates may be present transiently in the cell or it could be introduced via a viral replicon (e.g, a geminivirus replicon). Geminivirus DNA replicons suitable for delivery of donor DNA templates to plants include a Beet Yellow Dwarf Virus replicon (Baltes, N.J. et al. Plant Cell vol. 26,1(2014): 151-63. doi:10.1105/tpc.113.119792).

RNA guided nucleases can be provided to at least the meristem cell by a variety of methods that include stable expression with an integrated transgenes, expression from a viral vector, or transient expression such as by introducing an RNA that encodes the RNA guided nuclease or an that RNA that encodes the RNA guided nuclease that is operably linked an MTS. In certain embodiments, an active form of the RNA guided nuclease is predominantly localized in meristem tissue of the plant. Delivery of RNAs encoding the RNA guided nucleases or DNAs then encode those RNAs to the plant and/or meristem cells of the plant can be achieved by particle mediated delivery, and any other direct method of delivery, such as but not limiting to, Agrobacterium-mediated transformation, polyethylene glycol (PEG)-mediated transfection to protoplasts, whiskers mediated transformation, electroporation, particle bombardment, and/or by use of cell-penetrating peptides. In certain embodiments, such predominant localization of the RNA guided nuclease can result in at least about 60%, 70%, 80%, 90%, 95%, 98%, or 99% of the active form of the RNA guided nuclease in the plant being localized in the meristem. In certain embodiments, the nucleic acid encoding the RNA guided nuclease can be delivered directly to the meristem by methods that include use of biolistic devices (e.g., as in U.S. 20200123554). In certain embodiments, the RNA guided nuclease can be operably linked to a vegetative stage, meristem-preferred or meristem-specific promoter including: (i) a pAt.Erecta, At.PNH, At.AN3, or At.MYB17 promoter or functional fragment thereof from Arabidopsis; (ii) a promoter or functional fragment thereof from a Glyma10g38730, Glyma09g27950, Glyma06g05900, or Glyma17g34380 soybean gene; or (iii) receptor like kinase (RLK) gene promoters from a PGSC0003DMP400032802 or PGS C0003DMP400054040 gene of potato. Such vegetative stage, meristem-preferred or meristem-specific promoters are set forth in U.S. 20190300890, which is incorporated herein by reference in its entirety. In certain embodiments, expression of the RNA guided nuclease can increased in floral meristems of maize plants by operable linkage to a floral meristem-enhanced promoters that include Zap1a, Zap1b, ZLF1, ZLF2, or ZMM4 endogenous genes (Dong et al. 2012 PLoS ONE 7(8):e43450). Alternatively, the RNA guided nuclease can be expressed meristems and tissues other than the vascular tissues to mitigate cleavage of an RNA molecule comprising the gRNA and the MTS during transit from the site of contact to the meristem.

In some embodiments, a plant expressing transgenically a Cas polypeptide may be genome edited by delivery of a cargo containing only guide RNAs suitable for the transgenically expressed Cas polypeptide.

The RNA sequences are generally made and assembled at first in DNA form as RNA expressing vectors using recombinant DNA technology. RNA expression is done in vitro, and purified according to well established methods. Addition of RNA 5' caps and polyA tails to mRNAs can be performed according to methods established in the literature. Alternatively, some RNAs designed as described can be purchased from commercial providers.

A substantially purified RNA composition is understood to comprise a high concentration of an RNA molecule of interest, although in some cases it may comprise two distinct RNAs. For example, one RNA may comprise a Cas nuclease while another may comprise a corresponding guide or guide array. In addition, a substantially purified RNA composition may comprise other added components, such as a pH buffer, salt, surfactants, and/or RNase inhibitors.

Plants can be effectively contacted with the RNA vectors in many ways. Often it will be convenient to load them into the phloem of plants through the leaves, for example by nicking a leaf and submerging the injured tissue into a solution of substantially purified RNAs. Other avenues are also possible, such as by injection into the stems with a needle or use of a handheld biolistics device. In some embodiments, a surfactant is added to the purified RNA, and the liquid is applied to a tissue like embryonic shoot, leaf, stem, or inflorescence, with or without slight injury such as scratching.

The RNAs are often applied at the vegetative stage of the life cycle of a plant, so as to reach vegetative meristems before they convert to floral meristems. In some cases, however, it may be convenient to apply the vectors, RNA molecules, or compositions comprising the RNA molecules or vectors, to floral meristems, especially at early stages of differentiation. In certain embodiments, a soybean plant is contacted at the vegetative stage with a composition comprising the RNA molecules or vectors at vegetative stage Ve, V1, or V2 to about the V4 V(n) stage where 1, 2, 3, 4, or n is the number of trifoliate leaves (Soybean Growth and Development, M. Licht, 2014, Iowa State University Extension and Outreach, PM 1945). In certain embodiments, a maize plant is contacted at the vegetative stage with a composition comprising the RNA molecules or vectors at vegetative stage Ve, V1, or V2 to about the V4 V(n) stage (Corn Growth Stages, M. Licht, Iowa State University Extension and Outreach, on the https interne site "crops.extension.iastate.edu/encyclopedia/corn-growth-stages").

Very often, mutated seeds from plants edited with the reagents and methods described here are collected for phenotypic characterization. In some cases, pollen from edited plants is used in crosses with other individuals, or mutated individuals are pollinated with pollen of unedited plants or wildtype plants.

There are numerous plant-endogenous targets (i.e., DNA sequence targets) for genome editing. Any defective allele found in elite germplasm can get edited to a non-deleterious version. The methods presented here can be applied to a promoter bashing or fine-tuning approach, to create a range of phenotypes based on promoter alterations of a gene of a certain sequence or gene of interest (Rodriguez-Leal et al., Cell. 2017 Oct. 5; 171(2):470-480).

Editing of coding sequences can be made using the methods disclosed herein to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) Proceedings of the World Congress on Vegetable Protein Utilization in Human Foods and Animal Feedstuffs, ed. Applewhite (American Oil Chemists Society, Champaign, Ill.), pp. 497-502; herein incorporated by reference); corn (Pedersen et al. (1986) J. Biol. Chem. 261:6279; Kirihara et al. (1988) Gene 71:359; both of which are herein incorporated by reference); and rice (Musumura et al. (1989) Plant Mol. Biol. 12:123, herein incorporated by reference). Other agronomically important genes encode latex, Floury 2, growth factors, seed storage factors, and transcription factors.

The methods disclosed herein can be used to modify herbicide resistance traits including genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron. Additional herbicide resistance traits are described for example in U.S. Patent Application 2016/0208243, herein incorporated by reference.

Sterility genes can also be modified and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development. Additional sterility traits are described for example in U.S. Patent Application 2016/0208243, herein incorporated by reference.

Genome editing can also be used to make haploid inducer lines as disclosed in WO2018086623 and U.S. 20190292553.

The quality of grain can be altered by modifying genes encoding traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be altered by modifying a gene or that could increase for example, starch for ethanol production, or provide expression of proteins. Another important commercial use of modified plants is the production of polymers and bioplastics such as described in U.S. Pat. No. 5,602,321. Genes such as .beta.-Ketothiolase, PHBase (polyhydroxyburyrate synthase), and acetoacetyl-CoA reductase (see Schubert et al. (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The methods disclosed herein can also be used for modification of native plant gene expression to achieve desirable plant traits. Such traits include, for example, disease resistance, herbicide tolerance, drought tolerance, salt tolerance, insect resistance, resistance against parasitic weeds, improved plant nutritional value, improved forage digestibility, increased grain yield, cytoplasmic male sterility, altered fruit ripening, increased storage life of plants or plant parts, reduced allergen production, and increased or decreased lignin content. Genes capable of conferring these desirable traits are disclosed in U.S. Patent Application 2016/0208243, herein incorporated by reference.

The present disclosure may be used for genomic editing of any plant species, including, but not limited to, monocots and dicots (i.e., *monocotyledonous* and *dicotyledonous*, respectively). Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), camelina (*Camelina sativa*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), quinoa (*Chenopodium quinoa*), chicory (*Cichorium intybus*), lettuce (*Lactuca sativa*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

The embodiments described methods and reagents can have many advantages over other known solutions. The techniques presented generally bypass callus induction or tissue culture that are necessary for alternative or widely practiced genome editing procedures, thus speeding up (i.e., accelerating) and lowering or reducing the cost of the process of producing plants with targeted mutations. Epigenetic resetting (i.e., interference) is also eliminated. The editing can be performed in individuals of an elite genetic background, making lengthy backcrossing schemes unnecessary.

Embodiments

Various embodiments of the compositions, vectors, recombinant DNAs, RNAs, and methods provided herein are set forth in the following set of numbered embodiments.

1. A composition comprising at least one RNA molecule comprising a cargo segment fused to a meristem transport segment (MTS), wherein the cargo segment comprises one or more guide RNAs for an RNA-guided nuclease or wherein the cargo segment comprises RNA encoding a TALEN or ZFN protein.

2. The composition according to embodiment 1, wherein the guide RNA is flanked by or comprises processing elements.

3. The composition according to embodiment 2, wherein the processing elements are direct repeat sequences of the bacterial CRISPR array of the RNA-guided nuclease or are direct repeat sequences that are processed by the RNA-guided nuclease.

4. The composition according to embodiment 3, wherein the cargo segment comprises a plurality of guide RNAs.

5. The composition according to embodiments 3 or 4, wherein the guide RNAs and the direct repeat sequences of the bacterial CRISPR array are for a Cas12a or a Cas12j RNA-guided nuclease.

6. The composition according to embodiment 1, wherein the composition comprises both a first and a second RNA molecule each comprising a cargo segment fused to an MTS, wherein the cargo segment of the first RNA molecule comprises guide RNAs which are distinct from the guide RNAs of the second RNA molecule, optionally wherein the guide RNAs of the first and second RNA molecule are flanked by or comprise processing elements which are processed by different RNA-guided nucleases.

7. The composition according to any one of embodiments 1 to 6, wherein the cargo segment does not contain an RNA-guided nuclease polypeptide-encoding sequence.

8. The composition according to any one of embodiments 1 to 6, wherein the cargo segment further comprises an RNA-guided nuclease polypeptide-encoding sequence.

9. The composition according to embodiment 8, wherein RNA-guided nuclease polypeptide-encoding sequence can be translated in a plant cell cytosol.

10. The composition according to embodiment 8 or 9, wherein the RNA molecule further comprises at least one polyA region, wherein the polyA region is 3' of the RNA-guided nuclease polypeptide-encoding sequence, and 5' of the guide RNA and/or wherein the polyA region is at the 3' end of the RNA molecule.

11. The composition according to any one of embodiments 1 to 10, wherein the composition comprises both a first and a second RNA molecule each comprising a cargo segment fused to an MTS, wherein at least the first RNA molecule comprises a cargo sequence further comprising an RNA-guided nuclease polypeptide-encoding sequence, wherein the cargo segment of the first RNA molecule comprises guide RNAs which are distinct from the guide RNAs of the second RNA molecule.

12. The composition according to embodiment 11, wherein the guide RNAs of the first and second RNA molecule are flanked by or comprise processing elements which are processed by different RNA-guided nucleases, and optionally wherein the processing elements in the first RNA molecule are not recognized by the RNA-guided nuclease polypeptide encoded by the first RNA molecule.

13. The composition according to any one of embodiments 1 to 12, wherein the MTS comprises:

(i) a Flowering Time (FT)-derived sequence, optionally wherein the FT-derived sequence is SEQ ID NO: 5, 6, 7, 8, 9, 10, 11, 12, 13, 14, 15, 16, 17, 18, 19, 20, 21, 22, 23, or 24, a meristem transport-competent (MTC) ortholog thereof, a MTC variant thereof, and/or a MTC fragment thereof;

(ii) a tRNA like sequence (TLS), optionally wherein the TLS sequence comprises SEQ ID NO: 29 or 30, a meristem transport-competent (MTC) ortholog thereof, a MTC variant thereof, MTC fragment thereof, and/or an RNA hairpin comprising a first stem of 8 to 12 nucleotides, at least one variable bulge, a second stem of 4 to 7 nucleotides, and a variable loop;

(iii) a GAI sequence, optionally wherein the GAI sequence comprises SEQ ID NO: 26, a meristem transport-competent (MTC) ortholog thereof, a MTC variant thereof, and/or a MTC fragment thereof, (iv) a BEL5 sequence optionally wherein the BEL5 sequence comprises SEQ ID NO: 28, a meristem transport-competent (MTC) ortholog thereof, a MTC variant thereof, and/or a MTC fragment thereof;

(v) a CmNACP sequence optionally wherein the CmNACP sequence comprises SEQ ID NO: 25, a meristem transport-competent (MTC) ortholog thereof, a MTC variant thereof, and/or a MTC fragment thereof; or (vi) a LeT6 sequence optionally wherein the LeT6 sequence comprises SEQ ID NO: 27, a meristem transport-competent (MTC) ortholog thereof, a MTC variant thereof, a MTC fragment thereof.

14. The composition according to embodiment 13, wherein the MTS comprises a Flowering Time (FT)-derived sequence of SEQ ID NO: 5, 6, 7, 8, 9, 10, 11, 12, 13, 14, 15, 16, 17, 18, 19, 20, 21, 22, 23, 24, or a meristem transport-competent (MTC) fragment thereof.

15. The composition according to any one of embodiments 1 to 14, wherein the MTS is located 3' of the cargo segment.

16. The composition according to any of embodiments 1 to 15, further comprising RNase inhibitors.

17. The composition according to any one of embodiments 1 to 16, wherein the RNA molecule is a substantially purified RNA molecule.

18. The composition according to any one of embodiments 1 to 17, wherein the RNA molecule is not operably linked to a viral vector RNA and/or associated with a viral protein.

19. A meristem-delivery vector comprising a cargo segment fused to a meristem transport segment (MTS), wherein the cargo segment comprises one or more guide RNAs for an RNA-guided nuclease.

20. A recombinant DNA having a sequence capable of producing as a transcript a vector according to embodiment 19, or producing an RNA that can be purified and combined with one additional component to form a composition according to any one of embodiments 1 to 18.

21. A method of producing a plant with an altered genome comprising (i) contacting a plant with at least a first composition according to any of embodiments 1 to 18, and (ii) retrieving a progeny of the plant, wherein the progeny has an altered genome.

22. The method according to embodiment 21, wherein contacting comprises phloem loading.

23. The method according to embodiment 21 or 22, wherein the contacting with the composition occurs at the vegetative stage of the plant life cycle.

24. The method according to any one of embodiments 21 to 23, wherein contacting comprises contacting the plant with the first composition, and after a time interval contacting the plant with a second composition according to any one of embodiments 1 to 18, wherein the guide RNAs in the cargo segment of the RNA molecule in the first composition are different than the guide RNAs in the second cargo segment of the RNA molecule in the second composition.

25. The method according to embodiment 24, wherein the time interval is about 18 or 20 to about 24, 30, or 36 hours.

26. The method according to any one of embodiments 21 to 25, wherein the guide RNA(s) of the RNA molecule are flanked by or comprise processing elements which are processed by the RNA-guided nuclease.

27. The method according to any one of embodiments 21 to 26, wherein:

(i) wherein the RNA molecule does not contain an RNA-guided nuclease polypeptide-encoding sequence; and (ii) wherein the plant comprises a polynucleotide encoding the RNA-guided nuclease, optionally wherein the polynucleotide is integrated into the genome of the plant and/or optionally wherein an active form of the RNA guided nuclease is predominantly localized in meristem tissue of the plant.

28. The method of embodiment 27, wherein the RNA-guided nuclease is encoded by a DNA molecule, optionally wherein the DNA molecule is integrated into the genome of the plant, optionally wherein the DNA molecule is operably linked to a promoter which is preferentially expressed in target plant cells, and/or optionally wherein the target plant cells are meristem cells.

29. The method according to any one of embodiments 21 to 28, wherein the composition comprises both a first and a second RNA molecule each comprising a cargo segment fused to an MTS, wherein the cargo segment of the first RNA molecule comprises guide RNAs which are distinct from the guide RNAs of the second RNA molecule, optionally wherein the guide RNAs of the first and second RNA molecule are flanked by or comprise processing elements which are processed by different RNA-guided nucleases.

30. The method according to embodiment 29, wherein the composition comprises both a first and a second RNA molecule each comprising a cargo segment fused to an MTS, wherein at least the first RNA molecule comprises a cargo sequence further comprising an RNA-guided nuclease polypeptide-encoding sequence, wherein the cargo segment of the first RNA molecule comprises guide RNAs which are distinct from the guide RNAs of the second RNA molecule.

31. The method according to embodiment 29, wherein the guide RNAs of the first and second RNA molecule are flanked by or comprise processing elements which are processed by different RNA-guided nucleases, and optionally wherein the processing elements in the first RNA molecule are not recognized by the RNA-guided nuclease polypeptide encoded by the first RNA molecule.

32. A plant comprising:

(i) an RNA molecule comprising a cargo segment fused to a meristem transport segment, wherein the cargo segment comprises one or more guide RNAs for an RNA-guided nuclease or a vector encoding the RNA molecule or wherein the cargo segment comprises RNA encoding a TALEN or ZFN protein; and, (ii) a DNA molecule or RNA molecule encoding the RNA-guided nuclease.

33. The plant according to embodiment 32, wherein the cargo segment does not contain a sequence encoding the RNA-guided nuclease.

34. The plant according to embodiment 32 or 33, wherein the cargo segment comprises a plurality of guide RNAs.

35. The plant according to any one of embodiments 32 to 34, wherein the guide RNAs and the direct repeat sequences of the bacterial CRISPR array are for a Cas12a or a Cas12j RNA-guided nuclease.

36. The plant according to any one of embodiments 32 to 35, wherein the plant comprises both a first and a second RNA molecule each comprising a cargo segment fused to an MTS, wherein the cargo segment of the first RNA molecule comprises guide RNAs which are distinct from the guide RNAs of the second RNA molecule, optionally wherein the guide RNAs of the first and second RNA molecule are flanked by or comprise processing elements which are processed by different RNA-guided nucleases.

37. The plant according to any one of embodiments 32, or 34 to 36, wherein the cargo segment contains a sequence encoding a Cas12a or a Cas12j RNA-guided nuclease, optionally wherein the Cas12a RNA-guided nuclease comprises SEQ ID NO: 53 or 55, or optionally wherein the Cas12j RNA-guided nuclease comprises SEQ ID NO: 57, 59, or 61.

38. The plant according to any one of embodiments 32, or 34 to 36, wherein the cargo segment further comprises an RNA-guided nuclease polypeptide-encoding sequence, optionally wherein a Cas12a or a Cas12j RNA-guided nuclease is encoded.

39. The plant according to embodiment 37 or 38, wherein RNA-guided nuclease polypeptide-encoding sequence can be translated in a plant cell cytosol.

40. The plant according to any one of embodiments 37, 38, or 39, the RNA molecule further comprising a polyA region, wherein the polyA region is 3' of the RNA-guided nuclease polypeptide-encoding sequence, and 5' of the guide RNA.

41. The plant according to any one of embodiments 32, or 34 to 40, wherein the composition comprises both a first and a second RNA molecule each comprising a cargo segment fused to an MTS, wherein at least the first RNA molecule comprises a cargo sequence further comprising an RNA-guided nuclease polypeptide-encoding sequence, wherein the cargo segment of the first RNA molecule comprises guide RNAs which are distinct from the guide RNAs of the second RNA molecule.

42. The plant according to embodiment 41, wherein the guide RNAs of the first and second RNA molecule are flanked by or comprise processing elements which are processed by different RNA-guided nucleases, and optionally wherein the processing elements in the first RNA molecule are not recognized by the RNA-guided nuclease polypeptide encoded by the first RNA molecule.

43. The plant according to any one of embodiments 32 to 42, wherein the MTS comprises:

(i) a Flowering Time (FT)-derived sequence, optionally wherein the FT-derived sequence is SEQ ID NO: 5, 6, 7, 8, 9, 10, 11, 12, 13, 14, 15, 16, 17, 18, 19, 20, 21, 22, 23, 24, or a meristem transport-competent (MTC) fragment thereof;

(ii) a tRNA like sequence (TLS), optionally wherein the TLS sequence comprises SEQ ID NO: 29, SEQ ID NO: 30, a MTC fragment thereof, and/or an RNA hairpin comprising a first stem of 8 to 12 nucleotides, at least one variable bulge, a second stem of 4 to 7 nucleotides, and a variable loop;

(iii) a GAI sequence, optionally wherein the GAI sequence comprises SEQ ID NO: 26, a meristem transport-competent (MTC) ortholog thereof, a MTC variant thereof, and/or a MTC fragment thereof, (iv) a BEL5 sequence optionally wherein the BEL5 sequence comprises SEQ ID NO: 28, a meristem transport-competent (MTC) ortholog thereof, a MTC variant thereof, and/or a MTC fragment thereof, (v) a CmNACP sequence optionally wherein the CmNACP sequence comprises SEQ ID NO: 25, a meristem transport-competent (MTC) ortholog thereof, a MTC variant thereof, and/or a MTC fragment thereof; or (vi) a LeT6 sequence optionally wherein the LeT6 sequence comprises SEQ ID NO: 27, a meristem transport-competent (MTC) ortholog thereof, a MTC variant thereof, a MTC fragment thereof.

44. The plant according to embodiment 43, wherein the MTS comprises a Flowering Time (FT)-derived sequence of SEQ ID NO: 5, 6, 7, 8, 9, 10, 11, 12, 13, 14, 15, 16, 17, 18, 19, 20, 21, 22, 23, 24, or a meristem transport-competent (MTC) fragment thereof.

45. The plant according to any one of embodiments 32 to 44, wherein the MTS is located 3' of the cargo segment.

46. The plant according to any one of embodiments 32 to 45, wherein an active form of the RNA guided nuclease is predominantly localized in meristem tissue of the plant.

47. The plant of any one of embodiments 32, or 34 to 46, wherein the RNA-guided nuclease is encoded by a DNA molecule and optionally wherein the DNA molecule is integrated into the genome of the plant.

48. The plant of embodiment 47, wherein the DNA molecule encoding the RNA-guided nuclease is operably linked to a promoter which is preferentially expressed in target plant cells and optionally wherein the target plant cells are meristem cells.

49. A plant comprising an altered genome made by the method of any one of embodiments 21 to 31.

50. The use of the composition of any one of embodiments 1 to 18 to obtain a plant with an altered genome.

EXAMPLES

Example 1—RNA Design

The basic plasmid design to produce the editing message starts with a standard high copy plasmid that contains a multiple cloning sites downstream of the T7 promoter, such as pBluescript™ or pSP73. Each component can be easily introduced using an efficient assembly approach. The design consists of a plant codon optimized Cas12a coding sequence followed by the DR sequence of the Cas12a CRISPR array, in which the DNA-targeting spacer sequences are replaced a guide with soybean phytoene desaturase (PDS) gene as a visual marker (Du et al. J. Biotech 2016, 217:90-97; doi.org/10.1016/j.jbiotec.2015.11.005). The guide RNA region is followed by the an FT sequence derived from Arabidopsis (SEQ ID NO: 1). The DNA vector sequence ends in a unique restriction site to linearize the plasmid for runoff transcription. This arrangement enables production of high quantity editing mRNA.

Example 2—Production of the RNA Composition

To produce the mRNA for plant delivery the production vector above is linearized as template for in vitro transcription to produce tens of micrograms of editing mRNA using a system such as mScript™ (CAMBIO, Cambridge, UK; on the world wide web https internet site "cambio.co.uk/20/431/21/products/t7-mscript-standard-mrna-production-system/"). The product is cleaned up and characterized to make sure it is the expected size and to determine how much mRNA was produced. The purification process includes a DNAase treatment followed by a phenol chloroform extraction then ethanol precipitation and resuspension in RNase free water. RNAase inhibitor is also added (New England Biolabs, Ipswich, MA, USA; on the world wide web https internet site "neb.com/products/m0314-rnase-inhibitor-murine#Product%20Information") to stabilize the editing mRNA during uptake by the plant.

Example 3—Phloem Loading

The in vitro transcription reaction of Example 2 produces 50 micrograms of editing mRNA. It is suspended in a mix at 0.2 micrograms per microliter (10 micrograms mRNA in 50 microliters of RNase free water) in nuclease-free Eppendorf™ tubes (1.5 mL). These steps produce sufficient material for five replicates. A negative control contains everything but the editing mRNA. The soy plants are at the 2-3 trifoliate stage in small pots. Using sharp, clean & heat sterilized scissors to remove a leaf tip in the second trifoliate of each plant then the leaf tip is cut when submerged in sterile nuclease free water. Very gently the leaf is placed in the RNA solution and the setup stabilized so the plant can absorb the mRNA solution with no undue stress. Uptake of the editing mRNA takes several hours.

Example 4—Phenotyping

The treated leaves are removed from the editing mRNA tubes when the solution is depleted to minimize wounding. In 1-2 weeks for the intended phenotype will appear in new growth. The soy PDS knockout is lethal so the plants will likely not set seed, but the same method can be adapted to make non-lethal mutations that are transmissible through in the germline.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this disclosure have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the invention as encompassed by the embodiments of the inventions recited herein and the specification and appended claims.

What is claimed is:

1. A composition comprising at least one RNA molecule comprising a cargo segment fused to a meristem transport segment (MTS), wherein the cargo segment comprises one or more guide RNAs for an RNA-guided nuclease, wherein the RNA molecule is a substantially purified RNA molecule.

2. The composition according to claim 1, wherein the guide RNA is flanked by or comprises processing elements.

3. The composition according to claim 2, wherein the processing elements are direct repeat sequences of a bacterial CRISPR array of the RNA-guided nuclease or are direct repeat sequences that are processed by the RNA-guided nuclease.

4. The composition according to claim 3, wherein the cargo segment comprises a plurality of guide RNAs.

5. The composition according to claim 3, wherein the guide RNAs and the direct repeat sequences of the bacterial CRISPR array are for a Cas12a or a Cas12j RNA-guided nuclease.

6. The composition according to claim 1, wherein the composition comprises both a first and a second RNA molecule each comprising a cargo segment fused to an MTS and wherein the cargo segment of the first RNA molecule comprises one or more guide RNAs for an RNA-guided nuclease.

7. The composition according to claim 6, wherein the cargo segment of the first RNA molecule comprises guide RNAs which are distinct from the guide RNAs of the second RNA molecule.

8. The composition according to claim 1, wherein the cargo segment does not contain an RNA-guided nuclease polypeptide-encoding sequence.

9. The composition according to claim 1, wherein the cargo segment further comprises an RNA-guided nuclease polypeptide-encoding sequence.

10. The composition according to claim 6, wherein the cargo segment of the first RNA molecule comprises guide RNAs and wherein the cargo segment of the second RNA molecule comprises an RNA-guided nuclease polypeptide-encoding sequence.

11. The composition according to claim 9, wherein the RNA-guided nuclease polypeptide-encoding sequence can be translated in a plant cell cytosol.

12. The composition according to claim 11, wherein the RNA molecule further comprises a polyA region.

13. The composition according to claim 12, wherein the poly A region is 3' of the RNA-guided nuclease polypeptide-encoding sequence, and 5' of the guide RNA.

14. The composition according to claim 7, wherein the guide RNAs of the first and second RNA molecule are flanked by or comprise processing elements which are processed by different RNA-guided nucleases.

15. The composition according to claim 1, wherein the MTS comprises:

(i) a Flowering Time (FT)-derived sequence or (ii) a tRNA like sequence (TLS).

16. The composition according to claim 15, wherein the MTS comprises a Flowering Time (FT)-derived sequence of SEQ ID NO: 5, 6, 7, 8, 9, 10, 11, 12, 13, 14, 15, 16, 17, 18, 19, 20, 21, 22, 23, 24, or a meristem transport-competent (MTC) fragment thereof.

17. The composition according to claim 1, wherein the MTS is located 3' of the cargo segment.

18. The composition according to claim 1, further comprising an RNase inhibitor.

19. The composition according to claim 1, wherein the RNA molecule is not operably linked to a viral vector RNA and/or associated with a viral protein.

20. A method of producing a plant or plant part with an altered genome comprising:

(i) contacting a plant or plant part with at least a first composition according to claim 1; and (ii) retrieving a progeny or descendant of the plant or plant part, wherein the progeny or descendent has an altered genome.

21. The method according to claim 20, wherein contacting comprises phloem loading.

22. The method according to claim 20, wherein the contacting with the composition occurs at the vegetative stage of the plant life cycle.

23. A plant or plant part comprising an altered genome made by the method of claim 20.

* * * * *